US011602522B2

(12) United States Patent
Pentikis et al.

(10) Patent No.: US 11,602,522 B2
(45) Date of Patent: *Mar. 14, 2023

(54) SECNIDAZOLE FOR USE IN THE TREATMENT OF SEXUALLY TRANSMITTED INFECTION

(71) Applicant: LUPIN INC., Baltimore, MD (US)

(72) Inventors: Helen S. Pentikis, Timonium, MD (US); David Palling, Glen Ridge, NJ (US); Carol J. Braun, Ellicott City, MD (US); Richard Holl, Somerset, NJ (US)

(73) Assignee: LUPIN INC., Baltimore, MD (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/314,833

(22) Filed: May 7, 2021

(65) Prior Publication Data

US 2021/0260038 A1  Aug. 26, 2021

Related U.S. Application Data

(63) Continuation of application No. 16/817,246, filed on Mar. 12, 2020, now Pat. No. 11,000,507, which is a continuation of application No. 16/049,032, filed on Jul. 30, 2018, now Pat. No. 10,682,338, which is a continuation-in-part of application No. 14/846,505, filed on Sep. 4, 2015, now Pat. No. 10,335,390.

(60) Provisional application No. 62/101,636, filed on Jan. 9, 2015, provisional application No. 62/046,731, filed on Sep. 5, 2014.

(51) Int. Cl.
A61K 31/4164 (2006.01)
A61K 45/06 (2006.01)
C07D 233/94 (2006.01)
A61K 31/565 (2006.01)
A61K 31/567 (2006.01)
A61K 9/00 (2006.01)
A61K 9/16 (2006.01)
A61K 9/50 (2006.01)

(52) U.S. Cl.
CPC ........ *A61K 31/4164* (2013.01); *A61K 9/0053* (2013.01); *A61K 9/1676* (2013.01); *A61K 9/5078* (2013.01); *A61K 31/565* (2013.01); *A61K 31/567* (2013.01); *A61K 45/06* (2013.01); *C07D 233/94* (2013.01)

(58) Field of Classification Search
CPC .............. A61K 31/4164; A61K 9/0053; A61K 9/1676; A61K 9/5078; A61K 31/565; A61K 31/567; A61K 45/06; C07D 233/94
See application file for complete search history.

(56) References Cited

U.S. PATENT DOCUMENTS

| | | |
|---|---|---|
| 3,376,311 A | 4/1968 | Butler |
| 4,803,066 A | 2/1989 | Edwards |
| 4,920,141 A | 4/1990 | Hortstmann et al. |
| 4,925,950 A | 5/1990 | Massonneau et al. |
| 4,925,951 A | 5/1990 | Massonneau et al. |
| 4,925,952 A | 5/1990 | Massonneau et al. |
| 4,957,918 A | 9/1990 | Martin et al. |
| 5,023,361 A | 6/1991 | Massonneau et al. |
| 5,026,694 A | 6/1991 | Skov et al. |
| 5,140,055 A | 8/1992 | Hirata et al. |
| 5,329,003 A | 7/1994 | Bruchmann |
| 5,460,828 A | 10/1995 | Santus et al. |
| 5,549,911 A | 8/1996 | Leduc et al. |
| 5,574,167 A | 11/1996 | Jaber |
| 5,614,545 A | 3/1997 | Martin et al. |
| 5,719,122 A | 2/1998 | Chiodini et al. |
| 5,904,937 A | 5/1999 | Augello et al. |
| 6,103,262 A | 8/2000 | Desai et al. |
| 6,140,355 A | 10/2000 | Egidio et al. |

(Continued)

FOREIGN PATENT DOCUMENTS

| | | |
|---|---|---|
| AU | 1995/15803 | 8/1995 |
| CN | 1546020 A | 11/2004 |

(Continued)

OTHER PUBLICATIONS

International Search Report and Written Opinion for PCT/US2016/035299 dated Aug. 22, 2016.
Bohbot et al., "Treatment of Bacterial Vaginosis: A Multicenter, Double-Blind, Double-Dummy, Randomised Phase III Study.," Hindawi Pub. Corp., Infectious Diseas. (2010), 1-6.
Nunez et al., "Low-dose secnidazole in the treatment of bacterial vaginosis," International Journal of Gynecology and Obstetrics (2005), 88:281-285.

(Continued)

*Primary Examiner* — Robert A Wax
*Assistant Examiner* — Olga V. Tcherkasskaya
(74) *Attorney, Agent, or Firm* — Duane Morris LLP

(57) ABSTRACT

Method of treating sexually transmitted infection in a subject in need thereof involving administering to the subject a therapeutically effective amount of secnidazole in a microgranule formulation, wherein the microgranule formulation comprises a plurality of microgranules having a volume-weighted particle size distribution within a microgranule population, wherein the volume-weighted particle size distribution as measured from a representative sample of the microgranule population comprises (a) 10% of the microgranule population having a volume-weighted particle size about no less than 470 micrometers; (b) 50% of the microgranule population having a volume-weighted particle size between about no less than 640 micrometers and about no more than 810 micrometers; (c) 90% of the microgranule population having a volume-weighted particle size about no more than 1170 micrometers; or (d) a combination thereof, which can include some or all of (a) through (c) above. Pharmaceutical compositions and uses thereof are included herein.

22 Claims, 5 Drawing Sheets

(56) References Cited

U.S. PATENT DOCUMENTS

| | | |
|---|---|---|
| 6,214,386 B1 | 4/2001 | Santus et al. |
| 6,653,333 B2 | 11/2003 | Yotsuya et al. |
| 6,794,372 B2 | 9/2004 | Del Soldato et al. |
| 6,794,411 B1 | 9/2004 | Lebon et al. |
| 7,485,729 B2 | 2/2009 | Hsieh et al. |
| 7,691,831 B2 | 4/2010 | Bonner, Jr. et al. |
| 7,700,076 B2 | 4/2010 | Tamarkin et al. |
| 7,820,145 B2 | 10/2010 | Tamarkin et al. |
| 7,884,090 B2 | 2/2011 | Bonner, Jr. et al. |
| 7,893,097 B2 | 2/2011 | Yang et al. |
| 8,088,846 B2 | 1/2012 | Hsieh et al. |
| 8,158,152 B2 | 4/2012 | Palepu |
| 8,309,103 B2 | 11/2012 | Hernandez-Ramirez et al. |
| 8,318,132 B2 | 11/2012 | Kolb et al. |
| 8,642,660 B2 | 2/2014 | Goldfarb |
| 8,658,678 B2 | 2/2014 | Yang et al. |
| 8,772,242 B2 | 7/2014 | Borody |
| 8,853,247 B2 | 10/2014 | Ren et al. |
| 8,877,792 B2 | 11/2014 | Yang et al. |
| 8,912,113 B2 | 12/2014 | Ravichandran et al. |
| 8,946,276 B2 | 2/2015 | Nordsiek et al. |
| 8,999,360 B2 | 4/2015 | Borody et al. |
| 9,006,316 B2 | 4/2015 | Hsieh et al. |
| 9,016,221 B2 | 4/2015 | Brennan et al. |
| 10,682,338 B2 | 6/2020 | Pentikis et al. |
| 10,849,884 B2 | 12/2020 | Pentikis et al. |
| 10,857,133 B2 | 12/2020 | Pentikis et al. |
| 2003/0001721 A1 | 1/2003 | Debregeas et al. |
| 2003/0091540 A1 | 5/2003 | Ahmad et al. |
| 2003/0092754 A1 | 5/2003 | Nishimuta et al. |
| 2004/0033968 A1 | 2/2004 | Lin et al. |
| 2005/0026982 A1 | 2/2005 | Johannsen et al. |
| 2005/0043408 A1 | 2/2005 | Yeboah et al. |
| 2005/0069566 A1 | 3/2005 | Tamarkin et al. |
| 2005/0165077 A1 | 7/2005 | Hernandez-Ramirez et al. |
| 2005/0186142 A1 | 8/2005 | Tamarkin et al. |
| 2005/0222169 A1 | 10/2005 | Ahmad et al. |
| 2005/0261298 A1 | 11/2005 | Solow-Cordero et al. |
| 2005/0262647 A1 | 12/2005 | Hoeffkes et al. |
| 2006/0024243 A1 | 2/2006 | Arkin et al. |
| 2006/0137684 A1 | 6/2006 | Evans et al. |
| 2006/0140984 A1 | 6/2006 | Tamarkin et al. |
| 2006/0140990 A1 | 6/2006 | Bortz et al. |
| 2006/0142304 A1 | 6/2006 | Southall et al. |
| 2006/0269485 A1 | 11/2006 | Friedman et al. |
| 2007/0015841 A1 | 1/2007 | Tawa et al. |
| 2007/0154516 A1 | 7/2007 | Bortz et al. |
| 2007/0255064 A1 | 11/2007 | Szarvas et al. |
| 2007/0287714 A1 | 12/2007 | Ahmad et al. |
| 2007/0292355 A1 | 12/2007 | Tamarkin et al. |
| 2008/0139664 A1 | 6/2008 | Yeboah et al. |
| 2008/0171709 A1 | 7/2008 | Remmal |
| 2008/0171768 A1 | 7/2008 | Remmal |
| 2009/0131342 A1 | 5/2009 | Ellis |
| 2010/0159035 A1 | 6/2010 | Shemer |
| 2010/0304998 A1 | 12/2010 | Sem |
| 2011/0002866 A1 | 1/2011 | Lubit et al. |
| 2011/0046378 A1 | 2/2011 | Kolb et al. |
| 2011/0053941 A1 | 3/2011 | Mautino et al. |
| 2011/0207702 A1 | 8/2011 | Jacobs et al. |
| 2012/0219500 A1 | 8/2012 | Sakurai et al. |
| 2012/0295839 A1 | 11/2012 | Paull et al. |
| 2013/0309219 A1 | 11/2013 | Ratner et al. |
| 2014/0065230 A1 | 3/2014 | Shah et al. |
| 2014/0080778 A1 | 3/2014 | Defrance |
| 2014/0271923 A1 | 9/2014 | Reid |
| 2014/0378520 A1 | 12/2014 | Ren et al. |
| 2015/0196536 A1 | 7/2015 | Yang et al. |
| 2016/0346252 A1 | 12/2016 | Palling et al. |

FOREIGN PATENT DOCUMENTS

| | | |
|---|---|---|
| CN | 1789250 A | 6/2006 |
| CN | 1973838 A | 6/2007 |
| CN | 101255175 A | 9/2008 |
| CN | 102266284 A | 12/2011 |
| CN | 102335433 A | 2/2012 |
| CN | 104257626 A | 1/2015 |
| EP | 0216453 A2 | 7/1986 |
| EP | 0206625 A2 | 12/1986 |
| EP | 0293090 A2 | 4/1988 |
| EP | 0348808 A2 | 1/1990 |
| EP | 0406665 A1 | 6/1990 |
| EP | 0378137 A | 7/1990 |
| EP | 0413533 A | 2/1991 |
| EP | 0717992 A | 6/1996 |
| GB | 2033232 A | 10/1978 |
| GB | 2103927 A | 3/1983 |
| JP | H9-507499 | 7/1997 |
| JP | 2017-526697 A | 3/2016 |
| WO | WO 85/03000 A | 7/1985 |
| WO | WO 87/06129 A1 | 10/1987 |
| WO | WO 91/17744 | 11/1991 |
| WO | WO 93/12771 A | 7/1993 |
| WO | WO 96/35436 A | 11/1996 |
| WO | WO 2000/059468 A1 | 10/2000 |
| WO | WO 2012/075015 A2 | 6/2012 |
| WO | WO 2014/121298 A2 | 8/2014 |
| WO | WO 2016/037131 A1 | 3/2016 |
| WO | WO 2016/196653 A1 | 12/2016 |

OTHER PUBLICATIONS

Menard, John-Pierre, "Antibacterial treatment of bacterial vaginosis: current and emerging therapies," International Journal of Women's Health (2011), 3:295-305.

International Search Report and Written Opinion for PCT/US2015/048681 dated Jan. 19, 2016.

International Search Report for PCT/FR95/00039 dated Jun. 14, 1995.

Rinshou to Kenkyu (2003), 80(5):45 [No. English version available.]

Acar et al., "Le secnidazole, un nouveau 5-nitro imidazole," Antibiotiques (2005), 7:177-182 [English Abstract].

Dubreuil et al., "Le secnidazole: activité antibactérienne sur les anaérobies stricts," Antibiotiques (2005), 7:239-246 [English Abstract].

Hangargekar et al., "Formulation and Evaluation of Guar Gum Based Colon Targeted . . . ," International Journal of Pharmacy and Pharmaceutical Sciences (2011), 3(4):294-298.

Malholtra, "Ciprofloxacin-tinidazol combination, fluconazole-azithromycin-secnidazole-kit and . . . ," Indian Journal of Medicinal Sciences (Dec. 1, 2003), 57 (12):549-555.

Narayana et al., "Formulation and In Vitro Evaluation of In Situ Gels Containing Secnidazole for Vaginitis," Yakugaku Zasshi (2009), 129(5):569-574.

Rao et al., "In Vitro Susceptibility Testing of Nonsporing Anaerobes to Ten Antimicrobial Agents," Indian J. Pathol. Microbial, (2000), 43(1):139-142.

Australian Patent Application No. 15803/95, filed Jan. 12, 1995, which is a national stage entry of PCT/FR1995/00039.

Baichwal et al., "Microencapsulation of Metronidazole," Indian J. Pharma. Sciences, (1980), 42(2):48-51.

Aug. 27, 2018 Decision of Rejection in connection with Japanese Patent Application No. 2017-512757 [English translation included].

Amsel, Richard, et al. "Nonspecific Vaginitis. Diagnostic Criteria and Microbial and Epidemiologic Associations," Am. J. Med., 74 (1): 14-22 (1983).

Dec. 27, 2018 Notice of Final Rejection in connection with Korean Patent Application No. 2017-7009154 [English translation included].

Shekunov et al., "Partide Size Analysis in Pharmaceutics: Principles, Methods and Applications", Pharmaceutical Research (2007), 24(2):203-227.

Sun et al., "Particle Size Specifications for Solid Oral Dosage Forms: A Regulatory Perspective", American Pharmaceutical Review: https://www.americanpharmaceuticalreview.com/Featured-Articles/36779-Particle-Size-Specifications-for-Solid-Oral-Dosage-Forms-A-Regulatory-Perspective/ (2010) 10p.

(56) References Cited

OTHER PUBLICATIONS

Videau, et al., "Secnidazole: A 5-nitroimidazole derivative with a long half-life," British Journal of Veneral Diseases (1978), 55:77-80.
Jun. 1, 2020 Decision of Appeal issued by the Korean Intellectual Property Office in connection with Korean Patent Application No. 2017-70091547. [With English translation.
Schwebke, et al., "Intravaginal Metronidazole/Miconazole for the Treatment of Vaginal Trichomoniasis," Sexually Transmitted Diseases (2013), 40(9):710-714.
Austin, et al., "Metronidazole in a single dose for the treatment of trichomoniasis," British Journal of Veneral Diseases (1982), 58:121-123.
Patel, et al., "Prevalence and Correlates of Trichomonas Vaginalis Infection Among Men and Women in the United States," Clinical Infectious Diseases (2018), 67:211-217.
Ozbilgin, et al., "Trichomoniasis in Non-Gonococcic Urethritis Among Male Patients," Journal of the Egyptian Society of Parasitology (1994), 24(3):621-625.
Siboulet, et al., "Urogenital Trichomoniasis. Trials with a Long Half-Life Imidazone: Secnidazole," Medecine et Maladies Infectiesus, (1977), 7-9:400-409.
Cotch, et al., "Trichomonas vaginalis Associated with Low Birth Weight and Preterm Delivery," Sexually Transmitted Diseases (1977), 24(6):353-360.
Shuter, et al., "Rates of and Risk Factors of Trichmoniasis Among Pregnant Inmates in New York City," Sexually Transmitted Diseases (1998), 25 (6):303-307.
Cu-Uvin, et al., "Prevalence, Incidence, and Persistence or Recurrence of Trichomoniasis among Human Immunodeficiency Virus (HIV)-Positive Women and among HIV-Negative Women at High Risk for HIV Infection," Clin. Infect. Dis. (2002), 34(10):1406-1141.
Miller, et al., "HIV, the Clustering of Sexually Transmitted Infections, and Sex Risk Among African American Women Who Use Drugs," Sexually Transmitted Diseases (2008), 35(7):696-702.
Kissinger, et al., "Trichomonas Vaginalis Treatment Reduces Vaginal HIV-1 Shedding," Sexually Transmitted Diseases (2009), 36(1):11-16.
Sutcliffe, et al., "Prevalence and Correlates of Trichomonas vaginalis Infection Among Female US Federal Prison Inmates," Sexually Transmitted Diseases (2010), 37(9):585-590.
Sosman, et al., "Sexually Transmitted Infection and Hepatitis in Men With a History of Incarceration," Sexually Transmitted Diseases (2011), 38(7):634-639.
Satterwhite, et al., "Sexually Transmitted Infections Among US Women and Men:Prevalence and Incidence Estimates, 2008," Sexually Transmitted Diseases (2013), 49(3): 187-193.
Meites, et al., "Trichomonas vaginalis in Selected US Sexually Transmitted Disease Clinics: Testing, Screening, and Prevalence," Sexually Transmitted Diseases (2013), 40(11):865-869.
Kissinger, et al., "A Randomized Treatment Trial: Single Versus 7-Day Dose of Metronidazole for the Treatment of Trichomonas Vaginalis Among HIV-Infected Women," Journal of Acquired Immune Defiency Syndromes (2010), 55(5):565-571.
Crosby, et al., Condom effectiveness against non-viral sexually transmitted infections: a prospective study using electronic daily diaries, Sexually Transmitted Infections (2012), 88:484-489.
Peterman, et al., "High Incidence of New Sexually Transmitted Infections in the Year following a Sexually Transmitted Infection: A Case for Rescreening," Annals of Internal Medicine (2006), 145:564-572.

McClelland, et al., "Infection with Trichomonas vaginalis Increases the Risk of HIV-1 Acquisition," Journal of Infectious Diseases (9227), 195:698-702.
Van Der Pol, et al., Trichomonas Vaginalis Infection and Human Immunodeficiency Virus Acquisition in African Women, Journal of Infection Diseases (2008), 197:546-554.
"Incidence, Prevalence, and Cost of Sexually Transmitted Infections in the United States," CDC Fact Sheet, National Center for HIV/AIDS, Viral Hepitits, STD, and TB Prevention, (Feb. 2013), pp. 1-4.
Ginocchio, et al., "Prevalence of Trichomonas vaginalis and coinfection with Chlamydia trachomatis and Neisseria gonorrhoeae in the United States as determined by the Aptima Trichomonas vaginalis nucleic acid amplification assay," Journal of Clinical Microbiology (2012), 50(8):2601-2608.
Rossignol, et al., "Nitroimidazoles in the treatment of trichomoniasis, giardiasis, and amebiasis," International Journal of Clinical Pharmacology, Therapy, and Toxicology (1984), 22(2):63-72.
Cudmore, et al., "Treatment of infections caused by metronidazole-resistant Trichomonas vaginalis," Clinical Microbiology Reviews (2004), 17(4):783-793.
Sena, et al., "Trichomonas vaginalis infection in male sexual partners: implications for diagnosis, treatment, and prevention," Clinical Infectious Diseases (2007), 44: 13-22.
Moodley, et al., "Trichomonas vaginalis is associated with pelvic inflammatory disease in women infected with human immunodeficiency virus," Clinical Infectious Diseases (2002), 34:519-522.
"2015 Sexually Transmitted Diseases Treatment Guidelines—Trichomoniasis," Centers for Disease Control and Prevention, pp. 1-5.
Minkoff, et al., "Risk factors for prematurity and premature rupture of membranes: a prospective study of the vaginal flora in pregnancy," American Journal of Obstetrics and Gynecology (1984), 150(8):965-972.
Sosman, et al., "Screening for sexually transmitted diseases and hepatitis in 18-29-year-old men recently released from prison: feasibility and acceptability," International Journal of Sexually Transmitted Diseases & AIDS (2005), 1:117-122.
Jun. 22, 2021 Notice of Final Rejection issued by the Korean Intellectual Property Office for Korean Patent Application No. 2019-7006430. [English translation included].
Jul. 8, 2021 First Examination Report issued by the Indian Patent Office for Indian Patent Application No. 202017003278. [English translation included.]
Aug. 3, 2020 Decision of Rejection concerning Japanese Patent Application No. 2018-228992 [English translation included].
Takashi, I., et al., "Estimation of Crystallite Size by Powder X-ray Diffractometry," The Journal of Society of Power Technology in Japan, (2003) 40:177-184.
Nov. 16, 2020 Notice of Preliminary Rejection concerning Korean Patent Application No. 2019-7006430 [English translation included].
Nov. 22, 2021 Notice of Reasons for Rejection issued by the Japanese Patent Office for Japanese Patent Application No. 2020-201018. [English translation included].
Gillis, et al., "Secdinazole—A Review of its Antimicrobial Activity, Pharmacokinetic Properties and Therapeutic Use in the Management of Protozoal Infections and Bacterial Vaginosis", Drugs (1996) 51(4):621-638.
De Backer, E., et al., "In vitro activity of secnidazole against Atopobium vaginae, an anaerobic pathogen involved in bacterial vaginosis", Clinical Microbiology and Infection, (May 2010), 16(5):470-472.

SECNIDAZOLE FOR USE IN THE TREATMENT OF SEXUALLY TRANSMITTED INFECTION

CROSS-REFERENCE TO RELATED APPLICATIONS

This application is a continuation of U.S. patent application Ser. No. 16/817,246, filed Mar. 12, 2020, which is a continuation of U.S. patent application Ser. No. 16/049,032, filed on Jul. 30, 2018, which is now U.S. Pat. No. 10,682,338, issued Jun. 16, 2020, which is a continuation-in-part of U.S. patent application Ser. No. 14/846,505, filed on Sep. 4, 2015, which is now U.S. Pat. No. 10,335,390, issued Jul. 2, 2019, which claims the benefit of priority to U.S. Provisional Patent Application Ser. No. 62/101,636, filed on Jan. 9, 2015 and U.S. Provisional Patent Application Ser. No. 62/046,731, filed on Sep. 5, 2014, each of which is hereby incorporated by reference in its entirety.

BRIEF SUMMARY

Embodiments described herein are directed to a method of treating bacterial vaginosis in a subject in need thereof comprising administering to the subject a therapeutically effective amount of secnidazole in a microgranule formulation. In some embodiments, the secnidazole in a microgranule formulation is administered orally. In some embodiments, the secnidazole in a microgranule formulation comprises a plurality of microgranules. In some embodiments, the plurality of microgranules each have a particle size range of about 400 micrometers to about 841 micrometers. In some embodiments, the microgranule formulation further comprises at least one of sugar spheres, povidone, polyethylene glycol 4000, (poly(ethyl acrylate-co-methyl methacrylate) 2:1, with α-(4-nonylphenyl) ω-hydroxypoly-(oxy-1, 2-ethanediyl) (1.5 wt. %) as excipient), sold under the trademark Eudragit NE30D, talc, colloidal silicon dioxide or a combination thereof. In some embodiments, the microgranule formulation further comprises at least one of sugar spheres, povidone, polyethylene glycol 4000, (poly(ethyl acrylate-co-methyl methacrylate) 2:1, with α-(4-nonylphenyl) ω-hydroxypoly-(oxy-1, 2-ethanediyl) (1.5 wt. %) as excipient), sold under the trademark Eudragit NE30D, talc, or a combination thereof. In some embodiments, the secnidazole in a microgranule formulation may be mixed, stirred, or otherwise integrated into a food substance. In some embodiments, the food substance includes, but is not limited to applesauce, yogurt, and pudding.

In some embodiments, the plurality of microgranules has a volume-weighted particle size distribution within a microgranule population, wherein the volume-weighted particle size distribution as measured from a representative sample of the microgranule population includes:
  (a) 10% of the microgranule population has a volume-weighted particle size about no less than 470 micrometers;
  (b) 50% of the microgranule population has a volume-weighted particle size between about no less than 640 micrometers and about no more than 810 micrometers;
  (c) 90% of the microgranule population has a volume-weighted particle size about no more than 1170 micrometers; or
  (d) a combination thereof, which can include some or all of (a) through (c) above.

As used herein, the term "volume-weighted particle size distribution" refers to a distribution where the contribution of each particle in the distribution relates to the volume of the particle (equivalent to the mass if the density is uniform), i.e., the particles contribution will be proportional to its size (see, e.g., Powder Sampling and Particle Size Determination by T. Allen, 1$^{st}$ Edition., Elsevier Science, 2003 and Particle Size Measurement by T. Allen, Chapman & Hall, 4$^{th}$ Edition, 1992). Static light scattering techniques such as laser diffraction and other techniques known in the art can be used to determine volume-weighted particle size distribution.

In some embodiments, the subject is a female. In some embodiments, the subject is an otherwise healthy female. In some embodiments, the subject is a pregnant female. In some embodiments, the subject is an otherwise healthy pregnant female. In some embodiments, the subject is a female having had 3 or fewer bacterial vaginosis infections/episodes in the past 12 months. In some embodiments, the subject is a female having had 4 or more bacterial vaginosis infections/episodes in the past 12 months. In some embodiments, the subject is a female presenting with an off-white (milky or gray), thin, homogeneous vaginal discharge, an odor, or a combination thereof. In some embodiments, the subject is a female presenting with abnormal vaginal discharge, a positive Potassium Hydroxide (KOH) Whiff test, vaginal fluid pH greater than or equal to 4.7, and the presence of "clue cells" greater than 20% of total epithelial cells or any combination thereof. In some embodiments, the subject is a female with confirmed bacterial vaginosis. In some embodiments, the female with confirmed bacterial vaginosis presents with an off-white (milky or gray), thin, homogeneous vaginal discharge, an odor, or a combination thereof. In some embodiments, the subject is a female presenting with abnormal vaginal discharge, a positive KOH Whiff test, vaginal fluid pH greater than or equal to 4.7, and the presence of "clue cells" greater than 20% of total epithelial cells or any combination thereof. In some embodiments, the female with confirmed bacterial vaginosis presents with four Amsel criteria parameters and a gram stain slide Nugent score equal to, or higher than four on bacterial analysis of vaginal samples. In some embodiments, the four Amsel criteria parameters are abnormal vaginal discharge, a positive KOH Whiff test, vaginal fluid pH greater than or equal to 4.7, and the presence of clue cells greater than 20% of total epithelial cells. In some embodiments, the subject is a female with suspected bacterial vaginosis. In some embodiments, the female with suspected bacterial vaginosis presents with an off-white (milky or gray), thin, homogeneous vaginal discharge, an odor, or a combination thereof. In some embodiments, the subject is a female presenting with abnormal vaginal discharge, a positive KOH Whiff test, vaginal fluid pH greater than or equal to 4.7, and the presence of "clue cells" greater than 20% of total epithelial cells or any combination thereof. In some embodiments, the female with suspected bacterial vaginosis presents with four Amsel criteria parameters. In some embodiments, the four Amsel criteria parameters are abnormal vaginal discharge, a positive KOH Whiff test, vaginal fluid pH greater than or equal to 4.7, and the presence of clue cells greater than 20% of total epithelial cells.

In some embodiments, the therapeutically effective amount of secnidazole in a microgranule formulation is administered as a single dose. In some embodiments, the therapeutically effective amount of secnidazole in a microgranule formulation administered as a single dose is the only dose required to be administered to the subject to achieve a post treatment clinical outcome, resolution of one or more symptoms of bacterial vaginosis, or a combination thereof. In some embodiments, the therapeutically effective amount of secnidazole in a microgranule formulation is 2 grams. In some embodiments, the therapeutically effective amount of secnidazole in a microgranule formulation is an amount of secnidazole in a microgranule formulation that exhibits a maximum serum concentration ($C_{max}$) of between about 34.5 μg/ml and about 58.3 μg/ml in the subject. In some embodiments, the therapeutically effective amount of secnidazole in a microgranule formulation is an amount of secnidazole in a microgranule formulation that exhibits a maximum serum concentration ($C_{max}$) of between about 17.4 μg/ml and about 26.5 μg/ml in the subject. In some embodiments, the therapeutically effective amount of secnidazole in a microgranule formulation is an amount of secnidazole that exhibits a time to maximum plasma concentration ($T_{max}$) of about 3 hours to about 4.05 hours. In some embodiments, the therapeutically effective amount of secnidazole in a microgranule formulation is an amount of secnidazole that exhibits a time to maximum plasma concentration ($T_{max}$) of about 2 hours to about 6 hours. In some embodiments, the therapeutically effective amount of secnidazole in a microgranule formulation is co-administered with an additional compound selected from ethinyl estradiol (EE2), norethindrone (NET), and a combination thereof.

Some embodiments further comprise determining a post-treatment clinical outcome. In some embodiments, a post-treatment clinical outcome is indicative of a clinical outcome responder. Some embodiments further comprise determining a post-treatment clinical outcome. In some embodiments, a post-treatment clinical outcome of clinical cure is defined as a clinical outcome responder. In some embodiments, a clinical outcome responder is a subject with normal vaginal discharge, a negative KOH Whiff test, and clue cells less than 20% of total epithelial cells, post-treatment. In some embodiments, a clinical outcome responder is a subject with a gram stain slide Nugent score of less than four, post-treatment. In some embodiments, a clinical outcome responder is a subject with normal vaginal discharge, a negative KOH Whiff test, clue cells less than 20% of total epithelial cells), and a gram stain slide Nugent score of less than four, post-treatment. In some embodiments, administering to the subject a therapeutically effective amount of secnidazole in a microgranule formulation results in better than expected effectiveness than Food and Drug Administration (FDA)-approved drugs used in the treatment of bacterial vaginosis. In some embodiments, administering to the subject a therapeutically effective amount of secnidazole in a microgranule formulation results in superior effectiveness than FDA-approved drugs used in the treatment of bacterial vaginosis. In some embodiments, administering to the subject a therapeutically effective amount of secnidazole in a microgranule formulation results in a higher rate of clinical cure than FDA-approved drugs used in the treatment of bacterial vaginosis. In some embodiments, administering to the subject a therapeutically effective amount of secnidazole in a microgranule formulation results in a better than expected safety profile than FDA-approved drugs used in the treatment of bacterial vaginosis. In some embodiments, administering to the subject a therapeutically effective amount of secnidazole in a microgranule formulation results in a more favorable safety profile than FDA-approved drugs used in the treatment of bacterial vaginosis. In some embodiments, the therapeutically effective amount of secnidazole in a microgranule formulation is mixed into a food substance. In some embodiments, the food substance includes, but is not limited to applesauce, yogurt, and pudding.

Some embodiments further comprise administering an additional compound selected from ethinyl estradiol (EE2), norethindrone (NET), or a combination thereof. In some embodiments, the additional compound is administered on the same day as the secnidazole microgranule formulation. In some embodiments, the additional compound is administered on a different day than the secnidazole microgranule formulation. In some embodiments, the secnidazole microgranule formulation does not affect the contraceptive efficacy of the additional compound. In some embodiments, the subject has a resolution of one or more symptoms of bacterial vaginosis within up to about seven days after administration. In some embodiments, the subject has an alleviation of one or more symptoms of bacterial vaginosis within up to about three days after administration.

Embodiments herein are directed to a microgranule formulation comprising secnidazole, or pharmaceutically acceptable salts thereof. In some embodiments, the microgranule formulation comprises a therapeutically effective amount of secnidazole, or pharmaceutically acceptable salts thereof. In some embodiments, the microgranule formulation is a taste-masked formulation. In some embodiments, the microgranule formulation is a physically taste-masked formulation. Methods of taste masking that are readily available in the art, such as coating, can be used on the microgranule formulations set forth in this application. For example, coating of a microgranule formulation containing an Active Pharmaceutical Ingredient ("API") can be done by coating, e.g., each of the microgranules containing an API. Ideally, the polymers selected in coating should be such that they prevent API release in oral cavity and allow its release in the absorption window of the API. For example, a physically taste-masked formulation can have an outer coat or a layer that acts as a dissolution barrier that inhibits instantaneous dissolution of the API in, e.g., a liquid or upon oral administration. In some embodiments, the physically taste-masked formulation has an outer coat or layer that acts as a slight barrier to dissolution but not to degree that would inhibit immediate absorption of the API upon administration.

In some embodiments, the taste-masked microgranule formulation can be a delayed release formulation, an immediate release formulation, or an extended release formulation. In some embodiments, the taste-masked formulation is a modified-delayed release formulation (also called a physically taste-masked formulation) such that it has an outer coat or layer which acts as a barrier to dissolution and the formulation achieves absorption kinetics similar to an immediate-release dosage form. In some embodiments, the modified-delayed release formulation has an outer coat or layer that acts as a barrier to dissolution and the formulation achieves absorption kinetics that is not extended release or delayed release kinetics. For example, the outer coat or layer can act as a barrier that prevents immediate release of the API without inhibiting immediate absorption of the API upon administration.

In some embodiments, the delayed release formulation, when administered to a subject provides a secnidazole concentration profile characterized by a change in secnidazole concentration as function of time that is less than that of an immediate release secnidazole microgranule formulation. In some embodiments, the delayed release formulation, when administered to a subject provides a secnidazole concentration profile characterized by a time to maximum plasma concentration ($T_{max}$) that is greater than that of an immediate release secnidazole microgranule formulation. In some embodiments, the delayed release formulation, when administered to a subject provides a secnidazole concentration profile characterized by a maximum serum concentration ($C_{max}$) that is greater than that of an immediate release secnidazole microgranule formulation. In some embodiments, the delayed release formulation, when administered to a subject provides a secnidazole concentration profile characterized by an area under the curve (AUC) that is greater than that of an immediate release secnidazole microgranule formulation. In some embodiments, the microgranule formulation comprises about 1 g to about 2 g of secnidazole or pharmaceutically acceptable salts thereof. In some embodiments, the microgranule formulation comprises about 2 g of secnidazole or pharmaceutically acceptable salts thereof. In some embodiments, the microgranule formulation is suitable for oral administration. Some embodiments further comprise sugar spheres, povidone, polyethylene glycol 4000, (poly(ethyl acrylate-co-methyl methacrylate) 2:1, with α-(4-nonylphenyl) ω-hydroxypoly-(oxy-1, 2-ethanediyl) (1.5 wt. %) as excipient), sold under the trademark Eudragit NE30D, talc, colloidal silicon dioxide or any combination thereof. In some embodiments, the microgranule formulation further comprises at least one of sugar spheres, povidone, polyethylene glycol 4000, (poly(ethyl acrylate-co-methyl methacrylate) 2:1, with α-(4-nonylphenyl) ω-hydroxypoly-(oxy-1, 2-ethanediyl) (1.5 wt. %) as excipient), sold under the trademark Eudragit NE30D, talc, colloidal silicon dioxide or a combination thereof. Some embodiments further comprise polyethylene glycol 4000 and (poly(ethyl acrylate-co-methyl methacrylate) 2:1, with α-(4-nonylphenyl) ω-hydroxypoly-(oxy-1, 2-ethanediyl) (1.5 wt. %) as excipient), sold under the trademark Eudragit NE30D. In some embodiments, the microgranule formulation comprises a plurality of microgranules. In some embodiments, the plurality of microgranules each have a particle size range of about 400 micrometers to about 841 micrometers.

In some embodiments, the plurality of microgranules has a volume-weighted particle size distribution within a microgranule population, wherein the volume-weighted particle size distribution as measured from a representative sample of the microgranule population includes:
  (a) 10% of the microgranule population has a volume-weighted particle size about no less than 470 micrometers;
  (b) 50% of the microgranule population has a volume-weighted particle size between about no less than 640 micrometers and about no more than 810 micrometers;
  (c) 90% of the microgranule population has a volume-weighted particle size about no more than 1170 micrometers; or
  (d) a combination thereof, which can include some or all (a) through (c) above.

In some embodiments, the taste-masked microgranule formulation displays an in vitro dissolution profile characterized by having a secnidazole release rate that is slower than a secnidazole release rate of a non-taste masked microgranule formulation. For example, the taste-masked microgranule formulation can have an outer layer that inhibits/delays the release of API from the formulation. The secnidazole release rates can be characterized via a dissolution test known in the art. For the purposes of the dissolution testing the microgranule formulations standard methods for determining the dissolution profile are available in the art. Various protocols have been developed for conducting such in-vitro dissolution tests, and are routinely used for both product development and quality assurance. Often, dissolution testing is conducted using recommended compendial methods and apparatus, such as the U.S. Pharmacopoeia (USP) and the European Pharmacopoeia (EP), e.g., USP 28<711> and EP 5.0, 2.9.3. Dissolution profiles are often used by the approving authorities such as FDA and European Medicines Approval Agency (EMEA) for accepting products, waive bioequivalence requirements and support requests for other bioequivalence requirements than the recommended. Dissolution media typically used in such tests are, for example, phosphate buffers, water and citrate buffers. Four different types of dissolution apparatus, based on different stirring methods are commonly available commercially and have compendial recognition. These apparatuses are known as: paddle, basket, flow-through, and reciprocating cylinder. Of the four types of apparatus, the paddle apparatus is the most commonly used. Several standard paddle-type drug dissolution testing apparatuses are known, such as those manufactured by Varian Inc., Distek Inc. and others. While exact protocols and apparatus vary, all drug dissolution test methods involve placing the pharmaceutical product into an aqueous dissolution medium (e.g., water and/or buffers), and applying some form of agitation to the dissolution medium in order to promote disintegration and dissolution of the product under test.

An exemplary and suitable method to determine a dissolution profile of the microgranule formulation in vivo, e.g., in a subject (such as a human) can be after administering a therapeutically effective amount of secnidazole in the microgranule formulation to measure the rate of active material absorption by measuring the plasma concentration of secnidazole over a period of time and comparing the results from the microgranule formulation to a control (e.g., microgranule formulation without secnidazole).

In some embodiments, the in vitro dissolution profile of the taste-masked microgranule formulation is characterized by having no more than about 35% of the secnidazole content released from the microgranule formulation within 30 minutes after starting the dissolution test; by having no less than 55% of the secnidazole content released from the microgranule formulation within 120 minutes after starting a dissolution test, and/or by having no less than 80% of the secnidazole content released from the microgranule formulation with 180 minutes after the starting the dissolution test.

DETAILED DESCRIPTION

Figure 1:
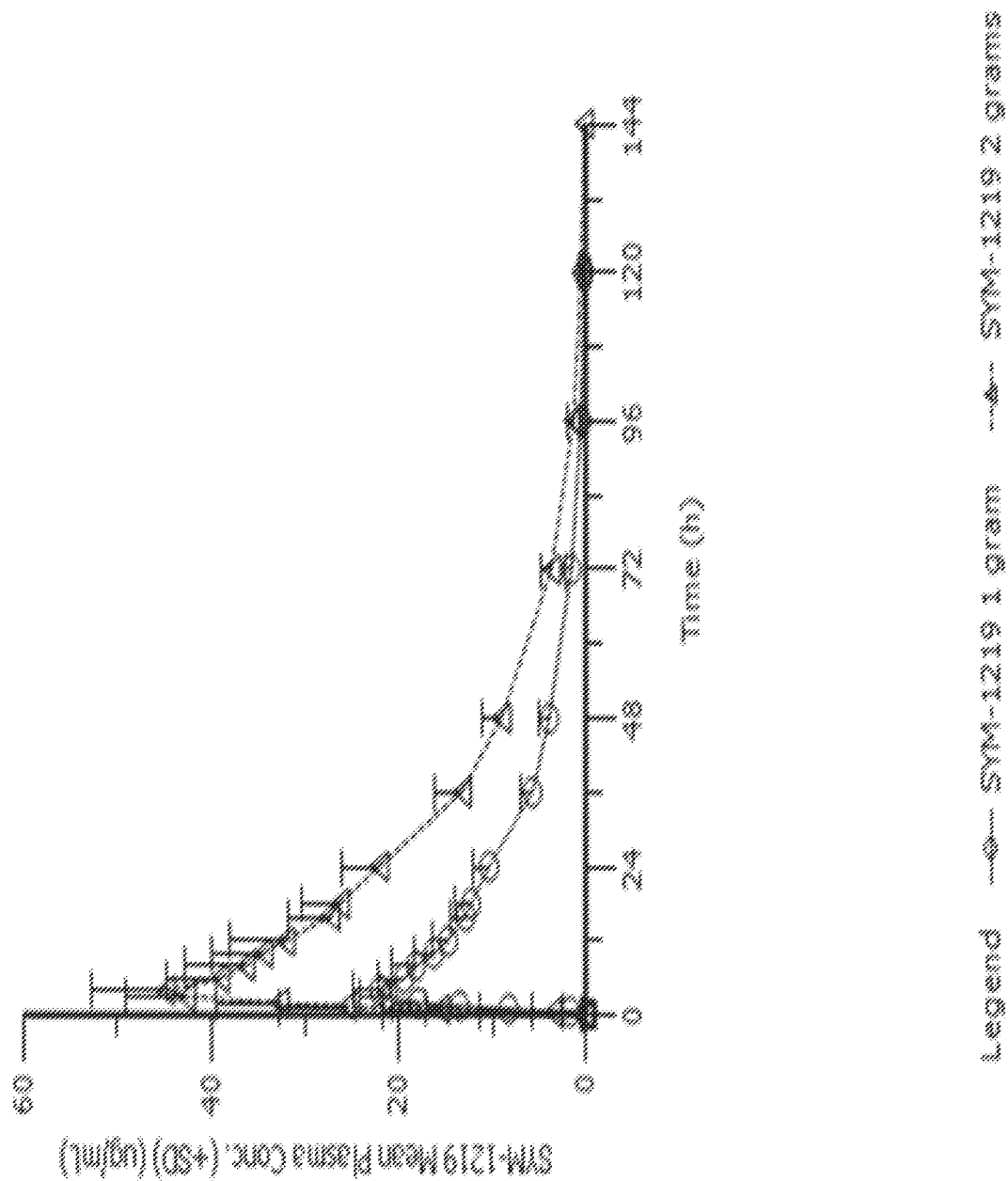
FIG. 1 illustrates the mean (±Standard Deviation (SD)) SYM-1219 plasma concentration (μg/mL) for the 1 g dose (circle markers) and the 2 g dose (triangle markers) over time.

Before the present formulations and methods are described, it is to be understood that this invention is not limited to the particular processes, compounds, or methodologies described, as these may vary. It is also to be understood that the terminology used in the description is for the purpose of describing the particular versions or embodiments only, and is not intended to limit the scope of the present invention. Unless defined otherwise, all technical and scientific terms used herein have the same meanings as commonly understood by one of ordinary skill in the art. Although any methods and materials similar or equivalent to those described herein can be used in the practice or testing of embodiments of the present invention, the preferred methods, devices, and materials are now described. All publications and products mentioned herein are incorporated by reference in their entirety.

Secnidazole [1-(2-hydroxypropyl)-2-methyl-5-nitroimidazole and pharmaceutically acceptable salts thereof; SYM-1219] is a 5-nitroimidazole compound. Embodiments described in this document are directed to secnidazole formulations and the use of a secnidazole formulation for the treatment of bacterial vaginosis.

In some embodiments, the secnidazole formulation comprises a secnidazole microgranule formulation. In some embodiments, the secnidazole microgranule formulation is a delayed release formulation. In some embodiments, a delayed release formulation, when administered to a subject that provides a secnidazole concentration profile characterized by a change in secnidazole concentration as function of time that is less than that of an immediate release secnidazole microgranule formulation. In some embodiments, the secnidazole microgranule formulation comprises about 1 g to about 2 g of secnidazole or pharmaceutically acceptable salts thereof. In some embodiments, the secnidazole microgranule formulation comprises about 2 g of secnidazole or pharmaceutically acceptable salts thereof. In some embodiments, the secnidazole microgranule formulation may be suitable for oral administration. In some embodiments, the secnidazole microgranule formulation can further comprise one or more of the following ingredients selected from at least one inert core (sugar spheres being preferred), at least one binding agents (povidone being preferred), at least one plasticizer (polyethylene glycols being preferred and polyethylene glycol 4000 being most preferred), at least one film-forming polymer (poly(meth)acrylates being preferred and ethyl acrylate/methyl methacrylate copolymer being most preferred), at least one anti tacking agent (talc being preferred), at least one anti-static agent (talc being preferred), and a combination thereof. In some embodiments, the microgranule formulation may further comprise one or more of the following ingredients selected from sugar spheres, povidone, polyethylene glycol 4000, (poly(ethyl acrylate-co-methyl methacrylate) 2:1, with α-(4-nonylphenyl) ω-hydroxypoly-(oxy-1, 2-ethanediyl) (1.5 wt. %) as excipient), sold under the trademark Eudragit NE30D, talc, and colloidal silicon dioxide. In some embodiments, the microgranule formulation may further comprise one or more of the following ingredients selected from sugar spheres, povidone, polyethylene glycol 4000, (poly(ethyl acrylate-co-methyl methacrylate) 2:1, with α-(4-nonylphenyl) ω-hydroxypoly-(oxy-1, 2-ethanediyl) (1.5 wt. %) as excipient), sold under the trademark Eudragit NE30D, and talc. In some embodiments, the secnidazole microgranule formulation comprises a plurality of microgranules. In some embodiments, the plurality of microgranules are white to off-white in color. In some embodiments, the plurality of microgranules each have a particle size range of about 400 micrometers to about 841 micrometers.

In some embodiments, the plurality of microgranules has a volume-weighted particle size distribution within a microgranule population, wherein the volume-weighted particle size distribution as measured from a representative sample of the microgranule population includes:
  (a) 10% of the microgranule population has a volume-weighted particle size about no less than 470 micrometers;
  (b) 50% of the microgranule population has a volume-weighted particle size between about no less than 640 micrometers and about no more than 810 micrometers;
  (c) 90% of the microgranule population has a volume-weighted particle size about no more than 1170 micrometers; or
  (d) a combination thereof, which can include some or all of (a) through (c) above.

In some embodiments, the microgranules are packaged as a unit dose or a single unit dose. A unit dose, also defined as single dose herein, is a dosage in a form that includes therapeutically effective amount of secnidazole in a microgranule formulation. The unit dose could be administered to an individual as a single unit dose wherein the therapeutically effective amount of secnidazole in a microgranule formulation is included in a single package, such as, one pouch, packet, sachet, or bottle. In some embodiments, the microgranules are packaged in such a way as to provide a barrier to oxygen and moisture. In some embodiments, the microgranules are packaged in a foil pouch or sachet. In some embodiments, the foil pouch or sachet is made of a polyester-faced laminated or polyethylene-metallocene-lined aluminum foil pouching material that provides a barrier to oxygen and moisture. In some embodiments, the pouch or sachet is made from a material such as, but not limited to, the polyester-faced laminated pouching material sold under the trademark Fasson® Rapid-Roll® White Cosmetic Web 350 HB. In some embodiments, the microgranule formulation can include a plurality of microgranules comprising inert cores made from microcrystalline cellulose. For example, the inert cores made from microcrystalline cellulose could replace sugar cores. In some embodiments, a composition comprising glycerol monostearate (e.g., water, glycerol monostearate, triethyl citrate, and polysorbase 80, sold [[as]] under the trademark PlasACRYL® T20 by Evonik) can be used as an anti-tacking agent. For example, glycerol monostearate can be used in Eudragit coatings in place of talc.

In some embodiments, a method of making the secnidazole microgranule formulation comprises coating sugar spheres. In some embodiments, the coating is a process, such as a four-step process. In some embodiments, the process comprises layering the secnidazole on the spheres, seal coating with polyethylene glycol 4000, coating with (poly(ethyl acrylate-co-methyl methacrylate) 2:1, with α-(4-nonylphenyl) ω-hydroxypoly-(oxy-1, 2-ethanediyl) (1.5 wt. %) as excipient), sold under the trademark Eudragit NE30D, and curing. In some embodiments, coating with Eudragit provides a delayed release formulation. Other grades of ethyl acrylate-methyl methacrylate copolymer sold under the trademark Eudragit can also be used in the formulations, e.g., Eudragit E (either E 100 or E PO) or Kollicoat SmartSeal. In some embodiments, a method of making the secnidazole microgranule formulation comprises blending with talc. In some embodiments, blending with talc increases the flowability of the secnidazole microgranule formulation.

In some embodiments, a method of making the secnidazole microgranule formulation comprises coating sugar spheres. In some embodiments, the coating is a process, such as a three-step process. In some embodiments, the process comprises layering the secnidazole on the spheres, coating with (poly(ethyl acrylate-co-methyl methacrylate) 2:1, with α-(4-nonylphenyl) ω-hydroxypoly-(oxy-1, 2-ethanediyl) (1.5 wt. %) as excipient), sold under the trademark Eudragit NE30D, and curing. In some embodiments, coating with Eudragit provides a delayed release formulation. In some embodiments, a method of making the secnidazole microgranule formulation comprises blending with talc. In some embodiments, blending with talc increases the flowability of the secnidazole microgranule formulation.

In some embodiments, a method of treating bacterial vaginosis in a subject in need thereof comprises administering to the subject a therapeutically effective amount of secnidazole or pharmaceutically acceptable salts thereof. In some embodiments, a method of treating bacterial vaginosis in a subject in need thereof comprises administering to the subject a therapeutically effective amount of secnidazole or pharmaceutically acceptable salts thereof in a microgranule formulation. In some embodiments, the secnidazole microgranule formulation may be suitable for oral administration. In some embodiments, the secnidazole microgranule formulation comprises a plurality of microgranules. In some embodiments, the plurality of microgranules are white to off-white in color. In some embodiments, the plurality of microgranules each have a particle size range of about 400 micrometers to about 841 micrometers. In some embodiments, the secnidazole microgranule formulation may be mixed, stirred, or otherwise integrated into a food substance. In some embodiments, the food substance may be a liquid, semisolid, or soft food. In some embodiments, the food substance may include, but is not limited to applesauce, pudding, yogurt or the like. In some embodiments, integration of the secnidazole microgranule formulation into a food substance has a taste masking function. In some embodiments, the secnidazole microgranule formulation may be mixed, stirred, or otherwise integrated in a liquid, such as water, juice, milk or the like.

In some embodiments, the plurality of microgranules has a volume-weighted particle size distribution within a microgranule population, wherein the volume-weighted particle size distribution as measured from a representative sample of the microgranule population includes:
  (a) 10% of the microgranule population has a volume-weighted particle size about no less than 470 micrometers;
  (b) 50% of the microgranule population has a volume-weighted particle size between about no less than 640 micrometers and about no more than 810 micrometers;
  (c) 90% of the microgranule population has a volume-weighted particle size about no more than 1170 micrometers; or
  (d) a combination thereof, which can include sore e or all of (a) through (c) above.

In some embodiments, the subject is a human. In yet other embodiments, the subject is a human female. In some embodiments, the human female is of an age ranging from a postmenarachal adolescent to a premenopausal woman. In some embodiments, the subject is a pregnant human female.

In some embodiments, the subject is a female. In some embodiments, the subject is an otherwise healthy female. In some embodiments, the subject is a pregnant female. In some embodiments, the subject is an otherwise healthy pregnant female. In some embodiments, the subject is a female having had 3 or fewer bacterial vaginosis infections in the past 12 months. In some embodiments, the subject is a female having had 4 or more bacterial vaginosis infections in the past twelve months. In some embodiments, the subject is a female with recurring bacterial vaginosis. In some embodiments, a subject with recurring bacterial vaginosis is a subject with 4 or more bacterial vaginosis infections within a twelve-month period. In some embodiments, the subject is a female with frequent bacterial vaginosis infections. In some embodiments, a female with frequent bacterial vaginosis infections is a female with 4 or more bacterial vaginosis infections within a twelve-month period. In some embodiments, the subject is a female presenting with an off-white (milky or gray), thin, homogeneous vaginal discharge, vaginal pH greater than or equal to 4.7, presence of clue cells of greater than or equal to 20% of the total epithelial cells on microscopic examination of a vaginal saline wet mount, a positive 10% KOH Whiff test or a combination thereof. In some embodiments, the subject is a female presenting with an off-white (milky or gray), thin, homogeneous vaginal discharge, vaginal pH greater than or equal to 4.7, the presence of clue cells of greater than or equal to 20% of the total epithelial cells on microscopic examination of a vaginal saline wet mount, and a positive 10% KOH Whiff test. In some embodiments, the subject is a female with confirmed bacterial vaginosis. In some embodiments, bacterial vaginosis is confirmed by the presence of four (4) Amsel criteria parameters selected from an off-white (milky or gray), thin, homogeneous vaginal discharge, vaginal pH greater than or equal to 4.7, the presence of clue cells of greater than or equal to 20% of the total epithelial cells on microscopic examination of a vaginal saline wet mount, a positive 10% KOH Whiff test and a gram stain slide Nugent score equal to, or higher than four (4) on bacterial analysis of vaginal samples. In some embodiments, the subject is a female with suspected bacterial vaginosis. In some embodiments, suspected bacterial vaginosis is indicated by the presence of four (4) Amsel criteria parameters selected from an off-white (milky or gray), thin, homogeneous vaginal discharge, vaginal pH greater than or equal to 4.7, the presence of clue cells of greater than or equal to 20% of the total epithelial cells on microscopic examination of a vaginal saline wet mount, and a positive 10% KOH Whiff test. In some embodiments, the subject is a female presenting with an off-white (milky or gray), thin, homogeneous vaginal discharge, odor, or a combination thereof.

In some embodiments, a method of treating bacterial vaginosis in a subject comprises administering to the subject a single dose of a therapeutically effective amount of secnidazole in a microgranule formulation, wherein the secnidazole comprises about 1 g to about 2 g of the microgranule formulation. In some embodiments, the secnidazole microgranule formulation is co-administered with an additional compound selected from ethinyl estradiol (EE2), norethindrone (NET), or a combination thereof. In some embodiments, the secnidazole microgranule formulation is mixed into a liquid, semisolid or soft food substance, such as but not limited to applesauce yogurt and pudding. In some embodiments, the amount of the food substance is about 4-6 ounces. In some embodiments, the secnidazole microgranule formulation is mixed into a liquid, such as water, juice or the like.

In some embodiments, a method of treating bacterial vaginosis in a subject comprises administering to the subject a single dose of a secnidazole microgranule formulation that exhibits a maximum serum concentration ($C_{max}$) of between about 34.5 µg/ml and about 58.3 µg/ml. In some embodiments, a method of treating bacterial vaginosis in a subject comprises administering to the subject a single dose of a secnidazole microgranule formulation that exhibits a maximum serum concentration ($C_{max}$) of between about 17.4 µg/ml and about 26.5 µg/ml.

In some embodiments, a method of treating bacterial vaginosis in a subject comprises administering to the subject a single dose of a secnidazole microgranule formulation that exhibits a time to maximum plasma concentration ($T_{max}$) of about 3 hours to about 4.05 hours. In some embodiments, a method of treating bacterial vaginosis in a subject comprises administering to the subject a single dose of a secnidazole microgranule formulation that exhibits a time to maximum plasma concentration ($T_{max}$) of about 2 hours to about 6 hours.

In some embodiments, a method of treating bacterial vaginosis in a subject comprises co-administering to the subject a single dose of a therapeutically effective amount of secnidazole in a microgranule formulation and an additional compound selected from ethinyl estradiol (EE2), norethindrone (NET), or a combination thereof, wherein the secnidazole comprises about 1 g to about 2 g of the microgranule formulation. In some embodiments, the additional compound is co-administered on the same day as the secnidazole microgranule formulation. In some embodiments, the additional compound is administered on a different day than the secnidazole microgranule formulation. In some embodiments, the secnidazole microgranule formulation does not affect the contraceptive efficacy of the additional compound.

In some embodiments, a method of treating bacterial vaginosis in a subject further comprises determining a post treatment clinical outcome. In some embodiments, a post treatment clinical outcome is indicative of a clinical outcome responder. Some embodiments further comprise determining a post-treatment clinical outcome. In some embodiments, a post-treatment clinical outcome of clinical cure is defined as a clinical outcome responder. In some embodiments, a clinical outcome responder is a subject with normal vaginal discharge, a negative KOH Whiff test, and clue cells less than or equal to 20% of the total epithelial cells on microscopic examination of a vaginal saline wet mount after treatment with a microgranule formulation comprising about 1 grams to about 2 grams of secnidazole. In some embodiments, a clinical outcome responder has a gram stain slide Nugent score of less than four (4) after treatment with a single dose of secnidazole. In yet other embodiments, a clinical outcome responder is a subject with normal vaginal discharge, a negative KOH Whiff test, clue cells less than 20% of total epithelial cells, and a gram stain slide Nugent score of less than four (4) after treatment with a single dose of secnidazole. In some embodiments, a clinical outcome responder has a gram stain slide Nugent score of less than four (4) after treatment with a 2 gram single dose of secnidazole. In yet other embodiments, a clinical outcome responder is a subject with normal vaginal discharge, a negative KOH Whiff test, clue cells less than 20% of total epithelial cells, and a gram stain slide Nugent score of less than four (4) after treatment with a 2 gram single dose of secnidazole. In some embodiments, a post-treatment clinical outcome is observable after about 24 hours after administration. In some embodiments, a post-treatment clinical outcome is observable after about 48 hours after administration. In some embodiments, a post-treatment clinical outcome is observable after about 72 hours after administration. In some embodiments, a post-treatment clinical outcome is observable after about 96 hours after administration. In some embodiments, a post-treatment clinical outcome is observable after about 120 hours after administration. In some embodiments, a post-treatment clinical outcome is observable after about 168 hours after administration. In some embodiments, a post-treatment clinical outcome is observable after about 7 days to about 10 days after administration. In some embodiments, a post-treatment clinical outcome is observable after about 11 days to about 20 days after administration. In some embodiments, a post-treatment clinical outcome is observable after about 21 days to about 30 days after administration.

In some embodiments, a method of treating bacterial vaginosis further comprises an alleviation of one or more symptoms of bacterial vaginosis within up to about three days after administration to the subject. In some embodiments, a method of treating bacterial vaginosis further comprises an alleviation of one or more symptoms of bacterial vaginosis within up to about three days after administration to the subject. In some embodiments, the one or more symptoms include, but are not limited to, abnormal vaginal odor, abnormal vaginal discharge or a combination thereof. In some embodiments, alleviation refers to a lessening of the severity of one or more symptoms. In some embodiments, alleviation of one or more symptoms of bacterial vaginosis occurs within about 24 hours after administration. In some embodiments, alleviation of one or more symptoms of bacterial vaginosis occurs within about 48 hours after administration. In some embodiments, alleviation of one or more symptoms of bacterial vaginosis occurs within about 72 hours after administration to the subject. In some embodiments, alleviation of one or more symptoms of bacterial vaginosis occurs within about 96 hours after administration to the subject. In some embodiments, alleviation of one or more symptoms of bacterial vaginosis occurs within about 120 hours after administration to the subject. In some embodiments, alleviation of one or more symptoms of bacterial vaginosis occurs within about 168 hours after administration to the subject. In some embodiments, alleviation of one or more symptoms of bacterial vaginosis occurs within about 7 days to about 10 days after administration to the subject. In some embodiments, alleviation of one or more symptoms of bacterial vaginosis occurs within about 11 days to about 20 days after administration to the subject. In some embodiments, alleviation of one or more symptoms of bacterial vaginosis occurs within about 21 days to about 30 days after administration to the subject.

In some embodiments, a method of treating bacterial vaginosis further comprises a resolution of one or more symptoms of bacterial vaginosis within up to about seven days after administration to the subject. In some embodiments, a method of treating bacterial vaginosis further comprises a resolution of one or more symptoms of bacterial vaginosis within up to about seven days after administration to the subject. In some embodiments, the one or more symptoms include, but are not limited to, abnormal vaginal odor, abnormal vaginal discharge or a combination thereof. In some embodiments, resolution of one or more symptoms of bacterial vaginosis occurs within about 24 hours after administration to the subject. In some embodiments, resolution of one or more symptoms of bacterial vaginosis occurs within about 48 hours after administration. In some embodiments, resolution of one or more symptoms of bacterial vaginosis occurs within about 72 hours after administration to the subject. In some embodiments, resolution of one or more symptoms of bacterial vaginosis occurs within about 96 hours after administration to the subject. In some embodiments, resolution of one or more symptoms of bacterial vaginosis occurs within about 120 hours after administration to the subject. In some embodiments, resolution of one or more symptoms of bacterial vaginosis occurs within about 168 hours after administration to the subject. In some embodiments, resolution of one or more symptoms of bacterial vaginosis occurs within about 7 days to about 10 days after administration to the subject. In some embodiments, resolution of one or more symptoms of bacterial vaginosis occurs within about 11 days to about 20 days after administration to the subject. In some embodiments, resolution of one or more symptoms of bacterial vaginosis occurs within about 21 days to about 30 days after administration to the subject.

In some embodiments, treatment of bacterial vaginosis with a single, 2 gram dose of secnidazole in a microgranule formulation results in better than expected efficacy compared with FDA approved drugs used in the treatment of bacterial vaginosis. In some embodiments, treatment of bacterial vaginosis with a single, 2 gram dose of secnidazole in a microgranule formulation results in superior effectiveness compared with other FDA-approved drugs used in the treatment of bacterial vaginosis. In some embodiments, treatment of bacterial vaginosis with a single, 2 gram dose of secnidazole in a microgranule formulation results in a higher rate of clinical cure than FDA-approved drugs used in the treatment of bacterial vaginosis. In some embodiments, a clinical outcome responder is a subject with normal vaginal discharge, a negative KOH Whiff test, and clue cells less than or equal to 20% of the total epithelial cells on microscopic examination of a vaginal saline wet mount after treatment. In some embodiments, a single dose of 2 grams of secnidazole results in a better than expected efficacy compared with FDA approved drugs currently used in the treatment of bacterial vaginosis. In some embodiments, treatment of bacterial vaginosis with a single, 2 gram dose of secnidazole results in superior efficacy compared with FDA approved drugs used in the treatment of bacterial vaginosis. In some embodiments, a single dose of 2 grams of secnidazole results in superior efficacy compared with FDA drugs used in the treatment of bacterial vaginosis requiring multiple doses during treatment. For example, Secnidazole has been shown to have a higher rate of clinical cure after 21-30 days of treatment (67.7% clinical cure after a single, 2 g oral dose) compared with other FDA approved drugs for the treatment of bacterial vaginosis (Nuvessa—37% after vaginal single application; Tindamax—35.6% after 3 day oral regimen and 51.3% after 5 day oral regimen; Clindesse—41.0-53.45 clinical cure after vaginal single application; Flagyl ER—61.1-62.2% clinical cure after 7 day oral regimen; and Metrogel-Vaginal—53.0% after 5 day vaginal regimen (all clinical cure rates are 21-30 days after treatment)).

In some embodiments, treatment of bacterial vaginosis with a single, 2 gram dose of secnidazole results in a better than expected safety profile compared with FDA approved drugs used in the treatment of bacterial vaginosis. In some embodiments, a single dose of 2 grams of secnidazole results in a better than expected safety profile compared with FDA approved drugs used in the treatment of bacterial vaginosis requiring multiple doses during treatment. In some embodiments, treatment of bacterial vaginosis with a single, 2 gram dose of secnidazole results in a superior safety profile compared with FDA approved drugs used in the treatment of bacterial vaginosis. In some embodiments, a single dose of 2 grams of secnidazole results in a superior safety profile compared with FDA approved drugs used in the treatment of bacterial vaginosis requiring multiple doses during treatment. In some embodiments, treatment of bacterial vaginosis with a single, 2 gram dose of secnidazole in a microgranule formulation results in a better than expected safety profile compared with FDA approved drugs used in the treatment of bacterial vaginosis. In some embodiments, a single dose of 2 grams of secnidazole in a microgranule formulation results in a better than expected safety profile compared with FDA approved drugs used in the treatment of bacterial vaginosis requiring multiple doses during treatment. In some embodiments, treatment of bacterial vaginosis with a single, 2 gram dose of secnidazole in a microgranule formulation results in a superior safety profile compared with FDA approved drugs used in the treatment of bacterial vaginosis. In some embodiments, a single dose of 2 grams of secnidazole in a microgranule formulation results in a superior safety profile compared with FDA approved drugs used in the treatment of bacterial vaginosis requiring multiple doses during treatment. In some embodiments, multiple doses may be given at pre-determined intervals such as but not limited to once a week, bi-weekly, monthly, bimonthly for the duration of treatment. In some embodiment, the duration of treatment may be at least one week. In some embodiment, the duration of treatment may be at least one month. In some embodiments, the duration of treatment is about six months. For example, as can be seen in Table 1, secnidazole has superior safety profile compared with other FDA approved drugs for the treatment of bacterial vaginosis.

TABLE 1

Comparison of key adverse events

| Adverse Event | Secnidazole 2 grams (n = 72) | Flagyl ER (N = 267) | Clindesse (n = 368) | Metrogel-Vaginal (n = 505) |
| --- | --- | --- | --- | --- |
| Headache | 1% | 18% | 3% | 5% |
| Nausea | 1% | 10% | 1% | 4% |
| Abdominal pain | 0% | 4% | 1% | Not reported |
| Diarrhea | 0% | 4% | 1% | 1% |
| Metallic/Unusual Taste | 1% | 9% | Not reported | 2% |
| Fungal Infection | 3% | Not reported | 14% | 10% |
| Vulva/Vaginal Irritation | 1% | Not reported | 3% | 9% |

In some embodiments, treatment of bacterial vaginosis with a single, 2 gram dose of secnidazole results in better than expected efficacy compared with FDA approved drugs used in the treatment of bacterial vaginosis in subjects with frequent bacterial vaginosis infections. In some embodiments, a single dose of 2 grams of secnidazole results in a better than expected efficacy compared with FDA approved drugs used in the treatment of bacterial vaginosis requiring multiple doses during treatment in subjects with frequent bacterial vaginosis infections. In some embodiments, treatment of bacterial vaginosis with a single, 2 gram dose of secnidazole results in superior efficacy compared with FDA approved drugs used in the treatment of bacterial vaginosis in subjects with frequent bacterial vaginosis infections. In some embodiments, a single dose of 2 grams of secnidazole results in superior efficacy compared with FDA approved drugs used in the treatment of bacterial vaginosis requiring multiple doses during treatment in subjects with frequent bacterial vaginosis infections. In some embodiments, subjects with frequent bacterial vaginosis infections are subjects with 4 or more bacterial vaginosis infections within a twelve-month period.

In some embodiments, treatment of bacterial vaginosis with a single, 2 gram dose of secnidazole results in better than expected safety profile compared with FDA approved drugs used in the treatment of bacterial vaginosis with frequent bacterial vaginosis infections. In some embodiments, a single dose of 2 grams of secnidazole results in a better than expected safety profile compared with FDA approved drugs used in the treatment of bacterial vaginosis requiring multiple doses during treatment in subjects with frequent bacterial vaginosis infections. In some embodiments, treatment of bacterial vaginosis with a single, 2 gram dose of secnidazole results in a superior safety profile compared with FDA approved drugs used in the treatment of bacterial vaginosis in subjects with frequent bacterial vaginosis infections. In some embodiments, a single dose of 2 grams of secnidazole results in a superior safety profile compared with FDA approved drugs used in the treatment of bacterial vaginosis requiring multiple doses during treatment in subjects with frequent bacterial vaginosis infections. In some embodiments, subjects with frequent bacterial vaginosis infections are those with 4 or more bacterial vaginosis infections within a twelve-month period.

In some embodiments, a method of treating bacterial vaginosis in a subject in need thereof further comprises administering to at least one of the subjects' sexual partners, a therapeutically effective amount of secnidazole or pharmaceutically acceptable salts thereof. In some embodiments, a method of treating bacterial vaginosis in a subject in need thereof further comprises administering to at least one of the subjects' sexual partners, a therapeutically effective amount of secnidazole or pharmaceutically acceptable salts thereof in a microgranule formulation. In some embodiments, the secnidazole microgranule formulation may be suitable for oral administration. In some embodiments, the secnidazole microgranule formulation comprises a plurality of microgranules. In some embodiments, the plurality of microgranules are white to off-white in color. In some embodiments, the plurality of microgranules each have a particle size range of about 400 micrometers to about 841 micrometers. In some embodiments, the secnidazole microgranule formulation may be mixed, stirred, or otherwise integrated into a food substance. In some embodiments, the food substance may be a liquid, semisolid, or soft food. In some embodiments, the food substance may include, but is not limited to applesauce, pudding, yogurt or the like. In some embodiments, integration of the secnidazole microgranule formulation into a food substance has a taste masking function. In some embodiments, the secnidazole microgranule formulation may be mixed, stirred, or otherwise integrated in a liquid, such as water, juice, milk or the like. In some embodiments, the at least one sexual partner of the subject may be a male or a female. In some embodiments, a single dose of a therapeutically effective amount of secnidazole or pharmaceutically acceptable salts thereof may be administered. In some embodiments, a single dose of a therapeutically effective amount of secnidazole or pharmaceutically acceptable salts thereof in a microgranule formulation may be administered. In some embodiments, multiple doses may be given at pre-determined intervals such as but not limited to once a week, bi-weekly, monthly, bimonthly for the duration of treatment. In some embodiment, the duration of treatment may be at least one week. In some embodiment, the duration of treatment may be at least one month. In some embodiments, the duration of treatment is about six months.

In some embodiments, the plurality of microgranules has a volume-weighted particle size distribution within a microgranule population, wherein the volume-weighted particle size distribution as measured from a representative sample of the microgranule population includes:
(a) 100 of the microgranule population has a volume-weighted particle size about no less than 470 micrometers;
(b) 50% of the microgranule population has a volume-weighted particle size between about no less than 640 micrometers and about no more than 810 micrometers;
(c) 90% of the microgranule population has a volume-weighted particle size abort no more than 1170 micrometers; or
(d) a combination thereof, which can include some or A of (a) through (c) above.

Some embodiments are directed to a method of reducing the incidence and/or risk of a preterm birth. Bacterial vaginosis infections may increase the risk of a preterm birth in a subject. In some embodiments, a method of reducing the incidence and/or risk of a preterm birth in a subject comprises administering to the subject a therapeutically effective amount of secnidazole or pharmaceutically acceptable salts thereof. In some embodiments, a method of reducing the incidence and/or risk of a preterm birth in a subject comprises administering to the subject a therapeutically effective amount of secnidazole or pharmaceutically acceptable salts thereof in a microgranule formulation. In some embodiments, the secnidazole microgranule formulation may be suitable for oral administration. In some embodiments, the secnidazole microgranule formulation comprises a plurality of microgranules. In some embodiments, the plurality of microgranules are white to off-white in color. In some embodiments, the plurality of microgranules each have a particle size range of about 400 micrometers to about 841 micrometers. In some embodiments, the secnidazole microgranule formulation may be mixed, stirred, or otherwise integrated into a food substance. In some embodiments, the food substance may be a liquid, semisolid or soft food. In some embodiments, the food substance may include, but is not limited to applesauce, pudding, yogurt or the like. In some embodiments, integration of the secnidazole microgranule formulation into a food substance has a taste masking function. In some embodiments, the secnidazole microgranule formulation may be mixed, stirred, or otherwise integrated in a liquid, such as water, juice, milk or the like. In some embodiments, the subject is a human. In yet other embodiments, the subject is a pregnant human female.

In some embodiments, the plurality of microgranules has a volume-weighted particle size distribution within a microgranule population, wherein the volume-weighted particle size distribution as measured from a representative sample of the microgranule population includes:
(a) 10% of the microgranule population has a volume-weighted particle size about no less than 470 micrometers;
(b) 50% of the microgranule population has a volume-weighted particle size between about no less than 640 micrometers and about no more than 810 micrometers;

(c) 90% of the microgranule population has a volume-weighted particle size about no more than 1170 micrometers; or (d) a combination thereof, which can include some or all of (a) through (c) above.

In some embodiments, the subject is a female. In some embodiments, the subject is an otherwise healthy female. In some embodiments, the subject is a pregnant female. In some embodiments, the subject is an otherwise healthy pregnant female. In some embodiments, the subject is a female having had 3 or fewer bacterial vaginosis infections in the past 12 months. In some embodiments, the subject is a female having had 4 or more bacterial vaginosis infections in the past twelve months. In some embodiments, the subject is a female with recurring bacterial vaginosis. In some embodiments, a subject with recurring bacterial vaginosis is a subject with 4 or more bacterial vaginosis infections within a twelve-month period. In some embodiments, the subject is a female with frequent bacterial vaginosis infections. In some embodiments, a female with frequent bacterial vaginosis infections is a female with 4 or more bacterial vaginosis infections within a twelve-month period. In some embodiments, the subject is a female presenting with an off-white (milky or gray), thin, homogeneous vaginal discharge, vaginal pH greater than or equal to 4.7, presence of clue cells of greater than or equal to 20% of the total epithelial cells on microscopic examination of a vaginal saline wet mount, a positive 10% KOH Whiff test or a combination thereof. In some embodiments, the subject is a female presenting with an off-white (milky or gray), thin, homogeneous vaginal discharge, vaginal pH greater than or equal to 4.7, the presence of clue cells of greater than or equal to 20% of the total epithelial cells on microscopic examination of a vaginal saline wet mount, and a positive 10% KOH Whiff test. In some embodiments, the subject is a female with confirmed bacterial vaginosis. In some embodiments, bacterial vaginosis is confirmed by the presence of four (4) Amsel criteria parameters selected from an off-white (milky or gray), thin, homogeneous vaginal discharge, vaginal pH greater than or equal to 4.7, the presence of clue cells of greater than or equal to 20% of the total epithelial cells on microscopic examination of a vaginal saline wet mount, a positive 10% KOH Whiff test and a gram stain slide Nugent score equal to, or higher than four (4) on bacterial analysis of vaginal samples. In some embodiments, the subject is a female with suspected bacterial vaginosis. In some embodiments, suspected bacterial vaginosis is indicated by the presence of four (4) Amsel criteria parameters selected from an off-white (milky or gray), thin, homogeneous vaginal discharge, vaginal pH greater than or equal to 4.7, the presence of clue cells of greater than or equal to 20% of the total epithelial cells on microscopic examination of a vaginal saline wet mount, and a positive 10% KOH Whiff test. In some embodiments, the subject is a female presenting with an off-white (milky or gray), thin, homogeneous vaginal discharge, odor, or a combination thereof.

In some embodiments, a method of reducing the incidence and/or risk of a preterm birth in a subject comprises administering to the subject a single dose of a therapeutically effective amount of secnidazole in a microgranule formulation, wherein the secnidazole comprises about 1 g to about 2 g of the microgranule formulation. In some embodiments, the secnidazole microgranule formulation is co-administered with an additional compound selected from ethinyl estradiol (EE2), norethindrone (NET), or a combination thereof. In some embodiments, the secnidazole microgranule formulation is mixed into a liquid, semisolid, or soft food substance, such as but not limited to applesauce yogurt and pudding. In some embodiments, the amount of the food substance is about 4-6 ounces. In some embodiments, the secnidazole microgranule formulation may be mixed, stirred, or otherwise integrated in a liquid, such as water, juice, milk or the like. In an embodiment, a unit dose of secnidazole microgranule formulation is mixed, stirred, or otherwise integrated into about 50 ml to about 250 ml of liquid. In another embodiment, the unit dose of secnidazole microgranule formulation is mixed, stirred, or otherwise integrated into about 50 ml, about 60 ml, about 70 ml, about 80 ml, about 90 ml, about 100 ml, about 110 ml, about 120 ml, about 130 ml, about 140 ml, about 150 ml, about 160 ml, about 170 ml, about 180 ml, about 190 ml, about 200 ml, about 210 ml, about 220 ml, about 230 ml, about 240 ml, or about 250 ml of liquid.

In some embodiments, a method of reducing the incidence and/or risk of a preterm birth in a subject comprises administering to the subject a single dose of a secnidazole microgranule formulation that exhibits a maximum serum concentration ($C_{max}$) of between about 34.5 µg/ml and about 58.3 µg/ml. In some embodiments, a method of treating bacterial vaginosis in a subject comprises administering to the subject a single dose of a secnidazole microgranule formulation that exhibits a maximum serum concentration ($C_{max}$) of between about 17.4 µg/ml and about 26.5 µg/ml.

In some embodiments, a method of reducing the incidence and/or risk of a preterm birth in a subject comprises administering to the subject a single dose of a secnidazole microgranule formulation that exhibits a time to maximum plasma concentration ($T_{max}$) of about 3 hours to about 4.05 hours. In some embodiments, a method of treating bacterial vaginosis in a subject comprises administering to the subject a single dose of a secnidazole microgranule formulation that exhibits a time to maximum plasma concentration ($T_{max}$) of about 2 hours to about 6 hours.

In some embodiments, a method of reducing the incidence and/or risk of a preterm birth in a subject further comprises a term birth. In some embodiments, a method of reducing the incidence and/or risk of a preterm birth in a subject further comprises determining a post treatment clinical outcome. In some embodiments, a post treatment clinical outcome is indicative of a clinical outcome responder. Some embodiments further comprise determining a post-treatment clinical outcome. In some embodiments, a post-treatment clinical outcome of clinical cure is defined as a clinical outcome responder. In some embodiments, a clinical outcome responder is a subject with normal vaginal discharge, a negative KOH Whiff test, and clue cells less than or equal to 20% of the total epithelial cells on microscopic examination of a vaginal saline wet mount after treatment with a microgranule formulation comprising about 1 grams to about 2 grams of secnidazole. In some embodiments, a clinical outcome responder has a gram stain slide Nugent score of less than four (4) after treatment with a single dose of secnidazole. In yet other embodiments, a clinical outcome responder is a subject with normal vaginal discharge, a negative KOH Whiff test, clue cells less than 20% of total epithelial cells, and a gram stain slide Nugent score of less than four (4) after treatment with a single dose of secnidazole. In some embodiments, a clinical outcome responder has a gram stain slide Nugent score of less than four (4) after treatment with a 2 gram single dose of secnidazole. In yet other embodiments, a clinical outcome responder is a subject with normal vaginal discharge, a negative KOH Whiff test, clue cells less than 20% of total epithelial cells, and a gram stain slide Nugent score of less than four (4) after treatment with a 2 gram single dose of secnidazole. In some embodiments, a post-treatment clinical outcome is observable after about 24 hours after administration. In some embodiments, a post-treatment clinical outcome is observable after about 48 hours after administration. In some embodiments, a post-treatment clinical outcome is observable after about 72 hours after administration. In some embodiments, a post-treatment clinical outcome is observable after about 96 hours after administration. In some embodiments, a post-treatment clinical outcome is observable after about 120 hours after administration. In some embodiments, a post-treatment clinical outcome is observable after about 168 hours after administration. In some embodiments, a post-treatment clinical outcome is observable after about 7 days to about 10 days after administration. In some embodiments, a post-treatment clinical outcome is observable after about 11 days to about 20 days after administration. In some embodiments, a post-treatment clinical outcome is observable after about 21 days to about 30 days after administration.

In some embodiments, a method of reducing the incidence and/or risk of a preterm birth in a subject further comprises an alleviation of one or more symptoms of bacterial vaginosis within up to about three days after administration to the subject. In some embodiments, a method of treating bacterial vaginosis further comprises an alleviation of one or more symptoms of bacterial vaginosis within up to about three days after administration to the subject. In some embodiments, the one or more symptoms include, but are not limited to, abnormal vaginal odor, abnormal vaginal discharge or a combination thereof. In some embodiments, alleviation refers to a lessening of the severity of one or more symptoms. In some embodiments, alleviation of one or more symptoms of bacterial vaginosis occurs within about 24 hours after administration. In some embodiments, alleviation of one or more symptoms of bacterial vaginosis occurs within about 48 hours after administration. In some embodiments, alleviation of one or more symptoms of bacterial vaginosis occurs within about 72 hours after administration to the subject. In some embodiments, alleviation of one or more symptoms of bacterial vaginosis occurs within about 96 hours after administration to the subject. In some embodiments, alleviation of one or more symptoms of bacterial vaginosis occurs within about 120 hours after administration to the subject. In some embodiments, alleviation of one or more symptoms of bacterial vaginosis occurs within about 168 hours after administration to the subject. In some embodiments, alleviation of one or more symptoms of bacterial vaginosis occurs within about 7 days to about 10 days after administration to the subject. In some embodiments, alleviation of one or more symptoms of bacterial vaginosis occurs within about 11 days to about 20 days after administration to the subject. In some embodiments, alleviation of one or more symptoms of bacterial vaginosis occurs within about 21 days to about 30 days after administration to the subject.

In some embodiments, a method of reducing the incidence and/or risk of a preterm birth in a subject further comprises a resolution of one or more symptoms of bacterial vaginosis within up to about seven days after administration to the subject. In some embodiments, a method of treating bacterial vaginosis further comprises a resolution of one or more symptoms of bacterial vaginosis within up to about seven days after administration to the subject. In some embodiments, the one or more symptoms include, but are not limited to, abnormal vaginal odor, abnormal vaginal discharge or a combination thereof. In some embodiments, resolution of one or more symptoms of bacterial vaginosis occurs within about 24 hours after administration to the subject. In some embodiments, resolution of one or more symptoms of bacterial vaginosis occurs within about 48 hours after administration. In some embodiments, resolution of one or more symptoms of bacterial vaginosis occurs within about 72 hours after administration to the subject. In some embodiments, resolution of one or more symptoms of bacterial vaginosis occurs within about 96 hours after administration to the subject. In some embodiments, resolution of one or more symptoms of bacterial vaginosis occurs within about 120 hours after administration to the subject. In some embodiments, resolution of one or more symptoms of bacterial vaginosis occurs within about 168 hours after administration to the subject. In some embodiments, resolution of one or more symptoms of bacterial vaginosis occurs within about 7 days to about 10 days after administration to the subject. In some embodiments, resolution of one or more symptoms of bacterial vaginosis occurs within about 11 days to about 20 days after administration to the subject. In some embodiments, resolution of one or more symptoms of bacterial vaginosis occurs within about 21 days to about 30 days after administration to the subject.

Some embodiments are directed to a method of reducing the incidence and/or risk of a subject transmitting human immunodeficiency virus (HIV) to a sexual partner. Bacterial vaginosis infections may increase the risk of a HIV transmission to sexual partner. In some embodiments, a method of reducing the incidence and/or risk of the subject transmitting HIV to a sexual partner in a subject comprises administering to the subject a therapeutically effective amount of secnidazole or pharmaceutically acceptable salts thereof. In some embodiments, a method of reducing the incidence and/or risk of a preterm birth in a subject comprises administering to the subject a therapeutically effective amount of secnidazole or pharmaceutically acceptable salts thereof in a microgranule formulation. In some embodiments, the secnidazole microgranule formulation may be suitable for oral administration. In some embodiments, the secnidazole microgranule formulation comprises a plurality of microgranules. In some embodiments, the plurality of microgranules are white to off-white in color. In some embodiments, the plurality of microgranules each have a particle size range of about 400 micrometers to about 841 micrometers In some embodiments, the plurality of microgranules has a volume-weighted particle size distribution within a microgranule population, wherein the volume-weighted particle size distribution as measured from a representative sample of the microgranule population includes:
  (a) 10% of the microgranule population has a volume-weighted particle size about no less than 470 micrometers;
  (b) 50% of the microgranule population has a volume-weighted particle size between about no less than 640 micrometers and about no more than 810 micrometers;
  (c) 90% of the microgranule population has a volume-weighted particle size about no more than 1170 micrometers; or
  (d) a combination thereof, which can include some or all of (a) through (c) above.

In some embodiments, the secnidazole microgranule formulation may be mixed, stirred, or otherwise integrated into a food substance. In some embodiments, the food substance may be a liquid, semisolid, or soft food. In some embodiments, the food substance may include, but is not limited to applesauce, pudding, yogurt or the like. In some embodiments, integration of the secnidazole microgranule formulation into a food substance has a taste masking function. In some embodiments, the secnidazole microgranule formulation may be mixed, stirred, or otherwise integrated in a liquid, such as water, juice, milk or the like.

In some embodiments, the subject is a human female. In some embodiments, the subject is a female. In some embodiments, the subject is an otherwise healthy female. In some embodiments, the subject is a female with HIV. In some embodiments, the subject is an otherwise healthy pregnant female. In some embodiments, the subject is a female having had 3 or fewer bacterial vaginosis infections in the past 12 months. In some embodiments, the subject is a female having had 4 or more bacterial vaginosis infections in the past twelve months. In some embodiments, the subject is a female with recurring bacterial vaginosis. In some embodiments, a subject with recurring bacterial vaginosis is a subject with 4 or more bacterial vaginosis infections within a twelve-month period. In some embodiments, the subject is a female with frequent bacterial vaginosis infections. In some embodiments, a female with frequent bacterial vaginosis infections is a female with 4 or more bacterial vaginosis infections within a twelve-month period. In some embodiments, the subject is a female presenting with an off-white (milky or gray), thin, homogeneous vaginal discharge, vaginal pH greater than or equal to 4.7, presence of clue cells of greater than or equal to 20% of the total epithelial cells on microscopic examination of a vaginal saline wet mount, a positive 10% KOH Whiff test or a combination thereof. In some embodiments, the subject is a female presenting with an off-white (milky or gray), thin, homogeneous vaginal discharge, vaginal pH greater than or equal to 4.7, the presence of clue cells of greater than or equal to 20% of the total epithelial cells on microscopic examination of a vaginal saline wet mount, and a positive 10% KOH Whiff test. In some embodiments, the subject is a female with confirmed bacterial vaginosis. In some embodiments, bacterial vaginosis is confirmed by the presence of four (4) Amsel criteria parameters selected from an off-white (milky or gray), thin, homogeneous vaginal discharge, vaginal pH greater than or equal to 4.7, the presence of clue cells of greater than or equal to 20% of the total epithelial cells on microscopic examination of a vaginal saline wet mount, a positive 10% KOH Whiff test and a gram stain slide Nugent score equal to, or higher than four (4) on bacterial analysis of vaginal samples. In some embodiments, the subject is a female with suspected bacterial vaginosis. In some embodiments, suspected bacterial vaginosis is indicated by the presence of four (4) Amsel criteria parameters selected from an off-white (milky or gray), thin, homogeneous vaginal discharge, vaginal pH greater than or equal to 4.7, the presence of clue cells of greater than or equal to 20% of the total epithelial cells on microscopic examination of a vaginal saline wet mount, and a positive 10% KOH Whiff test. In some embodiments, the subject is a female presenting with an off-white (milky or gray), thin, homogeneous vaginal discharge, odor, or a combination thereof.

In some embodiments, a method of reducing the incidence and/or risk of a subject transmitting HIV to a sexual partner in a subject comprises administering to the subject a single dose of a therapeutically effective amount of secnidazole in a microgranule formulation, wherein the secnidazole comprises about 1 g to about 2 g of the microgranule formulation. In some embodiments, the secnidazole microgranule formulation is co-administered with an additional compound selected from ethinyl estradiol (EE2), norethindrone (NET), or a combination thereof. In some embodiments, the secnidazole microgranule formulation is mixed into a liquid, semisolid or soft food substance, such as but not limited to applesauce yogurt and pudding. In some embodiments, the amount of the food substance is about 4-6 ounces. In some embodiments, the secnidazole microgranule formulation may be mixed, stirred, or otherwise integrated in a liquid, such as water, juice, milk or the like.

In some embodiments, a method of reducing the incidence and/or risk of a subject transmitting HIV to a sexual partner in a subject comprises administering to the subject a single dose of a secnidazole microgranule formulation that exhibits a maximum serum concentration ($C_{max}$) of between about 34.5 µg/ml and about 58.3 µg/ml. In some embodiments, a method of treating bacterial vaginosis in a subject comprises administering to the subject a single dose of a secnidazole microgranule formulation that exhibits a maximum serum concentration ($C_{max}$) of between about 17.4 µg/ml and about 26.5 µg/ml.

In some embodiments, a method of reducing the incidence and/or risk of a subject transmitting HIV to a sexual partner in a subject comprises administering to the subject a single dose of a secnidazole microgranule formulation that exhibits a time to maximum plasma concentration ($T_{max}$) of about 3 hours to about 4.05 hours. In some embodiments, a method of treating bacterial vaginosis in a subject comprises administering to the subject a single dose of a secnidazole microgranule formulation that exhibits a time to maximum plasma concentration ($T_{max}$) of about 2 hours to about 6 hours.

In some embodiments, a method of reducing the incidence and/or risk of a subject transmitting HIV to a sexual partner in a subject further comprises the absence of HIV transmission. In some embodiments, a method of reducing the incidence and/or risk of a subject transmitting human immunodeficiency virus (HIV) to a sexual partner in a subject further comprises determining a post treatment clinical outcome. In some embodiments, a post treatment clinical outcome is indicative of a clinical outcome responder. Some embodiments further comprise determining a post-treatment clinical outcome. In some embodiments, a post-treatment clinical outcome of clinical cure is defined as a clinical outcome responder. In some embodiments, a clinical outcome responder is a subject with normal vaginal discharge, a negative KOH Whiff test, and clue cells less than or equal to 20% of the total epithelial cells on microscopic examination of a vaginal saline wet mount after treatment with a microgranule formulation comprising about 1 grams to about 2 grams of secnidazole. In some embodiments, a clinical outcome responder has a gram stain slide Nugent score of less than four (4) after treatment with a single dose of secnidazole. In yet other embodiments, a clinical outcome responder is a subject with normal vaginal discharge, a negative KOH Whiff test, clue cells less than 20% of total epithelial cells, and a gram stain slide Nugent score of less than four (4) after treatment with a single dose of secnidazole. In some embodiments, a clinical outcome responder has a gram stain slide Nugent score of less than four (4) after treatment with a 2 gram single dose of secnidazole. In yet other embodiments, a clinical outcome responder is a subject with normal vaginal discharge, a negative KOH Whiff test, clue cells less than 20% of total epithelial cells, and a gram stain slide Nugent score of less than four (4) after treatment with a 2 gram single dose of secnidazole. In some embodiments, a post-treatment clinical outcome is observable after about 24 hours after administration. In some embodiments, a post-treatment clinical outcome is observable after about 48 hours after administration. In some embodiments, a post-treatment clinical outcome is observable after about 72 hours after administration. In some embodiments, a post-treatment clinical outcome is observable after about 96 hours after administration. In some embodiments, a post-treatment clinical outcome is observable after about 120 hours after administration. In some embodiments, a post-treatment clinical outcome is observable after about 168 hours after administration. In some embodiments, a post-treatment clinical outcome is observable after about 7 days to about 10 days after administration. In some embodiments, a post-treatment clinical outcome is observable after about 11 days to about 20 days after administration. In some embodiments, a post-treatment clinical outcome is observable after about 21 days to about 30 days after administration.

In some embodiments, a method of reducing the incidence and/or risk of a subject transmitting HIV to a sexual partner in a subject further comprises an alleviation of one or more symptoms of bacterial vaginosis within up to about three days after administration to the subject. In some embodiments, a method of treating bacterial vaginosis further comprises an alleviation of one or more symptoms of bacterial vaginosis within up to about three days after administration to the subject. In some embodiments, the one or more symptoms include, but are not limited to, abnormal vaginal odor, abnormal vaginal discharge or a combination thereof. In some embodiments, alleviation refers to a lessening of the severity of one or more symptoms. In some embodiments, alleviation of one or more symptoms of bacterial vaginosis occurs within about 24 hours after administration. In some embodiments, alleviation of one or more symptoms of bacterial vaginosis occurs within about 48 hours after administration. In some embodiments, alleviation of one or more symptoms of bacterial vaginosis occurs within about 72 hours after administration to the subject. In some embodiments, alleviation of one or more symptoms of bacterial vaginosis occurs within about 96 hours after administration to the subject. In some embodiments, alleviation of one or more symptoms of bacterial vaginosis occurs within about 120 hours after administration to the subject. In some embodiments, alleviation of one or more symptoms of bacterial vaginosis occurs within about 168 hours after administration to the subject. In some embodiments, alleviation of one or more symptoms of bacterial vaginosis occurs within about 7 days to about 10 days after administration to the subject. In some embodiments, alleviation of one or more symptoms of bacterial vaginosis occurs within about 11 days to about 20 days after administration to the subject. In some embodiments, alleviation of one or more symptoms of bacterial vaginosis occurs within about 21 days to about 30 days after administration to the subject.

In some embodiments, a method of reducing the incidence and/or risk of a subject transmitting HIV to a sexual partner a subject further comprises a resolution of one or more symptoms of bacterial vaginosis within up to about seven days after administration to the subject. In some embodiments, a method of treating bacterial vaginosis further comprises a resolution of one or more symptoms of bacterial vaginosis within up to about seven days after administration to the subject. In some embodiments, the one or more symptoms include, but are not limited to, abnormal vaginal odor, abnormal vaginal discharge or a combination thereof. In some embodiments, resolution of one or more symptoms of bacterial vaginosis occurs within about 24 hours after administration to the subject. In some embodiments, resolution of one or more symptoms of bacterial vaginosis occurs within about 48 hours after administration. In some embodiments, resolution of one or more symptoms of bacterial vaginosis occurs within about 72 hours after administration to the subject. In some embodiments, resolution of one or more symptoms of bacterial vaginosis occurs within about 96 hours after administration to the subject. In some embodiments, resolution of one or more symptoms of bacterial vaginosis occurs within about 120 hours after administration to the subject. In some embodiments, resolution of one or more symptoms of bacterial vaginosis occurs within about 168 hours after administration to the subject. In some embodiments, resolution of one or more symptoms of bacterial vaginosis occurs within about 7 days to about 10 days after administration to the subject. In some embodiments, resolution of one or more symptoms of bacterial vaginosis occurs within about 11 days to about 20 days after administration to the subject. In some embodiments, resolution of one or more symptoms of bacterial vaginosis occurs within about 21 days to about 30 days after administration to the subject.

Some embodiments are directed to a method of reducing the incidence and/or risk of a subject acquiring HIV from a sexual partner. Bacterial vaginosis infections may increase the risk of a HIV transmission to sexual partner as well as the risk of acquiring HIV from a sexual partner. In some embodiments, a method of reducing the incidence and/or risk of the subject transmitting HIV to a sexual partner comprises administering to the subject a therapeutically effective amount of secnidazole or pharmaceutically acceptable salts thereof. In some embodiments, a method of reducing the incidence and/or risk of a preterm birth in a subject comprises administering to the subject a therapeutically effective amount of secnidazole or pharmaceutically acceptable salts thereof in a microgranule formulation. In some embodiments, the secnidazole microgranule formulation may be suitable for oral administration. In some embodiments, the secnidazole microgranule formulation comprises a plurality of microgranules. In some embodiments, the plurality of microgranules are white to off-white in color. In some embodiments, the plurality of microgranules each have a particle size range of about 400 micrometers to about 841 micrometers. In some embodiments, the secnidazole microgranule formulation may be mixed, stirred, or otherwise integrated into a food substance. In some embodiments, the food substance may be a liquid, semisolid, or soft food. In some embodiments, the food substance may include, but is not limited to applesauce, pudding, yogurt or the like. In some embodiments, integration of the secnidazole microgranule formulation into a food substance has a taste masking function. In some embodiments, the secnidazole microgranule formulation may be mixed, stirred, or otherwise integrated in a liquid, such as water, juice, milk or the like.

In some embodiments, the subject is a human. In yet other embodiments, the subject is a pregnant human female. In some embodiments, the subject is an otherwise healthy female. In some embodiments, the subject is a female without HIV. In some embodiments, the subject has a sexual partner that is HIV positive. In some embodiments, the subject is an otherwise healthy pregnant female. In some embodiments, the subject is a female having had 3 or fewer bacterial vaginosis infections in the past 12 months. In some embodiments, the subject is a female having had 4 or more bacterial vaginosis infections in the past twelve months. In some embodiments, the subject is a female with recurring bacterial vaginosis. In some embodiments, a subject with recurring bacterial vaginosis is a subject with 4 or more bacterial vaginosis infections within a twelve-month period. In some embodiments, the subject is a female with frequent bacterial vaginosis infections. In some embodiments, a female with frequent bacterial vaginosis infections is a female with 4 or more bacterial vaginosis infections within a twelve-month period. In some embodiments, the subject is a female presenting with an off-white (milky or gray), thin, homogeneous vaginal discharge, vaginal pH greater than or equal to 4.7, presence of clue cells of greater than or equal to 20% of the total epithelial cells on microscopic examination of a vaginal saline wet mount, a positive 10% KOH Whiff test or a combination thereof. In some embodiments, the subject is a female presenting with an off-white (milky or gray), thin, homogeneous vaginal discharge, vaginal pH greater than or equal to 4.7, the presence of clue cells of greater than or equal to 20% of the total epithelial cells on microscopic examination of a vaginal saline wet mount, and a positive 10% KOH Whiff test. In some embodiments, the subject is a female with confirmed bacterial vaginosis. In some embodiments, bacterial vaginosis is confirmed by the presence of four (4) Amsel criteria parameters selected from an off-white (milky or gray), thin, homogeneous vaginal discharge, vaginal pH greater than or equal to 4.7, the presence of clue cells of greater than or equal to 20% of the total epithelial cells on microscopic examination of a vaginal saline wet mount, a positive 10% KOH Whiff test and a gram stain slide Nugent score equal to, or higher than four (4) on bacterial analysis of vaginal samples. In some embodiments, the subject is a female with suspected bacterial vaginosis. In some embodiments, suspected bacterial vaginosis is indicated by the presence of four (4) Amsel criteria parameters selected from an off-white (milky or gray), thin, homogeneous vaginal discharge, vaginal pH greater than or equal to 4.7, the presence of clue cells of greater than or equal to 20% of the total epithelial cells on microscopic examination of a vaginal saline wet mount, and a positive 10% KOH Whiff test. In some embodiments, the subject is a female presenting with an off-white (milky or gray), thin, homogeneous vaginal discharge, odor, or a combination thereof.

In some embodiments, a method of reducing the incidence and/or risk of a subject acquiring HIV from a sexual partner comprises administering to the subject a single dose of a therapeutically effective amount of secnidazole in a microgranule formulation, wherein the secnidazole comprises about 1 g to about 2 g of the microgranule formulation. In some embodiments, the secnidazole microgranule formulation is co-administered with an additional compound selected from ethinyl estradiol (EE2), norethindrone (NET), or a combination thereof. In some embodiments, the secnidazole microgranule formulation is mixed into a liquid, semisolid or soft food substance, such as but not limited to applesauce yogurt and pudding. In some embodiments, the amount of the food substance is about 4-6 ounces. In some embodiments, the secnidazole microgranule formulation may be mixed, stirred, or otherwise integrated in a liquid, such as water, juice, milk or the like.

In some embodiments, a method of reducing the incidence and/or risk of a subject acquiring HIV from a sexual partner comprises administering to the subject a single dose of a secnidazole microgranule formulation that exhibits a maximum serum concentration ($C_{max}$) of between about 34.5 μg/ml and about 58.3 μg/ml. In some embodiments, a method of treating bacterial vaginosis in a subject comprises administering to the subject a single dose of a secnidazole microgranule formulation that exhibits a maximum serum concentration ($C_{max}$) of between about 17.4 μg/ml and about 26.5 μg/ml.

In some embodiments, a method of reducing the incidence and/or risk of a subject acquiring HIV from a sexual partner comprises administering to the subject a single dose of a secnidazole microgranule formulation that exhibits a time to maximum plasma concentration ($T_{max}$) of about 3 hours to about 4.05 hours. In some embodiments, a method of treating bacterial vaginosis in a subject comprises administering to the subject a single dose of a secnidazole microgranule formulation that exhibits a time to maximum plasma concentration ($T_{max}$) of about 2 hours to about 6 hours.

In some embodiments, a method of reducing the incidence and/or risk of a subject acquiring HIV from a sexual partner in a subject further comprises the absence of HIV transmission. In some embodiments, a method of reducing the incidence and/or risk of a subject transmitting human immunodeficiency virus (HIV) to a sexual partner in a subject further comprises determining a post treatment clinical outcome. In some embodiments, a post treatment clinical outcome is indicative of a clinical outcome responder. Some embodiments further comprise determining a post-treatment clinical outcome. In some embodiments, a post-treatment clinical outcome of clinical cure is defined as a clinical outcome responder. In some embodiments, a clinical outcome responder is a subject with normal vaginal discharge, a negative KOH Whiff test, and clue cells less than or equal to 20% of the total epithelial cells on microscopic examination of a vaginal saline wet mount after treatment with a microgranule formulation comprising about 1 grams to about 2 grams of secnidazole. In some embodiments, a clinical outcome responder has a gram stain slide Nugent score of less than four (4) after treatment with a single dose of secnidazole. In yet other embodiments, a clinical outcome responder is a subject with normal vaginal discharge, a negative KOH Whiff test, clue cells less than 20% of total epithelial cells, and a gram stain slide Nugent score of less than four (4) after treatment with a single dose of secnidazole. In some embodiments, a clinical outcome responder has a gram stain slide Nugent score of less than four (4) after treatment with a 2 gram single dose of secnidazole. In yet other embodiments, a clinical outcome responder is a subject with normal vaginal discharge, a negative KOH Whiff test, clue cells less than 20% of total epithelial cells, and a gram stain slide Nugent score of less than four (4) after treatment with a 2 gram single dose of secnidazole. In some embodiments, a post-treatment clinical outcome is observable after about 24 hours after administration. In some embodiments, a post-treatment clinical outcome is observable after about 48 hours after administration. In some embodiments, a post-treatment clinical outcome is observable after about 72 hours after administration. In some embodiments, a post-treatment clinical outcome is observable after about 96 hours after administration. In some embodiments, a post-treatment clinical outcome is observable after about 120 hours after administration. In some embodiments, a post-treatment clinical outcome is observable after about 168 hours after administration. In some embodiments, a post-treatment clinical outcome is observable after about 7 days to about 10 days after administration. In some embodiments, a post-treatment clinical outcome is observable after about 11 days to about 20 days after administration. In some embodiments, a post-treatment clinical outcome is observable after about 21 days to about 30 days after administration.

In some embodiments, a method of reducing the incidence and/or risk of a subject acquiring HIV from a sexual partner further comprises an alleviation of one or more symptoms of bacterial vaginosis within up to about three days after administration to the subject. In some embodiments, a method of treating bacterial vaginosis further comprises an alleviation of one or more symptoms of bacterial vaginosis within up to about three days after administration to the subject. In some embodiments, the one or more symptoms include, but are not limited to, abnormal vaginal odor, abnormal vaginal discharge or a combination thereof. In some embodiments, alleviation refers to a lessening of the severity of one or more symptoms. In some embodiments, alleviation of one or more symptoms of bacterial vaginosis occurs within about 24 hours after administration. In some embodiments, alleviation of one or more symptoms of bacterial vaginosis occurs within about 48 hours after administration. In some embodiments, alleviation of one or more symptoms of bacterial vaginosis occurs within about 72 hours after administration to the subject. In some embodiments, alleviation of one or more symptoms of bacterial vaginosis occurs within about 96 hours after administration to the subject. In some embodiments, alleviation of one or more symptoms of bacterial vaginosis occurs within about 120 hours after administration to the subject. In some embodiments, alleviation of one or more symptoms of bacterial vaginosis occurs within about 168 hours after administration to the subject. In some embodiments, alleviation of one or more symptoms of bacterial vaginosis occurs within about 7 days to about 10 days after administration to the subject. In some embodiments, alleviation of one or more symptoms of bacterial vaginosis occurs within about 11 days to about 20 days after administration to the subject. In some embodiments, alleviation of one or more symptoms of bacterial vaginosis occurs within about 21 days to about 30 days after administration to the subject.

In some embodiments, a method of reducing the incidence and/or risk of a subject acquiring HIV from a sexual partner further comprises a resolution of one or more symptoms of bacterial vaginosis within up to about seven days after administration to the subject. In some embodiments, a method of treating bacterial vaginosis further comprises a resolution of one or more symptoms of bacterial vaginosis within up to about seven days after administration to the subject. In some embodiments, the one or more symptoms include, but are not limited to, abnormal vaginal odor, abnormal vaginal discharge or a combination thereof. In some embodiments, resolution of one or more symptoms of bacterial vaginosis occurs within about 24 hours after administration to the subject. In some embodiments, resolution of one or more symptoms of bacterial vaginosis occurs within about 48 hours after administration. In some embodiments, resolution of one or more symptoms of bacterial vaginosis occurs within about 72 hours after administration to the subject. In some embodiments, resolution of one or more symptoms of bacterial vaginosis occurs within about 96 hours after administration to the subject. In some embodiments, resolution of one or more symptoms of bacterial vaginosis occurs within about 120 hours after administration to the subject. In some embodiments, resolution of one or more symptoms of bacterial vaginosis occurs within about 168 hours after administration to the subject. In some embodiments, resolution of one or more symptoms of bacterial vaginosis occurs within about 7 days to about 10 days after administration to the subject. In some embodiments, resolution of one or more symptoms of bacterial vaginosis occurs within about 11 days to about 20 days after administration to the subject. In some embodiments, resolution of one or more symptoms of bacterial vaginosis occurs within about 21 days to about 30 days after administration to the subject.

Some embodiments are directed to a method of reducing the incidence and/or risk of a subject acquiring a sexually transmitted infection (STI) from a sexual partner. Bacterial vaginosis infections may increase the risk of acquiring an STI from a sexual partner. In some embodiments, STI's include, but are not limited to *chlamydia*, gonorrhea, trichomoniasis, HSV-2, and HPV. In some embodiments, a method of reducing the incidence and/or risk of the subject transmitting HIV to a sexual partner in a subject comprises administering to the subject a therapeutically effective amount of secnidazole or pharmaceutically acceptable salts thereof. In some embodiments, a method of reducing the incidence and/or risk of a preterm birth in a subject comprises administering to the subject a therapeutically effective amount of secnidazole or pharmaceutically acceptable salts thereof in a microgranule formulation. In some embodiments, the secnidazole microgranule formulation may be suitable for oral administration. In some embodiments, the secnidazole microgranule formulation comprises a plurality of microgranules. In some embodiments, the plurality of microgranules are white to off-white in color. In some embodiments, the plurality of microgranules each have a particle size range of about 400 micrometers to about 841 micrometers. In some embodiments, the secnidazole microgranule formulation may be mixed, stirred, or otherwise integrated into a food substance. In some embodiments, the food substance may be a liquid, semisolid or soft food. In some embodiments, the food substance may include, but is not limited to applesauce, pudding, yogurt or the like. In some embodiments, integration of the secnidazole microgranule formulation into a food substance has a taste masking function. In some embodiments, the secnidazole microgranule formulation may be mixed, stirred, or otherwise integrated in a liquid, such as water, juice, milk or the like.

In some embodiments, the subject is a human. In yet other embodiments, the subject is a pregnant human female. In some embodiments, the subject is an otherwise healthy female. In some embodiments, the subject is a female with an STI. In some embodiments, the subject is a female having had 3 or fewer bacterial vaginosis infections in the past 12 months. In some embodiments, the subject is a female having had 4 or more bacterial vaginosis infections in the past twelve months. In some embodiments, the subject is a female with recurring bacterial vaginosis. In some embodiments, a subject with recurring bacterial vaginosis is a subject with 4 or more bacterial vaginosis infections within a twelve-month period. In some embodiments, the subject is a female with frequent bacterial vaginosis infections. In some embodiments, a female with frequent bacterial vaginosis infections is a female with 4 or more bacterial vaginosis infections within a twelve-month period. In some embodiments, the subject is a female presenting with an off-white (milky or gray), thin, homogeneous vaginal discharge, vaginal pH greater than or equal to 4.7, presence of clue cells of greater than or equal to 20% of the total epithelial cells on microscopic examination of a vaginal saline wet mount, a positive 10% KOH Whiff test or a combination thereof. In some embodiments, the subject is a female presenting with an off-white (milky or gray), thin, homogeneous vaginal discharge, vaginal pH greater than or equal to 4.7, the presence of clue cells of greater than or equal to 20% of the total epithelial cells on microscopic examination of a vaginal saline wet mount, and a positive 10% KOH Whiff test. In some embodiments, the subject is a female with confirmed bacterial vaginosis. In some embodiments, bacterial vaginosis is confirmed by the presence of four (4) Amsel criteria parameters selected from an off-white (milky or gray), thin, homogeneous vaginal discharge, vaginal pH greater than or equal to 4.7, the presence of clue cells of greater than or equal to 20% of the total epithelial cells on microscopic examination of a vaginal saline wet mount, a positive 10% KOH Whiff test and a gram stain slide Nugent score equal to, or higher than four (4) on bacterial analysis of vaginal samples. In some embodiments, the subject is a female with suspected bacterial vaginosis. In some embodiments, suspected bacterial vaginosis is indicated by the presence of four (4) Amsel criteria parameters selected from an off-white (milky or gray), thin, homogeneous vaginal discharge, vaginal pH greater than or equal to 4.7, the presence of clue cells of greater than or equal to 20% of the total epithelial cells on microscopic examination of a vaginal saline wet mount, and a positive 10% KOH Whiff test. In some embodiments, the subject is a female presenting with an off-white (milky or gray), thin, homogeneous vaginal discharge, odor, or a combination thereof.

In some embodiments, a method of reducing the incidence and/or risk of a subject acquiring an STI from a sexual partner comprises administering to the subject a single dose of a therapeutically effective amount of secnidazole in a microgranule formulation, wherein the secnidazole comprises about 1 g to about 2 g of the microgranule formulation. In some embodiments, the secnidazole microgranule formulation is co-administered with an additional compound selected from ethinyl estradiol (EE2), norethindrone (NET), or a combination thereof. In some embodiments, the secnidazole microgranule formulation is mixed into a liquid, semisolid or soft food substance, such as but not limited to applesauce yogurt and pudding. In some embodiments, the amount of the food substance is about 4-6 ounces. In some embodiments, the secnidazole microgranule formulation may be mixed, stirred, or otherwise integrated in a liquid, such as water, juice, milk or the like.

In some embodiments, a method of reducing the incidence and/or risk of a subject acquiring an STI from a sexual partner comprises administering to the subject a single dose of a secnidazole microgranule formulation that exhibits a maximum serum concentration ($C_{max}$) of between about 34.5 μg/ml and about 58.3 μg/ml. In some embodiments, a method of treating bacterial vaginosis in a subject comprises administering to the subject a single dose of a secnidazole microgranule formulation that exhibits a maximum serum concentration ($C_{max}$) of between about 17.4 μg/ml and about 26.5 μg/ml.

In some embodiments, a method of reducing the incidence and/or risk of a subject acquiring an STI from a sexual partner comprises administering to the subject a single dose of a secnidazole microgranule formulation that exhibits a time to maximum plasma concentration ($T_{max}$) of about 3 hours to about 4.05 hours. In some embodiments, a method of treating bacterial vaginosis in a subject comprises administering to the subject a single dose of a secnidazole microgranule formulation that exhibits a time to maximum plasma concentration ($T_{max}$) of about 2 hours to about 6 hours.

In some embodiments, a method of reducing the incidence and/or risk of a subject acquiring an STI from a sexual partner further comprises the absence of an STI transmission or acquisition of an STI by the subject. In some embodiments, a method of reducing the incidence and/or risk of a subject acquiring an STI from a sexual partner further comprises determining a post treatment clinical outcome. In some embodiments, a post treatment clinical outcome is indicative of a clinical outcome responder. Some embodiments further comprise determining a post-treatment clinical outcome. In some embodiments, a post-treatment clinical outcome of clinical cure is defined as a clinical outcome responder. In some embodiments, a clinical outcome responder is a subject with normal vaginal discharge, a negative KOH Whiff test, and clue cells less than or equal to 20% of the total epithelial cells on microscopic examination of a vaginal saline wet mount after treatment with a microgranule formulation comprising about 1 grams to about 2 grams of secnidazole. In some embodiments, a clinical outcome responder has a gram stain slide Nugent score of less than four (4) after treatment with a single dose of secnidazole. In yet other embodiments, a clinical outcome responder is a subject with normal vaginal discharge, a negative KOH Whiff test, clue cells less than 20% of total epithelial cells, and a gram stain slide Nugent score of less than four (4) after treatment with a single dose of secnidazole. In some embodiments, a clinical outcome responder has a gram stain slide Nugent score of less than four (4) after treatment with a 2 gram single dose of secnidazole. In yet other embodiments, a clinical outcome responder is a subject with normal vaginal discharge, a negative KOH Whiff test, clue cells less than 20% of total epithelial cells, and a gram stain slide Nugent score of less than four (4) after treatment with a 2 gram single dose of secnidazole. In some embodiments, a post-treatment clinical outcome is observable after about 24 hours after administration. In some embodiments, a post-treatment clinical outcome is observable after about 48 hours after administration. In some embodiments, a post-treatment clinical outcome is observable after about 72 hours after administration. In some embodiments, a post-treatment clinical outcome is observable after about 96 hours after administration. In some embodiments, a post-treatment clinical outcome is observable after about 120 hours after administration. In some embodiments, a post-treatment clinical outcome is observable after about 168 hours after administration. In some embodiments, a post-treatment clinical outcome is observable after about 7 days to about 10 days after administration. In some embodiments, a post-treatment clinical outcome is observable after about 11 days to about 20 days after administration. In some embodiments, a post-treatment clinical outcome is observable after about 21 days to about 30 days after administration.

In some embodiments, a method of reducing the incidence and/or risk of a subject acquiring an STI from a sexual partner further comprises an alleviation of one or more symptoms of bacterial vaginosis within up to about three days after administration to the subject. In some embodiments, a method of treating bacterial vaginosis further comprises an alleviation of one or more symptoms of bacterial vaginosis within up to about three days after administration to the subject. In some embodiments, the one or more symptoms include, but are not limited to, abnormal vaginal odor, abnormal vaginal discharge or a combination thereof. In some embodiments, alleviation refers to a lessening of the severity of one or more symptoms. In some embodiments, alleviation of one or more symptoms of bacterial vaginosis occurs within about 24 hours after administration. In some embodiments, alleviation of one or more symptoms of bacterial vaginosis occurs within about 48 hours after administration. In some embodiments, alleviation of one or more symptoms of bacterial vaginosis occurs within about 72 hours after administration to the subject. In some embodiments, alleviation of one or more symptoms of bacterial vaginosis occurs within about 96 hours after administration to the subject. In some embodiments, alleviation of one or more symptoms of bacterial vaginosis occurs within about 120 hours after administration to the subject. In some embodiments, alleviation of one or more symptoms of bacterial vaginosis occurs within about 168 hours after administration to the subject. In some embodiments, alleviation of one or more symptoms of bacterial vaginosis occurs within about 7 days to about 10 days after administration to the subject. In some embodiments, alleviation of one or more symptoms of bacterial vaginosis occurs within about 11 days to about 20 days after administration to the subject. In some embodiments, alleviation of one or more symptoms of bacterial vaginosis occurs within about 21 days to about 30 days after administration to the subject.

In some embodiments, a method of reducing the incidence and/or risk of a subject acquiring an STI from a sexual partner further comprises a resolution of one or more symptoms of bacterial vaginosis within up to about seven days after administration to the subject. In some embodiments, a method of treating bacterial vaginosis further comprises a resolution of one or more symptoms of bacterial vaginosis within up to about seven days after administration to the subject. In some embodiments, the one or more symptoms include, but are not limited to, abnormal vaginal odor, abnormal vaginal discharge or a combination thereof. In some embodiments, resolution of one or more symptoms of bacterial vaginosis occurs within about 24 hours after administration to the subject. In some embodiments, resolution of one or more symptoms of bacterial vaginosis occurs within about 48 hours after administration. In some embodiments, resolution of one or more symptoms of bacterial vaginosis occurs within about 72 hours after administration to the subject. In some embodiments, resolution of one or more symptoms of bacterial vaginosis occurs within about 96 hours after administration to the subject. In some embodiments, resolution of one or more symptoms of bacterial vaginosis occurs within about 120 hours after administration to the subject. In some embodiments, resolution of one or more symptoms of bacterial vaginosis occurs within about 168 hours after administration to the subject. In some embodiments, resolution of one or more symptoms of bacterial vaginosis occurs within about 7 days to about 10 days after administration to the subject. In some embodiments, resolution of one or more symptoms of bacterial vaginosis occurs within about 11 days to about 20 days after administration to the subject. In some embodiments, resolution of one or more symptoms of bacterial vaginosis occurs within about 21 days to about 30 days after administration to the subject.

Some embodiments are directed to a method of preventing recurrence of bacterial vaginosis. In some embodiments, the method of preventing recurrence of bacterial vaginosis comprises administering a microgranule formulation comprising about 1 grams to about 2 grams secnidazole to a subject in need thereof. In some embodiments, the recurrence of bacterial vaginosis is decreased after administration of a single, 2 gram dose of secnidazole. In some embodiments, the recurrence of bacterial vaginosis is decreased after administration of a multiple, 2 gram doses of secnidazole. In some embodiments, multiple doses may be given at pre-determined intervals such as but not limited to once a week, bi-weekly, monthly, bimonthly for the duration of treatment. In some embodiment, the duration of treatment may be at least one week. In some embodiment, the duration of treatment may be at least one month. In some embodiments, the duration of treatment is about six months. Some embodiments are directed to a method of preventing recurrence of bacterial vaginosis comprising administering a microgranule formulation comprising about 2 grams secnidazole, to a subject in need thereof. In some embodiments, the microgranule formulation comprising about 2 grams secnidazole is administered as a single dose. In some embodiments, the single dose of secnidazole is the only dose need to prevent recurrence of bacterial vaginosis. In some embodiments, the microgranule formulation comprising about 2 grams secnidazole is administered in multiple doses. In some embodiments, multiple doses may be given at pre-determined intervals such as but not limited to once a week, bi-weekly, monthly, bimonthly for the duration of treatment. In some embodiment, the duration of treatment may be at least one week. In some embodiment, the duration of treatment may be at least one month. In some embodiments, the duration of treatment is about six months.

In some embodiments, the method of preventing recurrence of bacterial vaginosis in a subject in need thereof comprises administering to the subject a therapeutically effective amount of secnidazole or pharmaceutically acceptable salts thereof in a microgranule formulation. In some embodiments, the secnidazole microgranule formulation may be suitable for oral administration. In some embodiments, the secnidazole microgranule formulation comprises a plurality of microgranules. In some embodiments, the plurality of microgranules are white to off-white in color. In some embodiments, the plurality of microgranules each have a particle size range of about 400 micrometers to about 841 micrometers.

In some embodiments, the plurality of microgranules has a volume-weighted particle size distribution within a microgranule population, wherein the volume-weighted particle size distribution as measured from a representative sample of the microgranule population includes:

10% of the microgranule population has a volume-weighted particle size about no less than 470 micrometers;

(b) 50% of the microgranule population has a volume-weighted particle size between about no less than 640 micrometers and about no more than 810 micrometers;

(c) 90% of the microgranule population has a volume-weighted particle size about no more than 1170 micrometers; or (d) a combination thereof, which can include some or all of (a) through (c) above.

In some embodiments, the secnidazole microgranule formulation may be mixed, stirred, or otherwise integrated into a food substance. In some embodiments, the food substance may be a liquid, semisolid or soft food. In some embodiments, the food substance may include, but is not limited to applesauce, pudding, yogurt or the like. In some embodiments, integration of the secnidazole microgranule formulation into a food substance has a taste masking function. In some embodiments, the secnidazole microgranule formulation may be mixed, stirred, or otherwise integrated in a liquid, such as water, juice, milk or the like.

In some embodiments, the subject is a female. In some embodiments, the subject is an otherwise healthy female. In some embodiments, the subject is a pregnant female. In some embodiments, the subject is an otherwise healthy pregnant female. In some embodiments, the subject is a female having had 3 or fewer bacterial vaginosis infections in the past 12 months. In some embodiments, the subject is a female having had 3 or more bacterial vaginosis infections in the past 12 months. In some embodiments, the subject is a female having had 4 or more bacterial vaginosis infections in the past twelve months. In some embodiments, the subject is a female with recurring bacterial vaginosis. In some embodiments, a subject with recurring bacterial vaginosis is a subject with 3 or more bacterial vaginosis infections within a twelve-month period. In some embodiments, a subject with recurring bacterial vaginosis is a subject with 4 or more bacterial vaginosis infections within a twelve-month period. In some embodiments, the subject is a female with frequent bacterial vaginosis infections. In some embodiments, a female with frequent bacterial vaginosis infections is a female with 4 or more bacterial vaginosis infections within a twelve-month period. In some embodiments, the subject is a female presenting with an off-white (milky or gray), thin, homogeneous vaginal discharge, vaginal pH greater than or equal to 4.7, presence of clue cells of greater than or equal to 20% of the total epithelial cells on microscopic examination of a vaginal saline wet mount, a positive 10% KOH Whiff test or a combination thereof. In some embodiments, the subject is a female presenting with an off-white (milky or gray), thin, homogeneous vaginal discharge, vaginal pH greater than or equal to 4.7, the presence of clue cells of greater than or equal to 20% of the total epithelial cells on microscopic examination of a vaginal saline wet mount, and a positive 10% KOH Whiff test. In some embodiments, the subject is a female with confirmed bacterial vaginosis. In some embodiments, bacterial vaginosis is confirmed by the presence of four (4) Amsel criteria parameters selected from an off-white (milky or gray), thin, homogeneous vaginal discharge, vaginal pH greater than or equal to 4.7, the presence of clue cells of greater than or equal to 20% of the total epithelial cells on microscopic examination of a vaginal saline wet mount, a positive 10% KOH Whiff test and a gram stain slide Nugent score equal to, or higher than four (4) on bacterial analysis of vaginal samples. In some embodiments, the subject is a female with suspected bacterial vaginosis. In some embodiments, suspected bacterial vaginosis is indicated by the presence of four (4) Amsel criteria parameters selected from an off-white (milky or gray), thin, homogeneous vaginal discharge, vaginal pH greater than or equal to 4.7, the presence of clue cells of greater than or equal to 20% of the total epithelial cells on microscopic examination of a vaginal saline wet mount, and a positive 10% KOH Whiff test. In some embodiments, the subject is a female presenting with an off-white (milky or gray), thin, homogeneous vaginal discharge, odor, or a combination thereof.

In some embodiments, a method of preventing recurrence of bacterial vaginosis in a subject comprises administering to the subject a single dose of a therapeutically effective amount of secnidazole in a microgranule formulation, wherein the secnidazole comprises about 1 g to about 2 g of the microgranule formulation. In some embodiments, a method of preventing recurrence of bacterial vaginosis in a subject comprises administering to the subject multiple doses of a therapeutically effective amount of secnidazole in a microgranule formulation, wherein the secnidazole comprises about 1 g to about 2 g of the microgranule formulation. In some embodiments, multiple doses may be given at pre-determined intervals such as but not limited to once a week, bi-weekly, monthly, bimonthly for the duration of treatment. In some embodiment, the duration of treatment may be at least one week. In some embodiment, the duration of treatment may be at least one month. In some embodiments, the duration of treatment is about six months. In some embodiments, the secnidazole microgranule formulation is mixed into a liquid, semisolid or soft food substance, such as but not limited to applesauce yogurt and pudding. In some embodiments, the amount of the food substance is about 4-6 ounces. In some embodiments, the secnidazole microgranule formulation may be mixed, stirred, or otherwise integrated in a liquid, such as water, juice, milk or the like.

In some embodiments, a method of preventing recurrence of bacterial vaginosis in a subject comprises administering to the subject a single dose of a secnidazole microgranule formulation that exhibits a maximum serum concentration ($C_{max}$) of between about 34.5 µg/ml and about 58.3 µg/ml. In some embodiments, a method of preventing recurrence of bacterial vaginosis in a subject comprises administering to the subject a single dose of a secnidazole microgranule formulation that exhibits a maximum serum concentration ($C_{max}$) of between about 17.4 µg/ml and about 26.5 µg/ml. In some embodiments, a method of preventing recurrence of bacterial vaginosis in a subject comprises administering to the subject multiple doses of a secnidazole microgranule formulation wherein each dose exhibits a maximum serum concentration ($C_{max}$) of between about 34.5 µg/ml and about 58.3 µg/ml. In some embodiments, multiple doses may be given at pre-determined intervals such as but not limited to once a week, bi-weekly, monthly, bimonthly for the duration of treatment. In some embodiment, the duration of treatment may be at least one week. In some embodiment, the duration of treatment may be at least one month. In some embodiments, the duration of treatment is about six months. In some embodiments, a method of preventing recurrence of bacterial vaginosis in a subject comprises administering to the subject multiple doses of a secnidazole microgranule formulation wherein each dose exhibits a maximum serum concentration ($C_{max}$) of between about 17.4 µg/ml and about 26.5 µg/ml. In some embodiments, multiple doses may be given at pre-determined intervals such as but not limited to once a week, bi-weekly, monthly, bimonthly for the duration of treatment. In some embodiment, the duration of treatment may be at least one week. In some embodiment, the duration of treatment may be at least one month. In some embodiments, the duration of treatment is about six months.

In some embodiments, a method of preventing recurrence of bacterial vaginosis in a subject comprises administering to the subject a single dose of a secnidazole microgranule formulation that exhibits a time to maximum plasma concentration ($T_{max}$) of about 3 hours to about 4.05 hours. In some embodiments, a method of preventing recurrence of bacterial vaginosis in a subject comprises administering to the subject a single dose of a secnidazole microgranule formulation that exhibits a time to maximum plasma concentration ($T_{max}$) of about 2 hours to about 6 hours. In some embodiments, a method of preventing recurrence of bacterial vaginosis in a subject comprises administering to the subject multiple doses of a secnidazole microgranule formulation wherein a single dose exhibits a time to maximum plasma concentration ($T_{max}$) of about 3 hours to about 4.05 hours. In some embodiments, a method of preventing recurrence of bacterial vaginosis in a subject comprises administering to the subject multiple doses of a secnidazole microgranule formulation wherein each dose exhibits a time to maximum plasma concentration ($T_{max}$) of about 2 hours to about 6 hours. In some embodiments, multiple doses may be given at pre-determined intervals such as but not limited to once a week, bi-weekly, monthly, bimonthly for the duration of treatment. In some embodiment, the duration of treatment may be at least one week. In some embodiment, the duration of treatment may be at least one month. In some embodiments, the duration of treatment is about six months.

In some embodiments, a method of preventing recurrence of bacterial vaginosis in a subject further comprises determining a post treatment clinical outcome. In some embodiments, a post treatment clinical outcome is indicative of a clinical outcome responder. Some embodiments further comprise determining a post-treatment clinical outcome. In some embodiments, a post-treatment clinical outcome of clinical cure is defined as a clinical outcome responder. In some embodiments, a clinical outcome responder is a subject with normal vaginal discharge, a negative KOH Whiff test, and clue cells less than or equal to 20% of the total epithelial cells on microscopic examination of a vaginal saline wet mount after treatment with an oral microgranule formulation comprising about 1 grams to about 2 grams of secnidazole. In some embodiments, a clinical outcome responder has a gram stain slide Nugent score of less than four (4) after treatment with a single dose of secnidazole. In yet other embodiments, a clinical outcome responder is a subject with normal vaginal discharge, a negative KOH Whiff test, clue cells less than 20% of total epithelial cells, and a gram stain slide Nugent score of less than four (4) after treatment with a single dose of secnidazole. In some embodiments, a clinical outcome responder has a gram stain slide Nugent score of less than four (4) after treatment with a 2 gram single dose of secnidazole. In yet other embodiments, a clinical outcome responder is a subject with normal vaginal discharge, a negative KOH Whiff test, clue cells less than 20% of total epithelial cells, and a gram stain slide Nugent score of less than four (4) after treatment with a 2 gram single dose of secnidazole. In some embodiments, a post-treatment clinical outcome is observable after about 24 hours after administration. In some embodiments, a post-treatment clinical outcome is observable after about 48 hours after administration. In some embodiments, a post-treatment clinical outcome is observable after about 72 hours after administration. In some embodiments, a post-treatment clinical outcome is observable after about 96 hours after administration. In some embodiments, a post-treatment clinical outcome is observable after about 120 hours after administration. In some embodiments, a post-treatment clinical outcome is observable after about 168 hours after administration. In some embodiments, a post-treatment clinical outcome is observable after about 7 days to about 10 days after administration. In some embodiments, a post-treatment clinical outcome is observable after about 11 days to about 20 days after administration. In some embodiments, a post-treatment clinical outcome is observable after about 21 days to about 30 days after administration.

In some embodiments, a method of preventing recurrence of bacterial vaginosis further comprises an alleviation of one or more symptoms of bacterial vaginosis within up to about three days after administration to the subject. In some embodiments, a method of preventing recurrence of bacterial vaginosis further comprises an alleviation of one or more symptoms of bacterial vaginosis within up to about three days after administration to the subject. In some embodiments, the one or more symptoms include, but are not limited to, abnormal vaginal odor, abnormal vaginal discharge or a combination thereof. In some embodiments, alleviation refers to a lessening of the severity of one or more symptoms. In some embodiments, alleviation of one or more symptoms of bacterial vaginosis occurs within about 24 hours after administration. In some embodiments, alleviation of one or more symptoms of bacterial vaginosis occurs within about 48 hours after administration. In some embodiments, alleviation of one or more symptoms of bacterial vaginosis occurs within about 72 hours after administration to the subject. In some embodiments, alleviation of one or more symptoms of bacterial vaginosis occurs within about 96 hours after administration to the subject. In some embodiments, alleviation of one or more symptoms of bacterial vaginosis occurs within about 120 hours after administration to the subject. In some embodiments, alleviation of one or more symptoms of bacterial vaginosis occurs within about 168 hours after administration to the subject. In some embodiments, alleviation of one or more symptoms of bacterial vaginosis occurs within about 7 days to about 10 days after administration to the subject. In some embodiments, alleviation of one or more symptoms of bacterial vaginosis occurs within about 11 days to about 20 days after administration to the subject. In some embodiments, alleviation of one or more symptoms of bacterial vaginosis occurs within about 21 days to about 30 days after administration to the subject.

In some embodiments, a method of preventing recurrence of bacterial vaginosis further comprises a resolution of one or more symptoms of bacterial vaginosis within up to about seven days after administration to the subject. In some embodiments, a method of preventing recurrence of bacterial vaginosis further comprises a resolution of one or more symptoms of bacterial vaginosis within up to about seven days after administration to the subject. In some embodiments, the one or more symptoms include, but are not limited to, abnormal vaginal odor, abnormal vaginal discharge or a combination thereof. In some embodiments, resolution of one or more symptoms of bacterial vaginosis occurs within about 24 hours after administration to the subject. In some embodiments, resolution of one or more symptoms of bacterial vaginosis occurs within about 48 hours after administration. In some embodiments, resolution of one or more symptoms of bacterial vaginosis occurs within about 72 hours after administration to the subject. In some embodiments, resolution of one or more symptoms of bacterial vaginosis occurs within about 96 hours after administration to the subject. In some embodiments, resolution of one or more symptoms of bacterial vaginosis occurs within about 120 hours after administration to the subject. In some embodiments, resolution of one or more symptoms of bacterial vaginosis occurs within about 168 hours after administration to the subject. In some embodiments, resolution of one or more symptoms of bacterial vaginosis occurs within about 7 days to about 10 days after administration to the subject. In some embodiments, resolution of one or more symptoms of bacterial vaginosis occurs within about 11 days to about 20 days after administration to the subject. In some embodiments, resolution of one or more symptoms of bacterial vaginosis occurs within about 21 days to about 30 days after administration to the subject.

In some embodiments, a method of treating bacterial vaginosis in a subject in need thereof further comprises administering to at least one of the subject's sexual partners, a therapeutically effective amount of secnidazole or pharmaceutically acceptable salts thereof. In some embodiments, a method of treating bacterial vaginosis in a subject in need thereof further comprises administering to at least one of the subject's sexual partners, a therapeutically effective amount of secnidazole or pharmaceutically acceptable salts thereof in a microgranule formulation. In some embodiments, the secnidazole microgranule formulation may be suitable for oral administration. In some embodiments, the secnidazole microgranule formulation comprises a plurality of microgranules. In some embodiments, the plurality of microgranules are white to off-white in color. In some embodiments, the plurality of microgranules each have a particle size range of about 400 micrometers to about 841 micrometers.

In some embodiments, the plurality of microgranules has a volume-weighted particle size distribution within a microgranule population, wherein the volume-weighted particle size distribution as measured from a representative sample of the microgranule population includes:
  (a) 10% of the microgranule population has a volume-weighted particle size about no less than 470 micrometers;
  (b) 50% of the microgranule population has a volume-weighted particle size between about no less than 640 micrometers and about no more than 810 micrometers;
  (c) 90% of the microgranule population has a volume-weighted particle size about no more than 1170 micrometers; or
  (d) a combination thereof, which can include some or all of (a) through (c) above.

In some embodiments, the secnidazole microgranule formulation may be mixed, stirred, or otherwise integrated into a food substance. In some embodiments, the food substance may be a liquid, semisolid, or soft food. In some embodiments, the food substance may include, but is not limited to applesauce, pudding, yogurt or the like. In some embodiments, integration of the secnidazole microgranule formulation into a food substance has a taste masking function. In some embodiments, the secnidazole microgranule formulation may be mixed, stirred, or otherwise integrated in a liquid, such as water, juice, milk or the like. In some embodiments, the at least one sexual partner of the subject may be a male or a female. In some embodiments, a single dose of a therapeutically effective amount of secnidazole or pharmaceutically acceptable salts thereof may be administered. In some embodiments, a single dose of a therapeutically effective amount of secnidazole or pharmaceutically acceptable salts thereof in a microgranule formulation may be administered. In some embodiments, multiple doses may be given at pre-determined intervals such as but not limited to once a week, bi-weekly, monthly, bimonthly for the duration of treatment. In some embodiment, the duration of treatment may be at least one week. In some embodiment, the duration of treatment may be at least one month. In some embodiments, the duration of treatment is about six months.

Some embodiments are directed to methods of treating vaginitis. In some embodiments, the vaginitis is trichomoniasis. Trichomoniasis is a genitourinary infection with the protozoan *Trichomonas vaginalis*. It is the most common non-viral sexually transmitted disease (STD) worldwide. Women are affected more often than men. Trichomoniasis is one of the three major causes of vaginal complaints among reproductive aged women, along with bacterial vaginosis and *candida* vulvovaginitis, and a cause of urethritis in men; however, the infection is often asymptomatic. In some embodiments, a method of treating trichomoniasis in a subject in need thereof comprises administering to the subject a therapeutically effective amount of secnidazole or pharmaceutically acceptable salts thereof in a microgranule formulation. In some embodiments, the secnidazole microgranule formulation may be suitable for oral administration. In some embodiments, the secnidazole microgranule formulation comprises a plurality of microgranules. In some embodiments, the plurality of microgranules are white to off-white in color. In some embodiments, the plurality of microgranules each have a particle size range of about 400 micrometers to about 841 micrometers.

In some embodiments, the plurality of microgranules has a volume-weighted particle size distribution within a microgranule population, wherein the volume-weighted particle size distribution as measured from a representative sample of the microgranule population includes:
  (a) 10% of the microgranule population has a volume-weighted particle size about no less than 470 micrometers;
  (b) 50% of the microgranule population has a volume-weighted particle size between about no less than 640 micrometers and about no more than 810 micrometers;
  (c) 90% of the microgranule population has a volume-weighted particle size about no more than 1170 micrometers; or
  d) a combination thereof, which can include some or all of (a) through (c) above.

In some embodiments, the secnidazole microgranule formulation may be mixed, stirred, or otherwise integrated into a food substance. In some embodiments, the food substance may be a liquid, semisolid or soft food. In some embodiments, the food substance may include, but is not limited to applesauce, pudding, yogurt or the like. In some embodiments, integration of the secnidazole microgranule formulation into a food substance has a taste masking function. In some embodiments, the secnidazole microgranule formulation may be mixed, stirred, or otherwise integrated in a liquid, such as water, juice, milk or the like.

In some embodiments, the subject is a human. In yet other embodiments, the subject is a human female. In some embodiments, the human female is of an age ranging from a postmenarachal adolescent to a premenopausal woman. In some embodiments, the subject is a pregnant human female.

In some embodiments, the subject is a female. In some embodiments, the subject is an otherwise healthy female. In some embodiments, the subject is a pregnant female. In some embodiments, the subject is an otherwise healthy pregnant female. In some embodiments, the subject is a female presenting with purulent malodorous discharge (associated with burning, pruritus, dysuria, frequency, lower abdominal pain), dyspareunia, burning postcoital bleeding, dyspareunia, dysuria, a thin green-yellow frothy discharge, vulvovaginal erythema (erythema of the vulva and vaginal mucosa), punctate hemorrhages, urethritis, cystitis, purulent vaginitis, sequamative inflammatory vaginitis, atrophic vaginitis, erosive lichen planus, an elevated vaginal pH (about 5.0 to about 6.0), and any combination thereof. In some embodiments, the subject is asymptomatic. In some embodiments, the subject is a female with confirmed trichomoniasis. In some embodiments, the diagnosis of *Trichomonas vaginalis* is confirmed by laboratory testing (including, but not limited to motile trichomonads on wet mount, positive culture, increase in polymorphonuclear leukocytes, positive nucleic acid amplification test, or positive rapid antigen, nucleic acid probe test cervical cytology or any combination thereof). Microscopy (such as, but not limited to culture on Diamond's medium) is a key step in the evaluation of vaginal discharge, and is often the first step in the diagnostic evaluation for trichomoniasis. Microscopy is convenient and low cost. In some embodiments, nucleic acid amplification tests (NAAT) can then be done for subjects with non-diagnostic (or negative) wet mounts. In some embodiments, if NAAT is not available, rapid diagnostic kits or culture are then performed. Additional laboratory tests include but are not limited to the APTIMA *Trichomonas vaginalis* assay; the APTIMA TV assay; the Amplicor assay (PCR assay for detection of *N. gonorrhoeae* and *C. trachomatis* that has been modified to detect *T. vaginalis* in vaginal/endocervical swabs or urine); NuSwab VG or any combination thereof; positive rapid antigen, nucleic acid probe test include but are not limited to the Affirm VP III Microbial Identification System; and the OSOM *Trichomonas* Rapid Test. In some embodiments, the subject is a female with suspected trichomoniasis. In some embodiments, suspected trichomoniasis is indicated by the presence of purulent malodorous discharge (associated with burning, pruritus, dysuria, frequency, lower abdominal pain), or dyspareunia, burning postcoital bleeding, dyspareunia, dysuria, a thin green-yellow frothy discharge, vulvovaginal erythema (erythema of the vulva and vaginal mucosa), punctate hemorrhages, urethritis, cystitis, purulent vaginitis, sequamative inflammatory vaginitis, atrophic vaginitis, erosive lichen planus, elevated vaginal pH (about 5.0 to about 6.0), and any combination thereof.

In some embodiments, a method of treating trichomoniasis in a subject comprises administering to the subject a single dose of a therapeutically effective amount of secnidazole in a microgranule formulation, wherein the secnidazole comprises about 1 g to about 2 g of the microgranule formulation. In some embodiments, the secnidazole microgranule formulation is co-administered with an additional compound selected from ethinyl estradiol (EE2), norethindrone (NET), or a combination thereof. In some embodiments, the secnidazole microgranule formulation is mixed into a liquid, semisolid, or soft food substance, such as but not limited to applesauce, yogurt, and pudding. In some embodiments, the amount of the food substance is about 4-6 ounces. In some embodiments, the secnidazole microgranule formulation may be mixed, stirred, or otherwise integrated in a liquid, such as water, juice, milk or the like.

In some embodiments, a method of treating trichomoniasis in a subject comprises administering to the subject a single dose of a secnidazole microgranule formulation that exhibits a maximum serum concentration ($C_{max}$) of between about 34.5 µg/ml and about 58.3 µg/ml. In some embodiments, a method of treating bacterial vaginosis in a subject comprises administering to the subject a single dose of a secnidazole microgranule formulation that exhibits a maximum serum concentration ($C_{max}$) of between about 17.4 µg/ml and about 26.5 µg/ml.

In some embodiments, a method of treating trichomoniasis in a subject comprises administering to the subject a single dose of a secnidazole microgranule formulation that exhibits a time to maximum plasma concentration ($T_{max}$) of about 3 hours to about 4.05 hours. In some embodiments, a method of treating trichomoniasis in a subject comprises administering to the subject a single dose of a secnidazole microgranule formulation that exhibits a time to maximum plasma concentration ($T_{max}$) of about 2 hours to about 6 hours.

In some embodiments, a method of treating trichomoniasis in a subject comprises co-administering to the subject a single dose of a therapeutically effective amount of secnidazole in a microgranule formulation and an additional compound selected from ethinyl estradiol (EE2), norethindrone (NET), or a combination thereof, wherein the secnidazole comprises about 1 g to about 2 g of the microgranule formulation. In some embodiments, the additional compound is co-administered on the same day as the secnidazole microgranule formulation. In some embodiments, the additional compound is administered on a different day than the secnidazole microgranule formulation. In some embodiments, the secnidazole microgranule formulation does not affect the contraceptive efficacy of the additional compound.

In some embodiments, a method of treating trichomoniasis in a subject further comprises determining a post treatment clinical outcome. In some embodiments, a post treatment clinical outcome is indicative of a clinical outcome responder. In some embodiments, a clinical outcome responder is a subject that is asymptomatic. In some embodiments, a clinical outcome responder is a subject with normal vaginal discharge, normal vaginal pH, normal laboratory testing results (including, but not limited to the absence of motile trichomonads on wet mount, negative culture, normal polymorphonuclear leukocytes, negative nucleic acid amplification test, negative rapid antigen, negative nucleic acid probe test, negative rapid diagnostic kits or culture, negative cervical cytology, or any combination thereof) after treatment with an oral microgranule formulation comprising about 1 grams to about 2 grams of secnidazole. In some embodiments, a clinical outcome responder is a subject with without purulent malodorous discharge (associated with burning, pruritus, dysuria, frequency, lower abdominal pain), or dyspareunia, burning postcoital bleeding, dyspareunia, dysuria, a thin green-yellow frothy discharge, vulvovaginal erythema (erythema of the vulva and vaginal mucosa), punctate hemorrhages, urethritis, cystitis, purulent vaginitis, sequamative inflammatory vaginitis, atrophic vaginitis, erosive lichen planus, elevated vaginal pH (about 5.0 to about 6.0), and any combination thereof. In some embodiments, a post-treatment clinical outcome is observable after about 24 hours after administration. In some embodiments, a post-treatment clinical outcome is observable after about 48 hours after administration. In some embodiments, a post-treatment clinical outcome is observable after about 72 hours after administration. In some embodiments, a post-treatment clinical outcome is observable after about 96 hours after administration. In some embodiments, a post-treatment clinical outcome is observable after about 120 hours after administration. In some embodiments, a post-treatment clinical outcome is observable after about 168 hours after administration. In some embodiments, a post-treatment clinical outcome is observable after about 7 days to about 10 days after administration. In some embodiments, a post-treatment clinical outcome is observable after about 11 days to about 20 days after administration. In some embodiments, a post-treatment clinical outcome is observable after about 21 days to about 30 days after administration.

In some embodiments, a method of treating trichomoniasis further comprises an alleviation of one or more symptoms of trichomoniasis within up to about three days after administration to the subject. In some embodiments, a method of treating trichomoniasis further comprises an alleviation of one or more symptoms of trichomoniasis within up to about three days after administration to the subject. In some embodiments, the one or more symptoms include, but are not limited to, purulent malodorous discharge (associated with burning, pruritus, dysuria, frequency, lower abdominal pain), or dyspareunia, burning postcoital bleeding, dyspareunia, dysuria, a thin green-yellow frothy discharge, vulvovaginal erythema (erythema of the vulva and vaginal mucosa), punctate hemorrhages, urethritis, cystitis, purulent vaginitis, sequamative inflammatory vaginitis, atrophic vaginitis, erosive lichen planus, elevated vaginal pH (about 5.0 to about 6.0), and any combination thereof. In some embodiments, alleviation refers to a lessening of the severity of one or more symptoms. In some embodiments, alleviation of one or more symptoms of trichomoniasis occurs within about 24 hours after administration. In some embodiments, alleviation of one or more symptoms of trichomoniasis occurs within about 48 hours after administration. In some embodiments, alleviation of one or more symptoms of trichomoniasis occurs within about 72 hours after administration to the subject. In some embodiments, alleviation of one or more symptoms of trichomoniasis occurs within about 96 hours after administration to the subject. In some embodiments, alleviation of one or more symptoms of trichomoniasis occurs within about 120 hours after administration to the subject. In some embodiments, alleviation of one or more symptoms of trichomoniasis occurs within about 168 hours after administration to the subject. In some embodiments, alleviation of one or more symptoms of trichomoniasis occurs within about 7 days to about 10 days after administration to the subject. In some embodiments, alleviation of one or more symptoms of trichomoniasis occurs within about 11 days to about 20 days after administration to the subject. In some embodiments, alleviation of one or more symptoms of trichomoniasis occurs within about 21 days to about 30 days after administration to the subject.

In some embodiments, a method of treating trichomoniasis further comprises a resolution of one or more symptoms of trichomoniasis within up to about seven days after administration to the subject. In some embodiments, a method of treating trichomoniasis further comprises a resolution of one or more symptoms of trichomoniasis within up to about seven days after administration to the subject. In some embodiments, the one or more symptoms include, but are not limited to, purulent malodorous discharge (associated with burning, pruritus, dysuria, frequency, lower abdominal pain), or dyspareunia, burning postcoital bleeding, dyspareunia, dysuria, a thin green-yellow frothy discharge, vulvovaginal erythema (erythema of the vulva and vaginal mucosa), punctate hemorrhages, urethritis, cystitis, purulent vaginitis, sequamative inflammatory vaginitis, atrophic vaginitis, erosive lichen planus, elevated vaginal pH (about 5.0 to about 6.0), and any combination thereof. In some embodiments, resolution of one or more symptoms of trichomoniasis occurs within about 24 hours after administration to the subject. In some embodiments, resolution of one or more symptoms of trichomoniasis occurs within about 48 hours after administration. In some embodiments, resolution of one or more symptoms of trichomoniasis occurs within about 72 hours after administration to the subject. In some embodiments, resolution of one or more symptoms of trichomoniasis occurs within about 96 hours after administration to the subject. In some embodiments, resolution of one or more symptoms of trichomoniasis occurs within about 120 hours after administration to the subject. In some embodiments, resolution of one or more symptoms of trichomoniasis occurs within about 168 hours after administration to the subject. In some embodiments, resolution of one or more symptoms of trichomoniasis occurs within about 7 days to about 10 days after administration to the subject. In some embodiments, resolution of one or more symptoms of trichomoniasis occurs within about 11 days to about 20 days after administration to the subject. In some embodiments, resolution of one or more symptoms of trichomoniasis occurs within about 21 days to about 30 days after administration to the subject.

In some embodiments, treatment of trichomoniasis with a single, 2 gram dose of secnidazole in a microgranule formulation results in better than expected efficacy compared with FDA approved drugs used in the treatment of trichomoniasis. In some embodiments, a single dose of 2 grams of secnidazole results in a better than expected efficacy compared with FDA approved drugs currently used in the treatment of trichomoniasis. In some embodiments, treatment of trichomoniasis with a single, 2 gram dose of secnidazole results in superior efficacy compared with FDA approved drugs used in the treatment of trichomoniasis. In some embodiments, a single dose of 2 grams of secnidazole results in superior efficacy compared with FDA drugs used in the treatment of trichomoniasis requiring a single dose during treatment.

In some embodiments, treatment of trichomoniasis with a single, 2 gram dose of secnidazole results in a better than expected safety profile compared with FDA approved drugs used in the treatment of trichomoniasis. In some embodiments, a single dose of 2 grams of secnidazole results in a better than expected safety profile compared with FDA approved drugs used in the treatment of trichomoniasis requiring multiple doses during treatment. In some embodiments, treatment of trichomoniasis with a single, 2 gram dose of secnidazole results in a superior safety profile compared with FDA approved drugs used in the treatment of trichomoniasis. In some embodiments, a single dose of 2 grams of secnidazole results in a superior safety profile compared with FDA approved drugs used in the treatment of trichomoniasis requiring a single dose during treatment.

In some embodiments, a method of treating trichomoniasis in a subject in need thereof further comprises administering to at least one of the subject's sexual partners, a therapeutically effective amount of secnidazole or pharmaceutically acceptable salts thereof in a microgranule formulation. In some embodiments, the secnidazole microgranule formulation may be suitable for oral administration. In some embodiments, the secnidazole microgranule formulation comprises a plurality of microgranules. In some embodiments, the plurality of microgranules are white to off-white in color. In some embodiments, the plurality of microgranules each have a particle size range of about 400 micrometers to about 841 micrometers.

In some embodiments, the plurality of microgranules has a volume-weighted particle size distribution within a microgranule population, wherein the volume-weighted particle size distribution as measured from a representative sample of the microgranule population includes:
 (a) 10% of the microgranule population has a volume-weighted particle size about no less than 470 micrometers;
 (b) 50% of the microgranule population has a volume-weighted particle size between about no less than 640 micrometers and about no more than 810 micrometers;
 (c) 90% of the microgranule population has a volume-weighted particle size about no more than 1170 micrometers; or
 (d) a combination thereof, which can include some or all of (a) through (c) above.

In some embodiments, the secnidazole microgranule formulation may be mixed, stirred, or otherwise integrated into a food substance. In some embodiments, the food substance may be a liquid, semisolid or soft food. In some embodiments, the food substance may include, but is not limited to applesauce, pudding, yogurt or the like. In some embodiments, integration of the secnidazole microgranule formulation into a food substance has a taste masking function. In some embodiments, the secnidazole microgranule formulation may be mixed, stirred, or otherwise integrated in a liquid, such as water, juice, milk or the like.

In some embodiments, the subject is a human. In yet other embodiments, the subject is a human female. In some embodiments, the human female is of an age ranging from a postmenarachal adolescent to a premenopausal woman. In some embodiments, the subject is a pregnant human female. In some embodiments, the at least one sexual partner of the subject may be a male or a female.

In some embodiments, a method of treating bacterial vaginosis and/or trichomoniasis in a subject in need thereof comprises administering to the subject a therapeutically effective amount of secnidazole or pharmaceutically acceptable salts thereof in a microgranule formulation. In some embodiments, the secnidazole microgranule formulation may be suitable for oral administration. In some embodiments, the secnidazole microgranule formulation comprises a plurality of microgranules. In some embodiments, the plurality of microgranules are white to off-white in color. In some embodiments, the plurality of microgranules each have a particle size range of about 400 micrometers to about 841 micrometers. In some embodiments, the plurality of microgranules has a volume-weighted particle size distribution within a microgranule population, wherein the volume-weighted particle size distribution as measured from a representative sample of the microgranule population includes:
  (a) 10% of the microgranule population has a volume-weighted particle size about no less than 470 micrometers;
  (b) 50% of the microgranule population has a volume-weighted particle size between about no less than 640 micrometers and about no more than 810 micrometers;
  (c) 90% of the microgranule population has a volume-weighted particle size about no more than 1170 micrometers; or
  (d) a combination thereof, which can include sore or all (a) through (c) above.

In some embodiments, the secnidazole microgranule formulation may be mixed, stirred, or otherwise integrated into a food substance. In some embodiments, the food substance may be a liquid, semisolid or soft food. In some embodiments, the food substance may include, but is not limited to applesauce, pudding, yogurt or the like. In some embodiments, integration of the secnidazole microgranule formulation into a food substance has a taste masking function. In some embodiments, the secnidazole microgranule formulation may be mixed, stirred, or otherwise integrated in a liquid, such as water, juice, milk or the like.

In some embodiments, the subject is a human. In yet other embodiments, the subject is a human female. In some embodiments, the human female is of an age ranging from a postmenarachal adolescent to a premenopausal woman. In some embodiments, the subject is a pregnant human female.

In some embodiments, the subject is a female. In some embodiments, the subject is an otherwise healthy female. In some embodiments, the subject is a pregnant female. In some embodiments, the subject is an otherwise healthy pregnant female. In some embodiments, the subject is a female having had 3 or fewer bacterial vaginosis infections in the past 12 months. In some embodiments, the subject is a female having had 4 or more bacterial vaginosis infections in the past twelve months. In some embodiments, the subject is a female with recurring bacterial vaginosis. In some embodiments, a subject with recurring bacterial vaginosis is a subject with 4 or more bacterial vaginosis infections within a twelve-month period. In some embodiments, the subject is a female with frequent bacterial vaginosis infections. In some embodiments, a female with frequent bacterial vaginosis infections is a female with 4 or more bacterial vaginosis infections within a twelve-month period. In some embodiments, the subject is a female presenting with an off-white (milky or gray), thin, homogeneous vaginal discharge, vaginal pH greater than or equal to 4.7, presence of clue cells of greater than or equal to 20% of the total epithelial cells on microscopic examination of a vaginal saline wet mount, a positive 10% KOH Whiff test or a combination thereof. In some embodiments, the subject is a female presenting with an off-white (milky or gray), thin, homogeneous vaginal discharge, vaginal pH greater than or equal to 4.7, the presence of clue cells of greater than or equal to 20% of the total epithelial cells on microscopic examination of a vaginal saline wet mount, and a positive 10% KOH Whiff test. In some embodiments, the subject is a female with confirmed bacterial vaginosis. In some embodiments, bacterial vaginosis is confirmed by the presence of four (4) Amsel criteria parameters selected from an off-white (milky or gray), thin, homogeneous vaginal discharge, vaginal pH greater than or equal to 4.7, the presence of clue cells of greater than or equal to 20% of the total epithelial cells on microscopic examination of a vaginal saline wet mount, a positive 10% KOH Whiff test and a gram stain slide Nugent score equal to, or higher than four (4) on bacterial analysis of vaginal samples. In some embodiments, the subject is a female with suspected bacterial vaginosis. In some embodiments, suspected bacterial vaginosis is indicated by the presence of four (4) Amsel criteria parameters selected from an off-white (milky or gray), thin, homogeneous vaginal discharge, vaginal pH greater than or equal to 4.7, the presence of clue cells of greater than or equal to 20% of the total epithelial cells on microscopic examination of a vaginal saline wet mount, and a positive 10% KOH Whiff test. In some embodiments, the subject is a female presenting with an off-white (milky or gray), thin, homogeneous vaginal discharge, odor, or a combination thereof. In some embodiments, the subject is a female presenting with purulent malodorous discharge (associated with burning, pruritus, dysuria, frequency, lower abdominal pain), dyspareunia, burning postcoital bleeding, dyspareunia, dysuria, a thin green-yellow frothy discharge, vulvovaginal erythema (erythema of the vulva and vaginal mucosa), punctate hemorrhages, urethritis, cystitis, purulent vaginitis, sequamative inflammatory vaginitis, atrophic vaginitis, erosive lichen planus, an elevated vaginal pH (about 5.0 to about 6.0), and any combination thereof. In some embodiments, the subject is asymptomatic. In some embodiments, the subject is a female with confirmed trichomoniasis. In some embodiments, the diagnosis of *Trichomonas vaginalis* is confirmed by laboratory testing (including, but not limited to motile trichomonads on wet mount, positive culture, increase in polymorphonuclear leukocytes, positive nucleic acid amplification test, or positive rapid antigen, nucleic acid probe test cervical cytology or any combination thereof). Microscopy (such as, but not limited to culture on Diamond's medium) is a key step in the evaluation of vaginal discharge, and is often the first step in the diagnostic evaluation for trichomoniasis. Microscopy is convenient and low cost. In some embodiments, nucleic acid amplification tests (NAAT) can then be done for subjects with non-diagnostic (or negative) wet mounts. In some embodiments, if NAAT is not available, rapid diagnostic kits or culture are then performed. Additional laboratory tests include but are not limited to the APTIMA *Trichomonas vaginalis* assay, the APTIMA TV assay; the Amplicor assay (PCR assay for detection of *N. gonorrhoeae* and *C. trachomatis* that has been modified to detect *T. vaginalis* in vaginal/endocervical swabs or urine); NuSwab VG or any combination thereof; positive rapid antigen, nucleic acid probe test include but are not limited to the Affirm VP III Microbial Identification System, and the OSOM *Trichomonas* Rapid Test. In some embodiments, the subject is a female with suspected trichomoniasis. In some embodiments, suspected trichomoniasis is indicated by presence of purulent malodorous discharge (associated with burning, pruritus, dysuria, frequency, lower abdominal pain), or dyspareunia, burning postcoital bleeding, dyspareunia, dysuria, a thin green-yellow frothy discharge, vulvovaginal erythema (erythema of the vulva and vaginal mucosa), punctate hemorrhages, urethritis, cystitis, purulent vaginitis, sequamative inflammatory vaginitis, atrophic vaginitis, erosive lichen planus, elevated vaginal pH (about 5.0 to about 6.0), and any combination thereof. In some embodiments, the subject is suspected of having both bacterial vaginosis and/or trichomoniasis. In some embodiments, a diagnosis of bacterial vaginosis and/or trichomoniasis is not confirmed.

In some embodiments, a method of treating bacterial vaginosis and/or trichomoniasis in a subject comprises administering to the subject a single dose of a therapeutically effective amount of secnidazole in a microgranule formulation, wherein the secnidazole comprises about 1 g to about 2 g of the microgranule formulation. In some embodiments, the secnidazole microgranule formulation is mixed into a liquid, semisolid or soft food substance, such as but not limited to applesauce yogurt and pudding. In some embodiments, the amount of the food substance is about 4-6 ounces. In some embodiments, the secnidazole microgranule formulation may be mixed, stirred, or otherwise integrated in a liquid, such as water, juice, milk or the like.

In some embodiments, a method of treating bacterial vaginosis and/or trichomoniasis in a subject comprises administering to the subject a single dose of a secnidazole microgranule formulation that exhibits a maximum serum concentration ($C_{max}$) of between about 34.5 µg/ml and about 58.3 µg/ml. In some embodiments, a method of treating bacterial vaginosis in a subject comprises administering to the subject a single dose of a secnidazole microgranule formulation that exhibits a maximum serum concentration ($C_{max}$) of between about 17.4 µg/ml and about 26.5 µg/ml.

In some embodiments, a method of treating bacterial vaginosis and/or trichomoniasis in a subject comprises administering to the subject a single dose of a secnidazole microgranule formulation that exhibits a time to maximum plasma concentration ($T_{max}$) of about 3 hours to about 4.05 hours. In some embodiments, a method of treating bacterial vaginosis in a subject comprises administering to the subject a single dose of a secnidazole microgranule formulation that exhibits a time to maximum plasma concentration ($T_{max}$) of about 2 hours to about 6 hours.

In some embodiments, a method of treating bacterial vaginosis and/or trichomoniasis in a subject comprises co-administering to the subject a single dose of a therapeutically effective amount of secnidazole in a microgranule formulation and an additional compound selected from ethinyl estradiol (EE2), norethindrone (NET), or a combination thereof, wherein the secnidazole comprises about 1 g to about 2 g of the microgranule formulation. In some embodiments, the additional compound is co-administered on the same day as the secnidazole microgranule formulation. In some embodiments, the additional compound is administered on a different day than the secnidazole microgranule formulation. In some embodiments, the secnidazole microgranule formulation does not affect the contraceptive efficacy of the additional compound.

In some embodiments, a method of treating bacterial vaginosis and/or trichomoniasis in a subject further comprises determining a post treatment clinical outcome. In some embodiments, a post treatment clinical outcome is indicative of a clinical outcome responder. Some embodiments further comprise determining a post-treatment clinical outcome. In some embodiments, a post-treatment clinical outcome of clinical cure is defined as a clinical outcome responder. In some embodiments, a clinical outcome responder is a subject with normal vaginal discharge, a negative KOH Whiff test, and clue cells less than or equal to 20% of the total epithelial cells on microscopic examination of a vaginal saline wet mount after treatment with a microgranule formulation comprising about 1 grams to about 2 grams of secnidazole. In some embodiments, a clinical outcome responder has a gram stain slide Nugent score of less than four (4) after treatment with a single dose of secnidazole. In yet other embodiments, a clinical outcome responder is a subject with normal vaginal discharge, a negative KOH Whiff test, clue cells less than 20% of total epithelial cells, and a gram stain slide Nugent score of less than four (4) after treatment with a single dose of secnidazole. In some embodiments, a clinical outcome responder has a gram stain slide Nugent score of less than four (4) after treatment with a 2 gram single dose of secnidazole. In yet other embodiments, a clinical outcome responder is a subject with normal vaginal discharge, a negative KOH Whiff test, clue cells less than 20% of total epithelial cells, and a gram stain slide Nugent score of less than four (4) after treatment with a 2 gram single dose of secnidazole. In some embodiments, a post-treatment clinical outcome is observable after about 24 hours after administration. In some embodiments, a post-treatment clinical outcome is observable after about 48 hours after administration. In some embodiments, a post-treatment clinical outcome is observable after about 72 hours after administration. In some embodiments, a post-treatment clinical outcome is observable after about 96 hours after administration. In some embodiments, a post-treatment clinical outcome is observable after about 120 hours after administration. In some embodiments, a post-treatment clinical outcome is observable after about 168 hours after administration. In some embodiments, a post-treatment clinical outcome is observable after about 7 days to about 10 days after administration. In some embodiments, a post-treatment clinical outcome is observable after about 11 days to about 20 days after administration. In some embodiments, a post-treatment clinical outcome is observable after about 21 days to about 30 days after administration. In some embodiments, a method of treating trichomoniasis in a subject further comprises determining a post treatment clinical outcome. In some embodiments, a post treatment clinical outcome is indicative of a clinical outcome responder. In some embodiments, a clinical outcome responder is a subject that is asymptomatic. In some embodiments, a clinical outcome responder is a subject with normal vaginal discharge, normal vaginal pH, normal laboratory testing results (including, but not limited to the absence of motile trichomonads on wet mount, negative culture, normal polymorphonuclear leukocytes, negative nucleic acid amplification test, negative rapid antigen, negative nucleic acid probe test, negative rapid diagnostic kits or culture, negative cervical cytology, or any combination thereof) after treatment with an oral microgranule formulation comprising about 1 grams to about 2 grams of secnidazole. In some embodiments, a clinical outcome responder is a subject with without purulent malodorous discharge (associated with burning, pruritus, dysuria, frequency, lower abdominal pain), or dyspareunia, burning postcoital bleeding, dyspareunia, dysuria, a thin green-yellow frothy discharge, vulvovaginal erythema (erythema of the vulva and vaginal mucosa), punctate hemorrhages, urethritis, cystitis, purulent vaginitis, sequamative inflammatory vaginitis, atrophic vaginitis, erosive lichen planus, elevated vaginal pH (about 5.0 to about 6.0), and any combination thereof. In some embodiments, a post-treatment clinical outcome is observable after about 24 hours after administration. In some embodiments, a post-treatment clinical outcome is observable after about 48 hours after administration. In some embodiments, a post-treatment clinical outcome is observable after about 72 hours after administration. In some embodiments, a post-treatment clinical outcome is observable after about 96 hours after administration. In some embodiments, a post-treatment clinical outcome is observable after about 120 hours after administration. In some embodiments, a post-treatment clinical outcome is observable after about 168 hours after administration. In some embodiments, a post-treatment clinical outcome is observable after about 7 days to about 10 days after administration. In some embodiments, a post-treatment clinical outcome is observable after about 11 days to about 20 days after administration. In some embodiments, a post-treatment clinical outcome is observable after about 21 days to about 30 days after administration.

In some embodiments, a method of treating bacterial vaginosis and/or trichomoniasis further comprises an alleviation of one or more symptoms of bacterial vaginosis within up to about three days after administration to the subject. In some embodiments, a method of treating bacterial vaginosis further comprises an alleviation of one or more symptoms of bacterial vaginosis within up to about three days after administration to the subject. In some embodiments, the one or more symptoms include, but are not limited to, abnormal vaginal odor, abnormal vaginal discharge or a combination thereof. In some embodiments, alleviation refers to a lessening of the severity of one or more symptoms. In some embodiments, alleviation of one or more symptoms of bacterial vaginosis occurs within about 24 hours after administration. In some embodiments, alleviation of one or more symptoms of bacterial vaginosis occurs within about 48 hours after administration. In some embodiments, alleviation of one or more symptoms of bacterial vaginosis occurs within about 72 hours after administration to the subject. In some embodiments, alleviation of one or more symptoms of bacterial vaginosis occurs within about 96 hours after administration to the subject. In some embodiments, alleviation of one or more symptoms of bacterial vaginosis occurs within about 120 hours after administration to the subject. In some embodiments, alleviation of one or more symptoms of bacterial vaginosis occurs within about 168 hours after administration to the subject. In some embodiments, alleviation of one or more symptoms of bacterial vaginosis occurs within about 7 days to about 10 days after administration to the subject. In some embodiments, alleviation of one or more symptoms of bacterial vaginosis occurs within about 11 days to about 20 days after administration to the subject. In some embodiments, alleviation of one or more symptoms of bacterial vaginosis occurs within about 21 days to about 30 days after administration to the subject. In some embodiments, a method of treating trichomoniasis in a subject further comprises determining a post treatment clinical outcome. In some embodiments, a post treatment clinical outcome is indicative of a clinical outcome responder. In some embodiments, a clinical outcome responder is a subject that is asymptomatic. In some embodiments, a clinical outcome responder is a subject with normal vaginal discharge, normal vaginal pH, normal laboratory testing results (including, but not limited to the absence of motile trichomonads on wet mount, negative culture, normal polymorphonuclear leukocytes, negative nucleic acid amplification test, negative rapid antigen, negative nucleic acid probe test, negative rapid diagnostic kits or culture, negative cervical cytology, or any combination thereof) after treatment with an oral microgranule formulation comprising about 1 grams to about 2 grams of secnidazole. In some embodiments, a clinical outcome responder is a subject with without purulent malodorous discharge (associated with burning, pruritus, dysuria, frequency, lower abdominal pain), or dyspareunia, burning postcoital bleeding, dyspareunia, dysuria, a thin green-yellow frothy discharge, vulvovaginal erythema (erythema of the vulva and vaginal mucosa), punctate hemorrhages, urethritis, cystitis, purulent vaginitis, sequamative inflammatory vaginitis, atrophic vaginitis, erosive lichen planus, elevated vaginal pH (about 5.0 to about 6.0), and any combination thereof. In some embodiments, a post-treatment clinical outcome is observable after about 24 hours after administration. In some embodiments, a post-treatment clinical outcome is observable after about 48 hours after administration. In some embodiments, a post-treatment clinical outcome is observable after about 72 hours after administration. In some embodiments, a post-treatment clinical outcome is observable after about 96 hours after administration. In some embodiments, a post-treatment clinical outcome is observable after about 120 hours after administration. In some embodiments, a post-treatment clinical outcome is observable after about 168 hours after administration. In some embodiments, a post-treatment clinical outcome is observable after about 7 days to about 10 days after administration. In some embodiments, a post-treatment clinical outcome is observable after about 11 days to about 20 days after administration. In some embodiments, a post-treatment clinical outcome is observable after about 21 days to about 30 days after administration.

In some embodiments, a method of treating bacterial vaginosis and/or trichomoniasis further comprises a resolution of one or more symptoms of bacterial vaginosis within up to about seven days after administration to the subject. In some embodiments, a method of treating bacterial vaginosis further comprises a resolution of one or more symptoms of bacterial vaginosis within up to about seven days after administration to the subject. In some embodiments, the one or more symptoms include, but are not limited to, abnormal vaginal odor, abnormal vaginal discharge or a combination thereof. In some embodiments, resolution of one or more symptoms of bacterial vaginosis occurs within about 24 hours after administration to the subject. In some embodiments, resolution of one or more symptoms of bacterial vaginosis occurs within about 48 hours after administration. In some embodiments, resolution of one or more symptoms of bacterial vaginosis occurs within about 72 hours after administration to the subject. In some embodiments, resolution of one or more symptoms of bacterial vaginosis occurs within about 96 hours after administration to the subject. In some embodiments, resolution of one or more symptoms of bacterial vaginosis occurs within about 120 hours after administration to the subject. In some embodiments, resolution of one or more symptoms of bacterial vaginosis occurs within about 168 hours after administration to the subject. In some embodiments, resolution of one or more symptoms of bacterial vaginosis occurs within about 7 days to about 10 days after administration to the subject. In some embodiments, resolution of one or more symptoms of bacterial vaginosis occurs within about 11 days to about 20 days after administration to the subject. In some embodiments, resolution of one or more symptoms of bacterial vaginosis occurs within about 21 days to about 30 days after administration to the subject. In some embodiments, a method of treating trichomoniasis further comprises a resolution of one or more symptoms of trichomoniasis within up to about seven days after administration to the subject. In some embodiments, a method of treating trichomoniasis further comprises a resolution of one or more symptoms of trichomoniasis within up to about seven days after administration to the subject. In some embodiments, the one or more symptoms include, but are not limited to, purulent malodorous discharge (associated with burning, pruritus, dysuria, frequency, lower abdominal pain), or dyspareunia, burning postcoital bleeding, dyspareunia, dysuria, a thin green-yellow frothy discharge, vulvovaginal erythema (erythema of the vulva and vaginal mucosa), punctate hemorrhages, urethritis, cystitis, purulent vaginitis, sequamative inflammatory vaginitis, atrophic vaginitis, erosive lichen planus, elevated vaginal pH (about 5.0 to about 6.0), and any combination thereof. In some embodiments, resolution of one or more symptoms of trichomoniasis occurs within about 24 hours after administration to the subject. In some embodiments, resolution of one or more symptoms of trichomoniasis occurs within about 48 hours after administration. In some embodiments, resolution of one or more symptoms of trichomoniasis occurs within about 72 hours after administration to the subject. In some embodiments, resolution of one or more symptoms of trichomoniasis occurs within about 96 hours after administration to the subject. In some embodiments, resolution of one or more symptoms of trichomoniasis occurs within about 120 hours after administration to the subject. In some embodiments, resolution of one or more symptoms of trichomoniasis occurs within about 168 hours after administration to the subject. In some embodiments, resolution of one or more symptoms of trichomoniasis occurs within about 7 days to about 10 days after administration to the subject. In some embodiments, resolution of one or more symptoms of trichomoniasis occurs within about 11 days to about 20 days after administration to the subject. In some embodiments, resolution of one or more symptoms of trichomoniasis occurs within about 21 days to about 30 days after administration to the subject.

This invention and embodiments illustrating the method and materials used may be further understood by reference to the following non-limiting examples.

EXAMPLES

Example 1

This study evaluated the safety and pharmacokinetics (PK) of a 1 g or 2 g dose of a new microgranule formulation (formulation shown in Table 2) for SYM-1219, a 5-nitroimidazole being developed for the treatment of women with bacterial vaginosis (BV).

TABLE 2

Composition of SYM-1219 Drug Product

| Component | Function | Quality Standard | Quantity, mg/1 g Dose | Quantity, mg/2 g Dose |
|---|---|---|---|---|
| Secnidazole | Active Ingredient | Manufacturer's specifications | 1000.00 | 2000.00 |
| Sugar Spheres (size 35-40 mesh) | Inert core | National Formulary (NF) | 940.00 | 1880.00 |
| Povidone (Plasdone K-29/32) | Dispersion and binding | USP | 100.82 | 201.63 |
| Polyethylene Glycol 4000 | Seal coating | NF | 41.50 | 83.00 |
| Eudragit NE30D (Ethyl Acrylate-Methyl Methacrylate Copolymer) | Modified release coating | NF | 138.30 | 273.60 |
| Talc | Anti-tacking agent | USP | 138.30 | 273.60 |
| Total | | | 2365.00 | 4730.00 |

Methods: 28 healthy female subjects (14/group) ages 18-65 years were randomized to receive a single oral dose of either 1 gram or 2 grams of SYM-1219, mixed into 4 oz. of applesauce. Serial blood samples were collected over 168 hours to determine SYM-1219 plasma concentrations. A non-compartmental analysis was performed and the pharmacokinetics (PK) parameters for each treatment group are reported. Safety was evaluated by recording adverse events, vital signs, echocardiograms (ECGs) and laboratory tests.

Results: All subjects (N=28) completed the study and were evaluable for PK and safety. Table 2 below discloses the plasma pharmacokinetics of SYM-1219 (1 g or 2 g) administered according to methods described in this Example to fasted healthy female subjects. Table 4 below discloses the urine pharmacokinetics of SYM-1219 (1 g or 2 g) administered according to methods described in this Example to fasted healthy female subjects. FIG. 1 illustrates the mean (+SD) SYM-1219 plasma concentration (μg/mL) for the 1 g dose (circle markers) and the 2 g dose (triangle markers) over time.

The PK of SYM-1219 was consistent between individuals, as demonstrated by low coefficients of variation (% CV) estimates. Mean maximum concentrations were 22.6 mcg/mL for the 1 g dose and 45.4 mcg/mL for the 2 g dose and were achieved by approximately 4 hrs. in both dose groups. Exposure estimates (AUCinf) were 619 mcg*hr./mL for the 1 g dose and 1331 mcg*hr./mL for the 2 g dose. The pharmacokinetics of SYM-1219 was dose proportional when comparing the 1 and 2 g doses. The intersubject variability was low (<20% CV) for $C_{max}$ and AUC. Urinary excretion of unchanged SYM-1219 accounted for 13.6% (1 g dose) and 15.3% (2 g dose) of the administered dose. The amount excreted into the urine increased in proportion to dose. Renal clearance was similar after 1 g and 2 g doses and the renal clearance is only a small percentage (i.e., <5%) of the glomerular filtration rate typically found in healthy subjects with normal renal function.

SYM-1219 was safe and well-tolerated. The most common adverse events were headache and nausea. All adverse events were mild and resolved without sequelae. There were no significant changes in vital signs, electrocardiogram (ECG) or laboratory parameters.

TABLE 3

Plasma Pharmacokinetics of SYM-1219 After a Single Oral Dose Administered to Fasted Healthy Female Subjects (Part A) Pharmacokinetic Population

| Parameter | SYM-1219 1 gram (N = 14) | SYM-1219 2 grams (N = 14) |
|---|---|---|
| $C_{max}$ (µg/mL) | | |
| n | 14 | 14 |
| Mean (SD) | 22.62 (2.871) | 45.43 (7.642) |
| % CV | 12.69 | 16.82 |
| Geometric Mean (SD) | 22.45 (2.938) | 44.84 (7.467) |
| Median | 22.75 | 45.05 |
| Min, Max | 17.4, 26.5 | 34.5, 58.3 |
| $T_{max}$ (h) | | |
| n | 14 | 14 |
| Median | 3.060 | 4.000 |
| Min, Max | 2.00, 6.00 | 3.00, 4.05 |
| $AUC_{0-t}$ (h*µg/mL) | | |
| n | 14 | 14 |
| Mean (SD) | 609.66 (96.685) | 1322.40 (230.256) |
| % CV | 15.86 | 17.41 |
| Geometric Mean (SD) | 602.94 (92.067) | 1305.35 (214.383) |
| Median | 587.42 | 1290.41 |
| Min, Max | 487.6, 832.5 | 1048.5, 1899.5 |
| $AUC_{0-\infty}$ (h*µg/mL) | | |
| n | 14 | 14 |
| Mean (SD) | 618.89 (98.093) | 1331.63 (230.159) |
| % CV | 15.85 | 17.28 |
| Geometric Mean (SD) | 612.09 (93.248) | 1314.74 (214.081) |
| Median | 595.25 | 1299.10 |
| Min, Max | 498.5, 847.0 | 1055.1, 1911.9 |
| $t_{1/2}$ (h) | | |
| n | 14 | 14 |
| Mean (SD) | 17.05 (1.611) | 16.86 (2.649) |
| Median | 16.79 | 17.13 |
| Min, Max | 14.7, 20.4 | 11.3, 20.4 |
| λz (1/h) | | |
| n | 14 | 14 |
| Mean (SD) | 0.04099 (0.003757) | 0.04220 (0.007544) |
| Median | 0.04129 | 0.04047 |
| Min, Max | 0.0339, 0.0471 | 0.0340, 0.0613 |

Source: Table 14.1.2.4, Listing 16.2.1.11.2

TABLE 4

Urine Pharmacokinetics of SYM-1219 After a Single Oral Dose Administered to Fasted Healthy Female Subjects (Part A) Pharmacokinetic Population

| Parameter | SYM-1219 1 gram (N = 14) | SYM-1219 2 grams (N = 14) |
|---|---|---|
| $Ae_{0-168}$ (g) | | |
| n | 14 | 14 |
| Mean (SD) | 0.136 (0.0238) | 0.306 (0.0711) |
| % CV | 17.478 | 23.234 |
| Geometric Mean (SD) | 0.134 (0.0241) | 0.300 (0.0602) |
| Median | 0.140 | 0.299 |
| Min, Max | 0.10, 0.18 | 0.22, 0.52 |
| CLr (mL/min) | | |
| n | 14 | 14 |
| Mean (SD) | 3.742 (0.8255) | 3.935 (1.0568) |
| % CV | 22.060 | 26.859 |
| Geometric Mean (SD) | 3.650 (0.8701) | 3.801 (1.0532) |
| Median | 3.965 | 3.962 |
| Min, Max | 2.37, 4.89 | 2.23, 6.19 |
| % FE | | |
| n | 14 | 14 |
| Mean (SD) | 13.602 (2.3773) | 15.300 (3.5549) |
| % CV | 17.478 | 23.234 |
| Geometric Mean (SD) | 13.403 (2.4100) | 14.991 (3.0081) |
| Median | 13.981 | 14.943 |
| Min, Max | 10.19, 17.56 | 11.03, 26.20 |

Source: Table 14.1.2.5, Listing 16.2.1.12.1

Conclusions: This study characterized the single dose PK of a 1 g and 2 g dose of a new microgranule formulation of a 5-nitroimidazole, SYM-1219. SYM-1219 was safe and well-tolerated. The consistent PK and resulting exposure, with low variability between subjects, makes this a promising new therapeutic option. Ongoing studies will further evaluate the safety and efficacy of SYM-1219 for the treatment of women with BV.

Example 2

Background: This study evaluated the effect of a single 2 g dose of SYM-1219, a new microgranule formulation of a 5-nitroimidazole in development to treat women with bacterial vaginosis, on the pharmacokinetics (PK) of ethinyl estradiol (EE2) and norethindrone (NET).

Methods: Fifty-four (54) healthy female subjects, ages 18-65, received EE2/NET alone and in combination, where SYM-1219+EE2/NET were co-administered on Day 1 (Group B1; N=27) or SYM-1219 on Day 1 and EE2/NET on Day 2 (Group B2; N=27). Serial blood samples were drawn to measure plasma concentrations of EE2/NET. A non-compartmental analysis was performed and the PK parameters for each treatment group are reported. Safety was evaluated by recording of adverse events, vital signs, ECGs and standard laboratory tests.

Figure 2:
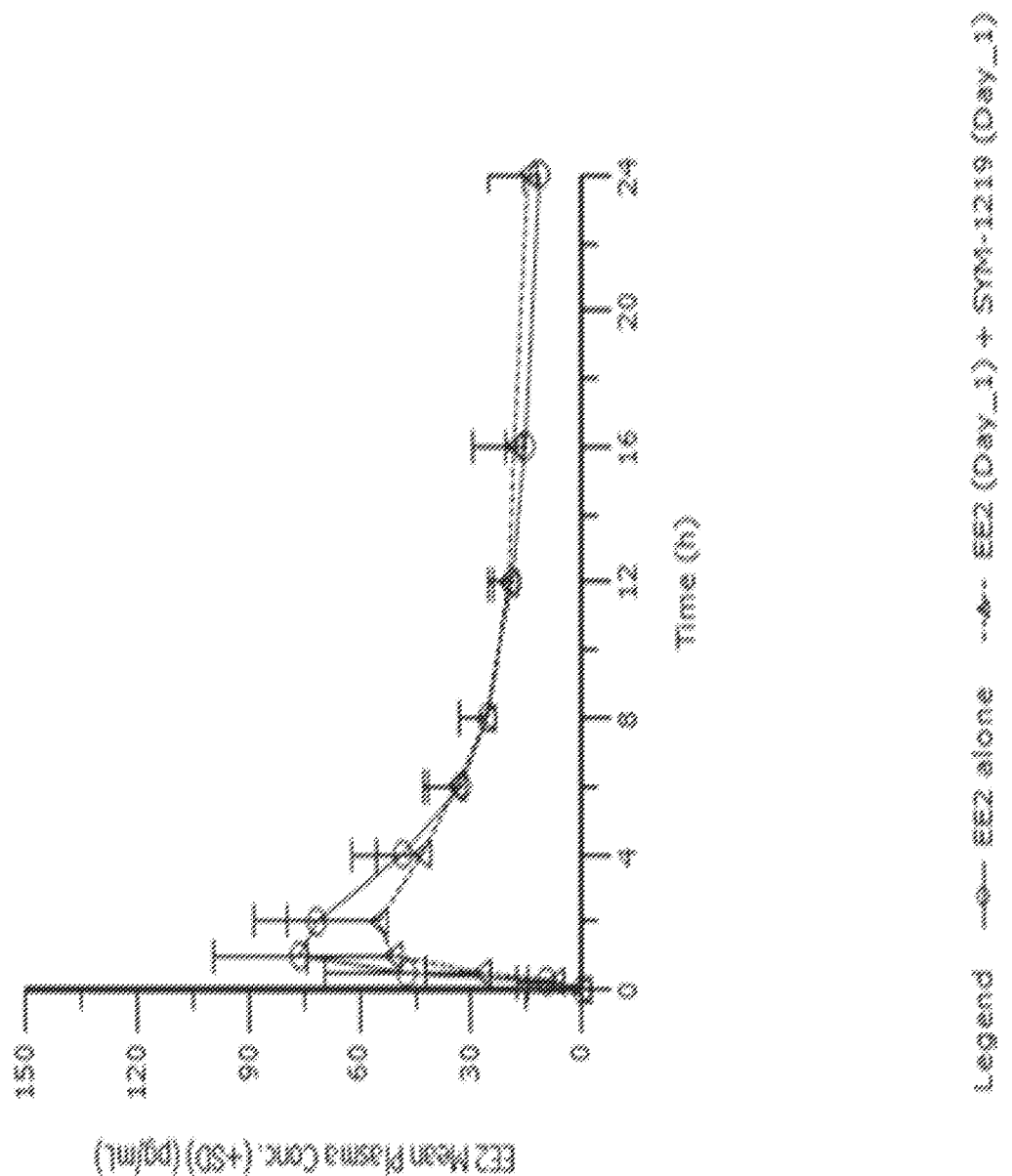
FIG. 2 illustrates the mean (±SD) EE2 plasma concentrations (pg/mL) for Group B1 over time where (1) EE2 was administered alone (circle markers) on Day 1 of Period 1; and (2) EE2 was administered in conjunction with 2 gram microgranule formulation Secnidazole (SYM-1219) on Day 1 of Period 2 (triangle markers).
Figure 3:
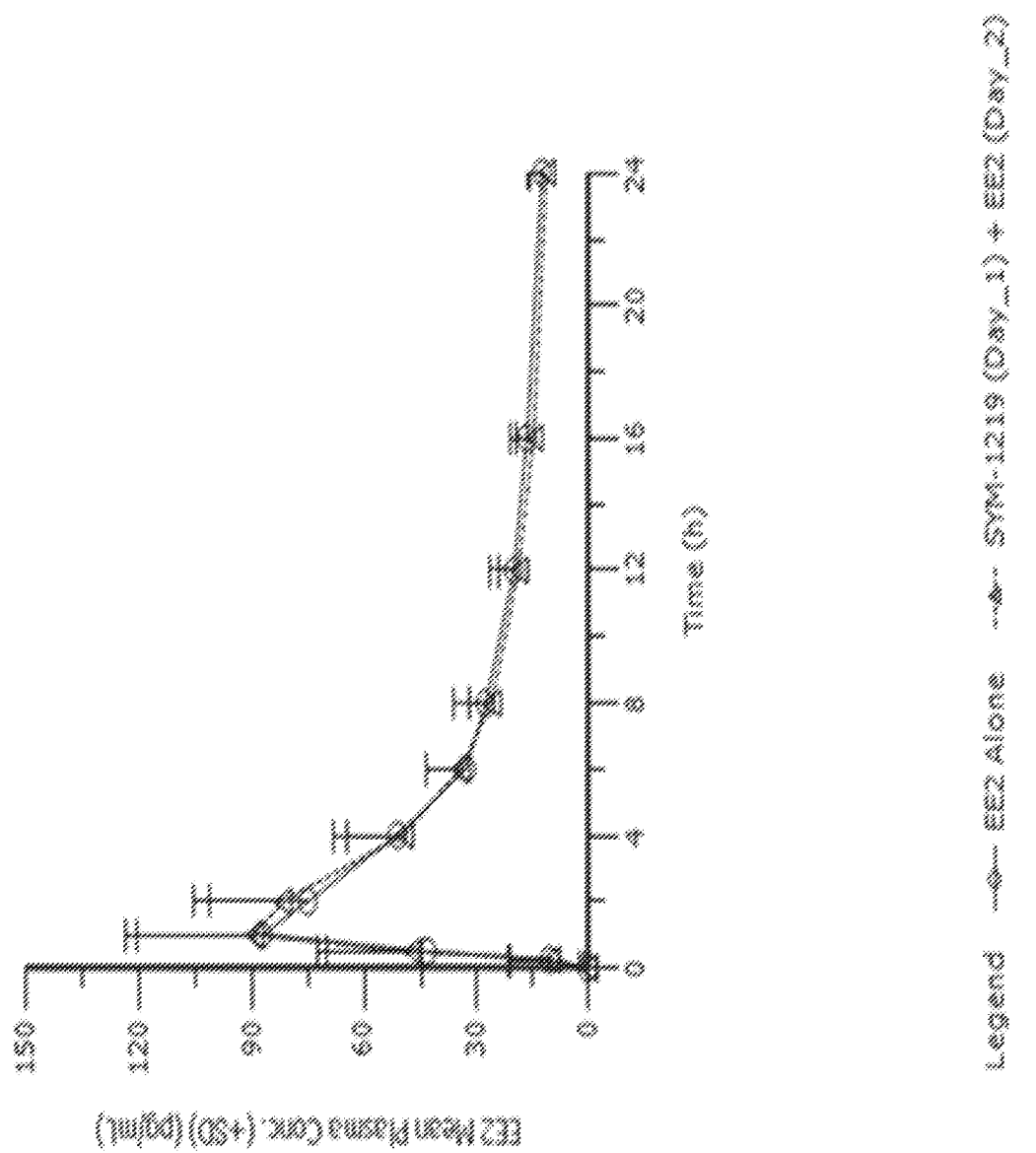
FIG. 3 illustrates the mean (±SD) EE2 plasma concentrations (pg/mL) for Group B2 over time where (1) EE2 was administered alone (circle markers) on Day 1 of Period 1; and (2) 2 gram microgranule formulation SYM-1219 was administered on Day 1 of Period 2 and EE2 was administered on Day 2 of Period 2 (triangle markers).
Figure 4:
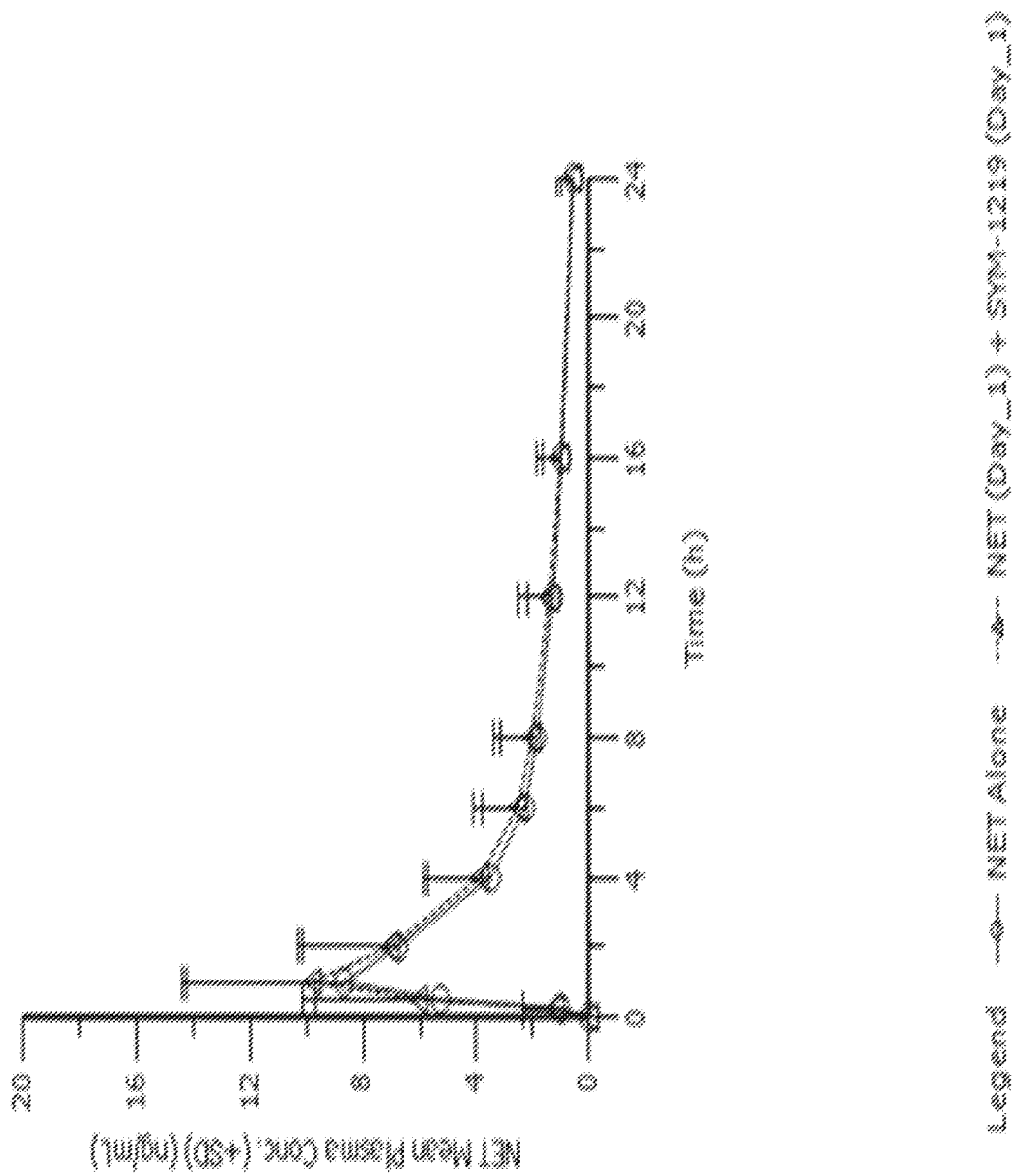
FIG. 4 illustrates the mean (±SD) NET plasma levels (ng/mL) for Group B1 over time where (1) NET alone was administered on Day 1 of Period 1 (circle markers), and (2) NET followed by 2 gram microgranule formulation of SYM-1219 was administered on Day 1 of Period 2 (triangle markers).
Figure 5:
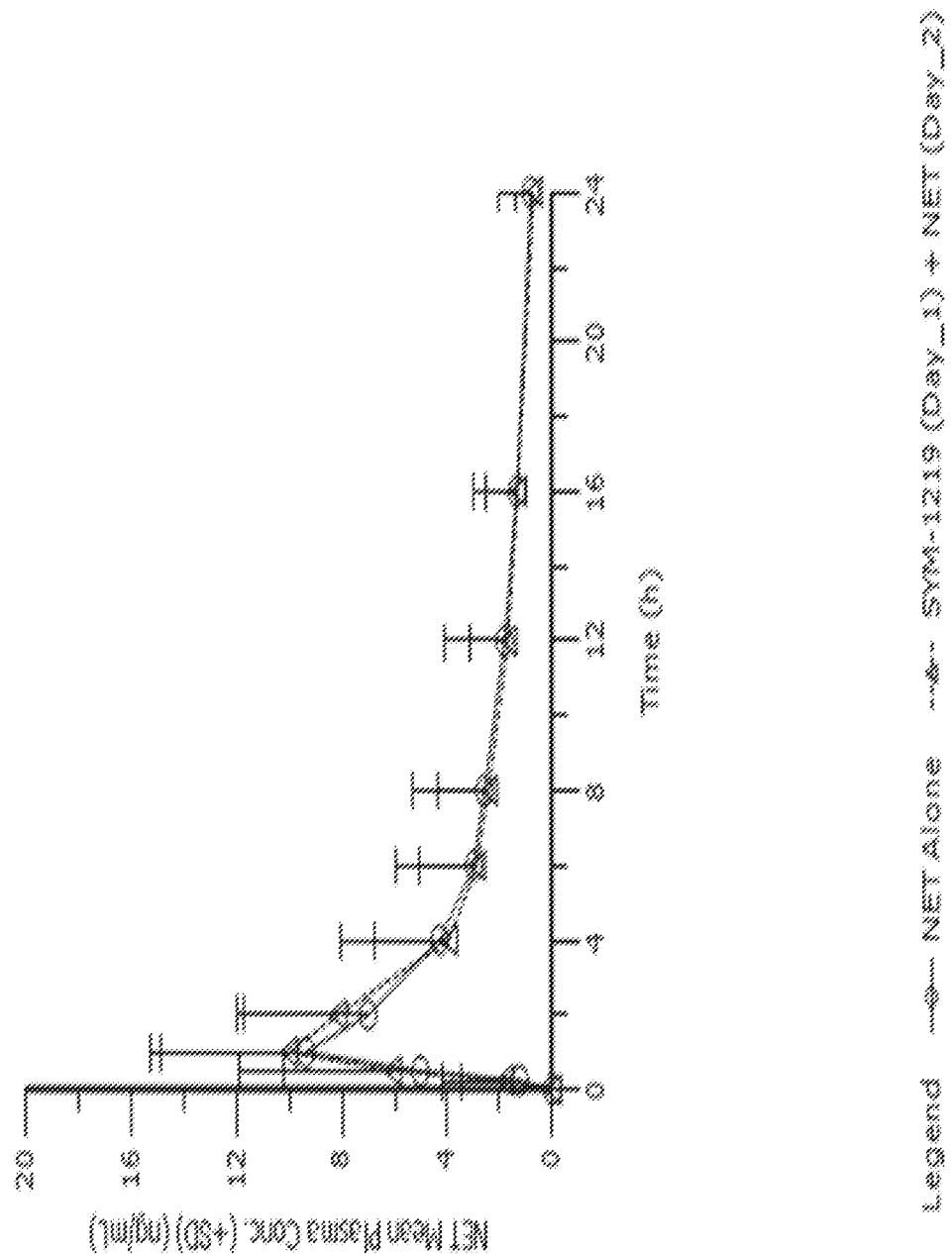
FIG. 5 illustrates the mean (±SD) NET plasma levels (ng/mL) for Group B2 over time where (1) NET alone was administered on Day 1 of Period 1 (circle markers), and (2) 2 gram microgranule formulation of SYM-1219 was administered on Day 1 of Period 2 and NET was administered on Day 2 of Period 2 (triangle markers).

Results: Fifty-one (N=26 for B1 and N=25 for B2) subjects completed the study. FIG. 2 illustrates the mean (+SD) EE2 plasma concentrations (pg/mL) over time when EE2 was administered alone (circle markers) on Day 1 of Period 1 and when EE2 was administered in conjunction with 2 gram microgranule formulation SYM-1219 on Day 1 of Period 2 (triangle markers) (Group B1). FIG. 3 illustrates the mean (+SD) EE2 plasma concentrations (pg/mL) over time when (1) EE2 was administered alone (circle markers) on Day 1 of Period 1; and (2) when 2 gram microgranule formulation SYM-1219 was administered on Day 1 of Period 2 and EE2 was administered on Day 2 of Period 2 (triangle markers) (Group B2). FIG. 4 illustrates the mean (+SD) net plasma levels (ng/mL) over time when (1) NET alone was administered on Day 1 of Period 1 (circle markers), and (2) NET followed by 2 gram microgranule formulation of SYM-1219 was administered on Day 1 of Period 2 (triangle markers) (Group B1). FIG. 5 illustrates the mean (+SD) net plasma levels (ng/mL) over time when (1) NET alone was administered on Day 1 of Period 1 (circle markers), and (2) 2 gram microgranule formulation of SYM-1219 was administered on Day 1 of Period 2 and NET was administered on Day 2 of Period 2 (triangle markers) (Group B2). Table 4 below is a summary of the NET plasma pharmacokinetic parameters for Group B1 where (1) EE2/NET was administered on Day 1 of Period 1, and (2)

EE2/NET was administered followed by SYM-1219 on Day 1 of Period 2; and Group B2 where (1) EE2/NET were administered on Day 1 of Period 1, and (2) 2 g microgranule formulation of SYM-1219 was administered followed by on Day 1 of Period 2 and EE2/NET was administered on Day 2 of Period 2. Table 5 below is a summary of the percent of relative bioavailability for EE2 plasma pharmacokinetic parameters $C_{max}$, $AUC_{0-t}$, and $AUC_{0-\infty}$ for Group B1 where (1) EE2/NET was administered on Day 1 of Period 1, and (2) EE2/NET followed by SYM-1219 2 grams were administered on Day 1 of Period 2; and Group B2 where (1) EE2/NET was administered on Day 1 of Period 1, and (2) 2 grams microgranule formulation of SYM-1219 was administered on Day 1 and EE2/NET was administered on Day 2 of Period 2. Table 6 is a summary of the percent of relative bioavailability for NET plasma pharmacokinetic parameters $C_{max}$, $AUC_{0-t}$, and $AUC_{0-\infty}$ for Group B1 where (1) EE2/NET was administered on Day 1 of Period 1, and (2) EE2/NET followed by SYM-1219 2 grams were administered on Day 1 of Period 2; and Group B2 where (1) EE2/NET was administered on Day 1 of Period 1, and (2) 2 grams microgranule formulation of SYM-1219 was administered on Day 1 and EE2/NET was administered on Day 2 of Period 2.

TABLE 5

Summary of NET Plasma Pharmacokinetic Parameters by Period and Treatment - Pharmacokinetic Population (Part B)

| Parameter | Group B1[a] (N = 26) | | Group B2[a] (N = 25) | |
| --- | --- | --- | --- | --- |
| | Period 1 | Period 2 | Period 1 | Period 2 |
| $C_{max}$ (ng/mL) | | | | |
| n | 26 | 26 | 25 | 25 |
| Mean (SD) | 9.18 (5.148) | 10.07 (4.394) | 9.63 (5.419) | 10.69 (5.169) |
| % CV | 56.07 | 43.62 | 56.25 | 48.34 |
| Median | 8.00 | 9.45 | 8.16 | 9.39 |
| Min, Max | 2.7, 23.0 | 4.3, 20.7 | 3.6, 22.7 | 4.8, 28.6 |
| $T_{max}$ (h) | | | | |
| n | 26 | 26 | 25 | 25 |
| Median | 1.000 | 1.000 | 1.000 | 1.000 |
| Min, Max | 1.00, 4.00 | 0.50, 4.00 | 0.50, 2.08 | 0.25, 2.00 |
| $AUC_{0-t}$ (h*ng/mL) | | | | |
| n | 26 | 26 | 25 | 25 |
| Mean (SD) | 49.37 (34.588) | 53.45 (24.132) | 61.35 (56.872) | 61.16 (40.799) |
| % CV | 70.06 | 45.15 | 92.70 | 66.70 |
| Median | 38.67 | 48.94 | 41.66 | 44.53 |
| Min, Max | 16.7, 151.0 | 17.6, 117.6 | 17.4, 261.5 | 22.9, 185.9 |
| $AUC_{0-\infty}$ (h*ng/mL) | | | | |
| n | 26 | 26 | 25 | 25 |
| Mean (SD) | 57.79 (43.184) | 62.39 (29.937) | 74.98 (81.529) | 71.53 (51.804) |
| % CV | 74.72 | 47.98 | 108.73 | 72.42 |
| Median | 45.33 | 54.33 | 47.35 | 51.59 |
| Min, Max | 18.0, 196.9 | 20.2, 144.5 | 20.3, 397.1 | 26.2, 224.6 |
| $t_{1/2}$ (h) | | | | |
| n | 26 | 26 | 25 | 25 |
| Mean (SD) | 9.60 (2.826) | 9.60 (2.922) | 10.04 (2.829) | 9.51 (2.430) |
| Median | 8.71 | 9.12 | 9.29 | 9.19 |
| Min, Max | 6.2, 17.8 | 5.1, 16.4 | 6.8, 17.3 | 6.1, 16.6 |
| $\lambda z$ (1/h) | | | | |
| n | 26 | 26 | 25 | 25 |
| Mean (SD) | 0.07709 (0.018293) | 0.07886 (0.023816) | 0.07369 (0.017781) | 0.07685 (0.016908) |
| Median | 0.07966 | 0.07642 | 0.07458 | 0.07539 |
| Min, Max | 0.0389, 0.1125 | 0.0422, 0.1366 | 0.0401, 0.1022 | 0.0418, 0.1146 |

[a]Group B1 = EE2/NET on Day 1 of Period 1, then EE2/NET followed by SYM-1219 2 grams on Day 1 of Period 2.
Group B2 = EE2/NET on Day 1 of Period 1, then SYM-1219 2 grams on Day 1 and EE2/NET on Day 2 of Period 2.
Source: Table 14.2.2.13; Listings 16.2.2.12.4-16.2.2.12.6

TABLE 6

Summary of the Percent of Relative Bioavailability for EE2 Plasma Pharmacokinetic Parameters $C_{max}$, $AUC_{0-t}$, and $AUC_{0-\infty}$ by Treatment (Part B)

| Parameter Treatment | Period | n | Mean (% CV) | Geometric Least Squares (LS) Means (SE)[b] | % Ratio: 100 * Test/Reference[c] Geometric LSMean % Ratio (SE)[b] | 90% C.I.[b] |
|---|---|---|---|---|---|---|
| $C_{max}$ (pg/mL) | | | | | | |
| Group B1[a] | Period 2 | 26 | 59.88 (42.19) | 55.38 (2.728) | 71.07 (4.951) | (63.09, 80.05) |
| | Period 1 | 26 | 80.63 (26.84) | 77.92 (3.839) | | |
| Group B2[a] | Period 2 | 25 | 92.60 (34.77) | 87.16 (2.369) | 104.96 (4.034) | (98.28, 112.09) |
| | Period 1 | 25 | 89.12 (36.36) | 83.04 (2.257) | | |
| $AUC_{0-t}$ (h * pg/mL) | | | | | | |
| Group B1[a] | Period 2 | 26 | 615.55 (31.20) | 590.74 (11.892) | 94.26 (2.683) | (89.78, 98.95) |
| | Period 1 | 26 | 643.67 (23.85) | 626.75 (12.617) | | |
| Group B2[a] | Period 2 | 25 | 668.63 (26.22) | 643.74 (10.529) | 99.04 (2.291) | (95.20, 103.04) |
| | Period 1 | 25 | 680.48 (28.91) | 649.96 (10.631) | | |
| $AUC_{0-\infty}$ (h * pg/mL) | | | | | | |
| Group B1[a] | Period 2 | 25 | 954.35 (28.75) | 924.75 (28.869) | 105.37 (4.565) | (97.84, 113.48) |
| | Period 1 | 26 | 911.11 (29.39) | 877.60 (26.363) | | |
| Group B2[a] | Period 2 | 25 | 937.42 (33.60) | 882.24 (23.866) | 93.32 (3.570) | (87.41, 99.63) |
| | Period 1 | 25 | 994.55 (28.91) | 945.39 (25.575) | | |

[a]Group B1 = EE2/NET on Day 1 of Period 1, then EE2/NET followed by SYM-1219 2 grams on Day 1 of Period 2. Group B2 = EE2/NET on Day 1 of Period 1, then SYM-1219 2 grams on Day 1 and EE2/NET on Day 2 of Period 2.
[b]From an ANOVA model for the log-transformed results with effects treatment (Period 1: EE2/NET alone, Period 2: EE2/NET in combination with SYM-1219) and subject.
[c]Test is Period 2 [EE2/NET followed by SYM-1219 2 grams on Day 1 (Group B2) or SYM-1219 2 grams on Day 1 and EE2/NET on Day 2 (Group B2)]; Reference is Period 1 (EE2/NET Alone)
Source: Table 14.2.2.15

TABLE 7

Summary of the Percent of Relative Bioavailability for NET Plasma Pharmacokinetic Parameters $C_{max}$, $AUC_{0-t}$ and $AUC_{0-\infty}$ by Treatment (Part B)

| Parameter Treatment | Period | n | Mean (% CV) | Geometric LSMeans (SE)[b] | % Ratio: 100 * Test/Reference[c] Geometric LSMean % Ratio (SE)[b] | 90% C.I.[b] |
|---|---|---|---|---|---|---|
| $C_{max}$ (ng/mL) | | | | | | |
| Group B1[a] | Period 2 | 26 | 10.07 (43.62) | 9.16 (0.455) | 113.18 (7.958) | (100.37, 127.63) |
| | Period 1 | 26 | 9.18 (56.07) | 8.09 (0.402) | | |
| Group B2[a] | Period 2 | 25 | 10.69 (48.34) | 9.74 (0.483) | 116.46 (8.178) | (103.27, 131.32) |
| | Period 1 | 25 | 9.63 (56.25) | 8.36 (0.415) | | |
| $AUC_{0-t}$ (h * ng/mL) | | | | | | |
| Group B1[a] | Period 2 | 26 | 53.45 (45.15) | 48.72 (1.738) | 115.52 (5.828) | (105.99, 125.92) |
| | Period 1 | 26 | 49.37 (70.06) | 42.17 (1.504) | | |
| Group B2[a] | Period 2 | 25 | 61.16 (66.70) | 51.94 (1.361) | 110.78 (4.104) | (103.97, 118.03) |
| | Period 1 | 25 | 61.35 (92.70) | 46.88 (1.228) | | |
| $AUC_{0-\infty}$ (h * ng/mL) | | | | | | |
| Group B1[a] | Period 2 | 26 | 62.39 (47.98) | 56.42 (2.070) | 116.27 (6.032) | (106.41, 127.04) |
| | Period 1 | 26 | 57.79 (74.72) | 48.53 (1.780) | | |
| Group B2[a] | Period 2 | 25 | 71.53 (72.42) | 59.95 (1.640) | 108.75 (4.207) | (101.78, 116.19) |
| | Period 1 | 25 | 74.98 (108.73) | 55.13 (1.508) | | |

[a]Group B1 = EE2/NET on Day 1 of Period 1, then EE2/NET followed by SYM-1219 2 grams on Day 1 of Period 2. B2 = EE2/NET on Day 1 of Period 1, then SYM-1219 2 grams on Day 1 and EE2/NET on Day 2 of Period 2.
[b]From an ANOVA model for the log-transformed results with effects treatment (Period 1: EE2/NET alone, Period 2: EE2/NET in combination with SYM-1219) and subject.
[c]Test is Period 2 [EE2/NET followed by SYM-1219 2 grams on Day 1 (Group B2) or SYM-1219 2 grams on Day 1 and EE2/NET on Day 2 (Group B2)]; Reference is Period 1 (EE2/NET Alone)
Source: Table 14.2.2.16

EE2 $C_{max}$ was reduced by 29% (90% CI 63.09, 80.05) for Group B1; no change in EE2 AUC was seen. EE2 PK was not altered for Group B2. NET $C_{max}$ and AUC increased (13%) slightly for Group B1. NET $C_{max}$ increased by 16% for Group B2; no change was seen for NET AUC. There was no effect (90% CIs within 80-125%) on $AUC_{0-t}$ or $AUC_{0-\infty}$ when SYM-1219 was administered immediately after EE2/NET administration. When EE2/NET was administered 1 day after SYM-1219 administration, there was no effect (90% CIs within 80-125%) from SYM-1219 on EE2 $C_{max}$, $AUC_{0-t}$ or $AUC_{0-\infty}$.

Simultaneous co-administration of EE2/NET and SYM-1219 appears to decrease the rate but not the extent of EE2 absorption. Administration of EE2/NET one day after SYM-1219 appears to have no effect on EE2 absorption.

NET $C_{max}$, $AUC_{0-t}$ or $AUC_{0-\infty}$ were increased by 13-16% and the upper value of 90% CIs were just above 125% when SYM-1219 was administered immediately after EE2/NET administration. When EE2/NET was administered 1 day after SYM-1219 administration the NET $C_{max}$, $AUC_{0-t}$ or $AUC_{0-\infty}$ were increased by 9-16%. The NET upper value of the 90% CI for $C_{max}$ was 131% and there was no effect (90% CIs within 80-125%) from SYM-1219 on $AUC_{0-t}$ or $AUC_{0-\infty}$.

Simultaneous co-administration of EE2/NET and SYM-1219 may result in small (13-16%) increases in the rate and the extent of NET absorption. Administration of EE2/NET one day after SYM-1219 may result in a small (16%) increase in the rate but not the extent of NET absorption.

SYM-1219 was safe and well-tolerated when taken alone or in combination with EE2/NET. The most common adverse events were headache and nausea. All adverse events were mild and resolved without sequelae. There were no significant changes in vital signs, ECG or laboratory parameters. Concomitant administration of SYM-1219 with EE2/NET is not expected to have an effect on contraceptive efficacy.

Conclusions: This study characterized the PK of EE2/NET with SYM-1219 co-administration. Minor, clinically insignificant, reductions in EE2 exposure were seen when SYM-1219 and EE2/NET were co-administered on the same day. No change in EE2 exposure was seen when the SYM-1219 and EE2/NET doses were staggered by one day. No reductions in drug exposure were evident for NET for either treatment group. These in vivo data indicate that contraceptive efficacy for EE2/NET will not be altered by SYM-1219 administration. This was surprising in light of in vitro metabolism data indicating that concentrations of EE2 and NET may be lowered and contraceptive efficacy may be adversely affected by co-administration of SYM-1219.

Example 3

This study was a Phase 2, multicenter, prospective, double-blind, placebo-controlled study to evaluate the effectiveness and safety of SYM-1219 for the treatment of women with bacterial vaginosis. The study was designed in accordance with FDA guidance for pivotal bacterial vaginosis trials with a primary end point clinical cure in the Modified Intent-to-Treat (mITT) population at day 21 to day 30 versus placebo (two-sided test at alpha=0.05). Subjects were recruited to the study they presented with the following Amsel criteria: presence of typical discharge. a positive KOH Whiff test vaginal fluid pH greater than or equal to 4.7, and the presence of "clue cells" (epithelial cells with adhering bacteria) on microscopic examination. Table 8 shows that a 2 gram single-dose of SYM-1219 is effective for bacterial vaginosis compared with placebo.

TABLE 8

Summary of Clinical Outcome Responder Rates by Treatment Modified Intent-to-Treat Population (mITT)

| | SYM-1219 2 grams (N = 62) n (%) | Placebo (N = 62) n (%) |
|---|---|---|
| Clinical Outcome Responder[a] | 42 (67.7) | 11 (17.7) |
| Non-Responder | 20 (32.3) | 51 (82.3) |
| P-value[b] | <0.001 | |
| 95% Exact Binomial C.I. for Responder Rate | 54.7, 79.1 | 9.2, 29.5 |

[a]Clinical Outcome Responder is defined as a subject who had all three of the following at TOC/EOS: normal vaginal discharge, negative KOH Whiff test, and clue cells <20%.
[b]P-value versus placebo from CMH test adjusted for BV strata (≤3 or >3 episodes in the past 12 months)

As can be seen in Table 9, a single dose of 2 grams of SYM-1219 was surprisingly well tolerated.

TABLE 9

Summary of Treatment-Emergent Adverse Events by Treatment Safety Population

| System Organ Class Preferred Term | | SYM-1219 2 grams (N = 72) | Placebo (N = 72) |
|---|---|---|---|
| Any Adverse Event | | | |
| Overall | Subjects[a], [n (%)] | 14 (19.4) | 7 (9.7) |
| | Events, [n] | 19 | 7 |
| Infections and infestations | | | |
| Overall | Subjects[a], [n (%)] | 5 (6.9) | 6 (8.3) |
| | Events, [n] | 7 | 6 |
| Vulvovaginal mycotic infection | Subjects[a], [n (%)] | 2 (2.8) | 1 (1.4) |
| | Events, [n] | 2 | 1 |
| Candida infection | Subjects[a], [n (%)] | 0 | 0 |
| | Events, [n] | 0 | 1 |
| Chlamydial infection | Subjects[a], [n (%) | 1 (1.4) | 0 |
| | Events, [n] | 1 | 0 |
| Fungal infection | Subjects[a], [n (%) | 0 | 1 (1.4) |
| | Events, [n] | 0 | 1 |
| Gonorrhoea | Subjects[a], [n (%)] | 1 (1.4) | 0 |
| | Events, [n] | 1 | 0 |
| Tooth abscess | Subjects[a], [n (%)] | 1 (1.4) | 1 (1.4) |
| | Events, [n] | 1 | 1 |
| Tooth infection | Subjects[a], [n (%)] | 1 (1.4) | 0 |
| | Events, [n] | 1 | 0 |
| Urinary tract infection | Subjects[a], [n (%)] | 1 (1.4) | 0 |
| | Events, [n] | 1 | 0 |
| Upper respiratory tract infection | Subjects[a], [n (%)] | 0 | 2 (2.8) |
| | Events, [n] | 0 | 2 |
| Acute sinusitis | Subjects[a], [n (%)] | 0 | 1 (1.4) |
| | Events, [n] | 0 | 1 |
| Nervous system disorders | | | |
| Overall | Subjects[a], [n (%)] | 3 (4.2) | 0 |
| | Events, [n] | 3 | 0 |
| Headache | Subjects[a], [n (%)] | 1 (1.4) | 0 |
| | Events, [n] | 1 | 0 |
| Dizziness | Subjects[a], [n (%)] | 1 (1.4) | 0 |
| | Events, [n] | 1 | 0 |
| Dysgeusia | Subjects[a], [n (%)] | 1 (1.4) | 0 |
| | Events, [n] | 1 | 0 |
| Reproductive system and breast disorders | | | |
| Overall | Subjects[a], [n (%)] | 2 (2.8) | 0 |
| | Events, [n] | 3 | 0 |
| Vaginal discharge | Subjects[a], [n (%)] | 1 (1.4) | 0 |
| | Events, [n] | 1 | 0 |

TABLE 9-continued

Summary of Treatment-Emergent Adverse Events by Treatment Safety Population

| System Organ Class<br>Preferred Term | | SYM-1219<br>2 grams<br>(N = 72) | Placebo<br>(N = 72) |
|---|---|---|---|
| Vaginal odor | Subjects[a], [n (%)] | 1 (1.4) | 0 |
| | Events, [n] | 1 | 0 |
| Vulvovaginal pruritus | Subjects[a], [n (%)] | 1 (1.4) | 0 |
| | Events, [n] | 1 | 0 |
| Investigations | | | |
| Overall | Subjects[a], [n (%)] | 1 (1.4) | 0 |
| | Events, [n] | 2 | 0 |
| Alanine aminotransferase increased | Subjects[a], [n (%)] | 1 (1.4) | 0 |
| | Events, [n] | 1 | 0 |
| Aspartate aminotransferase increased | Subjects[a], [n (%)] | 1 (1.4) | 0 |
| | Events, [n] | 1 | 0 |
| Renal and urinary disorders | | | |
| Overall | Subjects[a], [n (%)] | 1 (1.4) | 0 |
| | Events, [n] | 1 | 0 |
| Chromaturia | Subjects[a], [n (%)] | 1 (1.4) | 0 |
| | Events, [n] | 1 | 0 |
| Gastrointestinal disorders | | | |
| Overall | Subjects[a], [n (%)] | 1 (1.4) | 0 |
| | Events, [n] | 1 | 0 |
| Nausea | Subjects[a], [n (%)] | 1 (1.4) | 0 |
| | Events, [n] | 1 | 0 |
| Injury, poisoning and procedural complications | | | |
| Overall | Subjects[a], [n (%)] | 1 (14) | 0 |
| | Events, [n] | 1 | 0 |
| Thermal burn | Subjects[a], [n (%)] | 1 (1.4) | 0 |
| | Events, [n] | 1 | 0 |
| Respiratory, thoracic and mediastinal disorders | | | |
| Overall | Subjects[a], [n (%)] | 1 (1.4) | 0 |
| | Events, [n] | 1 | 0 |
| Oropharyngeal pain | Subjects[a], [n (%)] | 1 (1.4) | 0 |
| | Events, [n] | 1 | 0 |
| Surgical and medical procedures | | | |
| Overall | Subjects[a], [n (%)] | 0 | 1 (1.4) |
| | Events, [n] | 0 | 1 |
| Tooth extraction | Subjects[a], [n (%)] | 0 | 1 (1.4) |
| | Events, [n] | 0 | 1 |

[a]Subjects experiencing multiple adverse events are only counted once within a given cell.

TABLE 10

Summary of Clinical Outcome Responder Rates by Bacterial Vaginosis Strata and Treatment Modified Intent-To-Treat Population.

| | SYM-1219<br>2 grams<br>(N = 62)<br>n (%) | Placebo<br>(N = 62)<br>n (%) |
|---|---|---|
| 3 or fewer episodes in the past 12 months | | |
| Clinical Outcome Responder[a] | 30 (73.2) | 10 (23.3) |
| Non-Responder | 11 (26.8) | 33 (76.7) |
| P-value[b] | <0.001 | |
| 95% Exact Binomial C.I. for Responder Rate | 57.1, 85.8 | 11.8, 38.6 |
| 4 or more episodes in the past 12 months | | |
| Clinical Outcome Responder[a] | 12 (57.1) | 1 (5.3) |
| Non-Responder | 9 (42.9) | 18 (94.7) |
| P-value[b] | <0.001 | |
| 95% Exact Binomial C.I. for Responder Rate | 34.0, 78.2 | 0.1, 26.0 |

[a]Clinical Outcome Responder is defined as a subject who had all three of the following at TOC/EOS: normal vaginal discharge, negative KOH Whiff test, and clue cells <20%.
[b]P-value versus placebo from CMH test
Source: Listing 16.2.1.6

A 2 gram single dose of SYM-219 was found to be effective in treating bacterial vaginosis in subjects having had 3 or fewer bacterial vaginosis infections/episodes in the past 12 months, as well as in subjects having had 4 or more bacterial vaginosis infections/episodes in the past twelve months (See Table 10).

Example 3

In the mITT population, using a time stamped telephone diary questionnaire, on a five-point scale composed of (1) Normal/Not an Issue, (2) Mildly Abnormal, (3) Moderately Abnormal, (4) Severely Abnormal and (5) Very Severely Abnormal, the proportion of women on a 2 g dose reporting 3-5 for vaginal discharge declined from 59% on day 1, to 30% on day 3 (~48 hours), and to 14% on day 7 as can be seen in Table 11. The proportion of women on a 2 g dose reporting 4-5 for vaginal discharge declined from 36% on day 1, to 11% on day 3 (~48 hours), and to 0% on day 7 as can be seen in Table 11. The proportion of women on a 2 g dose reporting 3-5 for vaginal odor declined from 66% on day 1, to 20% on day 3 (~48 hours), and to 9% on day 7 as can be seen in Table 11. The proportion of women on a 2 g dose reporting 4-5 for vaginal odor declined from 38% on day 1, to 9% on day 3 (~48 hours), and to 0% on day 7 as can be seen in Table 11

TABLE 11

Results of Telephone Diary Questionnaire

| mITT | Points | Day 1 | | Day 2 | | Day 3 | | Day 4 | | Day 5 | | Day 6 | | Day 7 | | EOS | |
|---|---|---|---|---|---|---|---|---|---|---|---|---|---|---|---|---|---|
| 2 g - Discharge | 1 | 6 | 10% | 9 | 17% | 13 | 24% | 19 | 35% | 21 | 43% | 22 | 47% | 24 | 55% | 36 | 68% |
| | 2 | 18 | 31% | 20 | 38% | 25 | 46% | 22 | 40% | 17 | 35% | 15 | 32% | 14 | 32% | 9 | 17% |
| | 3 | 13 | 22% | 15 | 29% | 10 | 19% | 8 | 15% | 4 | 8% | 7 | 15% | 6 | 14% | 4 | 8% |
| | 4 | 17 | 29% | 3 | 6% | 3 | 6% | 5 | 9% | 6 | 12% | 2 | 4% | 0 | 0% | 3 | 6% |
| | 5 | 4 | 7% | 5 | 10% | 3 | 6% | 1 | 2% | 1 | 2% | 1 | 2% | 0 | 0% | 1 | 2% |
| | Total | 58 | | 52 | | 54 | | 55 | | 49 | | 47 | | 44 | | 53 | |
| 2 g - Odor | 1 | 8 | 14% | 10 | 19% | 20 | 37% | 27 | 49% | 28 | 58% | 29 | 62% | 33 | 75% | 36 | 69% |
| | 2 | 12 | 21% | 23 | 44% | 23 | 43% | 18 | 33% | 12 | 25% | 12 | 26% | 7 | 16% | 7 | 13% |
| | 3 | 16 | 28% | 10 | 19% | 6 | 11% | 6 | 11% | 5 | 10% | 5 | 11% | 4 | 9% | 9 | 17% |

TABLE 11-continued

Results of Telephone Diary Questionnaire

| mITT | Points | Day 1 | | Day 2 | | Day 3 | | Day 4 | | Day 5 | | Day 6 | | Day 7 | | EOS | |
|---|---|---|---|---|---|---|---|---|---|---|---|---|---|---|---|---|---|
| | 4 | 17 | 29% | 8 | 15% | 4 | 7% | 4 | 7% | 3 | 6% | 1 | 2% | 0 | 0% | 0 | 0% |
| | 5 | 5 | 9% | 1 | 2% | 1 | 2% | 0 | 0% | 0 | 0% | 0 | 0% | 0 | 0% | 0 | 0% |
| | Total | 58 | | 52 | | 54 | | 55 | | 48 | | 47 | | 44 | | 52 | |

While the illustrative embodiments of the invention have been described with particularity, it will be understood that various other modifications will be apparent to and can be readily made by those skilled in the art without departing from the spirit and scope of the invention. Accordingly, it is not intended that the scope of the embodiments above be limited to the examples and descriptions set forth hereinabove but rather that the invention be construed as encompassing all the features of patentable novelty which reside in embodiments described herein, including all features which would be treated as equivalents thereof by those skilled in the relevant art.

We claim:

1. A method of treating a sexually transmitted infection (STI) in a subject in need thereof, the method comprising:
   administering to the subject a therapeutically effective amount of secnidazole in a microgranule formulation, wherein the microgranule formulation comprises a plurality of microgranules, each microgranule comprises a sugar core or a microcrystalline cellulose core, and an outer layer on the sugar core or the microcrystalline cellulose core, the outer layer comprises secnidazole,
   wherein at least 10% of the plurality of microgranules have a volume-weighted particle diameter equal to or larger than 470 micrometers as measured by laser diffraction,
   wherein the microgranule formulation provides a maximum plasma concentration ($C_{max}$) of secnidazole in the subject of about 34.5 µg/ml to about 58.3 µg/ml, and wherein the secnidazole is the sole drug in the microgranule formulation.

2. The method of claim 1, wherein the STI is chlamydia, gonorrhea, bacterial vaginosis, trichomoniasis, herpes simplex virus type 2 (HSV-2), human papillomavirus (HPV), or a combination thereof.

3. The method of claim 1, wherein the therapeutically effective amount of secnidazole in the microgranule formulation is administered orally.

4. The method of claim 1, wherein the microgranule formulation is a taste-masked formulation.

5. The method of claim 1, wherein the sugar core is a sugar sphere core.

6. The method of claim 1, wherein the microgranule formulation further comprises at least one compound selected from the group consisting of povidone, polyethylene glycol, a copolymer of ethyl acetate and methyl methacrylate, and talc.

7. The method of claim 1, wherein the microgranule formulation is integrated into a food substance or a liquid prior to administration.

8. The method of claim 7, wherein the food substance is a liquid, semisolid or soft food.

9. The method of claim 1, wherein the therapeutically effective amount of secnidazole in the microgranule formulation is administered as a single dose.

10. The method of claim 1, wherein the therapeutically effective amount of secnidazole in the microgranule formulation is 2 grams.

11. The method of claim 1, wherein the therapeutically effective amount of secnidazole in the microgranule formulation is co-administered with an additional compound selected from ethinyl estradiol, norethindrone or a combination thereof.

12. The method of claim 11, wherein the additional compound is administered on the same day as the therapeutically effective amount of secnidazole in the microgranule formulation.

13. The method of claim 11, wherein the additional compound is administered on a different day as the therapeutically effective amount of secnidazole in the microgranule formulation.

14. The method of claim 11, wherein the microgranule formulation does not affect a contraceptive efficacy of the additional compound selected from ethinyl estradiol, norethindrone or a combination thereof.

15. A method of treating a sexually transmitted infection (STI) in a subject in need thereof, the method comprising:
   administering to the subject a therapeutically effective amount of secnidazole in a microgranule formulation, wherein the microgranule formulation comprises a plurality of microgranules, each microgranule comprises a sugar core or a microcrystalline cellulose core, and an outer layer on the sugar core or the microcrystalline cellulose core, the outer layer comprises secnidazole,
   wherein at least 10% of the plurality of microgranules have a volume-weighted particle diameter equal to or larger than 470 micrometers as measured by laser diffraction,
   wherein the microgranule formulation provides a time to maximum plasma concentration ($T_{max}$) of secnidazole of about 2 hours to about 6 hours after administering to the subject), and wherein the secnidazole is the sole drug in the microgranule formulation.

16. The method of claim 15, wherein the STI is chlamydia, gonorrhea, bacterial vaginosis, trichomoniasis, HSV-2, HPV, or a combination thereof.

17. The method of claim 15, wherein the $T_{max}$ of secnidazole is about 3 hours to about 4 hours.

18. A method of treating trichomoniasis in a subject in need thereof, the method comprising:
   administering to the subject a therapeutically effective amount of secnidazole in a microgranule formulation, wherein the microgranule formulation comprises a plurality of microgranules, each microgranule comprises a sugar core or a microcrystalline cellulose core, and an outer layer on the sugar core or the microcrystalline cellulose core, the outer layer comprises secnidazole, wherein at least 10% of the plurality of microgranules have a volume-weighted particle diameter equal to or larger than 470 micrometers as measured by laser diffraction, wherein the microgranule formulation provides a maximum plasma concentration ($C_{max}$) of secnidazole in the subject of about 34.5 µg/ml to about 58.3 µg/ml or a time to maximum plasma concentration ($T_{max}$) of secnidazole of about 2 hours to about 6 hours after administering to the subject, and wherein the secnidazole is the sole drug in the microgranule formulation.

19. A pharmaceutical composition comprising a therapeutically effective amount of secnidazole in a microgranule formulation, wherein the microgranule formulation comprises a plurality of microgranules, each microgranule comprises a sugar core or a microcrystalline cellulose core, and an outer layer on the sugar core or the microcrystalline cellulose core, the outer layer comprises secnidazole, wherein at least 10% of the plurality of microgranules have a volume-weighted particle diameter equal to or larger than 470 micrometers as measured by laser diffraction, wherein the microgranule formulation provides a maximum plasma concentration ($C_{max}$) of secnidazole in the subject of about 34.5 µg/ml to about 58.3 µg/ml or a time to maximum plasma concentration ($T_{max}$) of secnidazole of about 2 hours to about 6 hours after administering to the subject, and wherein the secnidazole is the sole drug in the microgranule formulation.

20. The pharmaceutical composition of claim 19, wherein the volume-weighted particle size distribution as measured by laser diffraction from a representative sample of the microgranule population further comprises (a) 50% of the microgranule population having a volume-weighted particle diameter size in a range of from 640 micrometers to 810 micrometers, and (b) 90% of the microgranule population having a volume-weighted particle diameter smaller than 1170 micrometers.

21. A method for treating an STI in a subject in need thereof, the method comprising co-administering the pharmaceutical composition of claim 19 to the subject with an additional compound selected from the group consisting of ethinyl estradiol, norethindrone, and a combination thereof.

22. The method of claim 21, wherein the STI is *chlamydia*, gonorrhea, bacterial vaginosis, trichomoniasis, HSV-2, HPV, or a combination thereof.

* * * * *